United States Patent
Brown

(10) Patent No.: US 11,059,807 B2
(45) Date of Patent: *Jul. 13, 2021

(54) AMINE CATIONIC LIPIDS AND USES THEREOF

(71) Applicant: Dicerna Pharmaceuticals, Inc., Lexington, MA (US)

(72) Inventor: Bob Dale Brown, Millington, NJ (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 163 days.

This patent is subject to a terminal disclaimer.

(21) Appl. No.: 16/204,053

(22) Filed: Nov. 29, 2018

(65) Prior Publication Data

US 2019/0084965 A1     Mar. 21, 2019

Related U.S. Application Data

(63) Continuation of application No. 15/407,512, filed on Jan. 17, 2017, now Pat. No. 10,144,725, which is a continuation of application No. 14/255,637, filed on Apr. 17, 2014, now Pat. No. 9,549,983, which is a continuation of application No. PCT/US2012/060875, filed on Oct. 18, 2012.

(Continued)

(51) Int. Cl.

| | | |
|---|---|---|
| *C07D 403/06* | (2006.01) | |
| *C07D 233/61* | (2006.01) | |
| *C07D 233/64* | (2006.01) | |
| *C07D 239/42* | (2006.01) | |
| *C07D 241/04* | (2006.01) | |
| *C07C 237/06* | (2006.01) | |
| *C07D 295/03* | (2006.01) | |
| *C07D 211/36* | (2006.01) | |
| *C07D 295/13* | (2006.01) | |
| *C07D 295/15* | (2006.01) | |
| *C07C 211/21* | (2006.01) | |
| *C12N 15/11* | (2006.01) | |
| *C12N 15/113* | (2010.01) | |
| *C12N 15/88* | (2006.01) | |
| *A61K 9/127* | (2006.01) | |
| *A61K 31/713* | (2006.01) | |
| *A61K 47/18* | (2017.01) | |
| *A61K 47/22* | (2006.01) | |
| *A61K 9/107* | (2006.01) | |
| *A61K 9/14* | (2006.01) | |
| *C07D 243/08* | (2006.01) | |
| *C07D 401/04* | (2006.01) | |
| *C07D 403/04* | (2006.01) | |
| *A61K 38/00* | (2006.01) | |

(52) U.S. Cl.
CPC ............ *C07D 403/06* (2013.01); *A61K 9/107* (2013.01); *A61K 9/127* (2013.01); *A61K 9/1272* (2013.01); *A61K 9/145* (2013.01); *A61K 9/146* (2013.01); *A61K 31/713* (2013.01); *A61K 47/18* (2013.01); *A61K 47/22* (2013.01); *C07C 211/21* (2013.01); *C07C 237/06* (2013.01); *C07D 211/36* (2013.01); *C07D 233/61* (2013.01); *C07D 233/64* (2013.01); *C07D 239/42* (2013.01); *C07D 241/04* (2013.01); *C07D 243/08* (2013.01); *C07D 295/03* (2013.01); *C07D 295/13* (2013.01); *C07D 295/15* (2013.01); *C07D 401/04* (2013.01); *C07D 403/04* (2013.01); *C12N 15/111* (2013.01); *C12N 15/1137* (2013.01); *C12N 15/88* (2013.01); *A61K 38/00* (2013.01); *C12N 2310/14* (2013.01); *C12N 2310/321* (2013.01); *C12N 2320/32* (2013.01); *C12Y 204/02008* (2013.01)

(58) Field of Classification Search
CPC ...... A61K 31/713; A61K 38/00; A61K 47/18; A61K 47/22; A61K 9/127; C07C 211/21; C07C 237/06; C07D 211/36; C07D 233/61; C07D 233/64; C07D 239/42; C07D 241/04; C07D 295/03; C07D 295/13; C07D 295/15; C12N 15/111; C12N 15/1137; C12N 15/88; C12N 2310/14; C12N 2320/32; C12Y 204/02008
USPC ............... 514/44 A, 788; 544/178, 400, 402; 546/187, 197, 509
See application file for complete search history.

(56) References Cited

U.S. PATENT DOCUMENTS

| | | |
|---|---|---|
| 3,288,774 A | 11/1966 | Cyba |
| 5,744,335 A | 4/1998 | Wolf et al. |

(Continued)

FOREIGN PATENT DOCUMENTS

| | | |
|---|---|---|
| WO | 97/000241 | 1/1997 |
| WO | 97/003939 | 2/1997 |

(Continued)

OTHER PUBLICATIONS

Canadian Office Action dated May 7, 2019 for Canadian Application No. 2,852,917, 3 pages.

(Continued)

*Primary Examiner* — Janet L Epps-Smith
(74) *Attorney, Agent, or Firm* — Byron V. Olsen; MH2 Technology Law Group, LLP

(57) ABSTRACT

The present invention relates to lipid compounds and uses thereof. In particular, the compounds include a class of cationic lipids having an amine moiety, such as an amino-amine or an amino-amide moiety. The lipid compounds are useful for in vivo or in vitro delivery of one or more agents (e.g., a polyanionic payload or an antisense payload, such as an RNAi agent).

27 Claims, 25 Drawing Sheets

Specification includes a Sequence Listing.

Related U.S. Application Data

(60) Provisional application No. 61/548,598, filed on Oct. 18, 2011.

(56) References Cited

U.S. PATENT DOCUMENTS

| | | | |
|---|---|---|---|
| 6,020,526 A | 2/2000 | Schwartz | |
| 6,121,457 A | 9/2000 | Wang et al. | |
| 10,144,725 B2 * | 12/2018 | Brown | C07D 403/04 |
| 2009/0023215 A1 | 1/2009 | Jessee et al. | |
| 2009/0285881 A1 * | 11/2009 | Dande | C07C 45/515 424/450 |
| 2010/0055168 A1 * | 3/2010 | Dande | A61K 9/1271 424/450 |
| 2010/0063135 A1 * | 3/2010 | Dande | A61K 9/1271 514/44 R |

FOREIGN PATENT DOCUMENTS

| | | | |
|---|---|---|---|
| WO | 98/005678 | | 2/1998 |
| WO | 02/016552 | | 2/2002 |
| WO | 2006/118327 | | 11/2006 |
| WO | 2007/130073 | A1 | 11/2007 |
| WO | 2008/004058 | | 1/2008 |
| WO | 2009/129385 | A1 | 10/2009 |
| WO | 2010/030730 | A1 | 3/2010 |
| WO | 2010/030739 | A1 | 3/2010 |
| WO | WO-2010030739 | A1 * | 3/2010 ........... A61K 9/0019 |
| WO | 2010/054405 | | 5/2010 |
| WO | 2011/022460 | A1 | 2/2011 |
| WO | 2011/075656 | A1 | 6/2011 |
| WO | 2011/090965 | A1 | 7/2011 |
| WO | 2011/141705 | | 11/2011 |
| WO | 2012/000104 | | 1/2012 |

OTHER PUBLICATIONS

Yagi et al., "Interferon-beta endogenously produced by intratumoral injection of cationic liposome-encapsulated gene: cytocidal effect on glioma transplanted into nude mouse brain", Biochemistry and Molecular Biology International, Jan. 1994, vol. 32, No. 1, pp. 167-171.

Japanese Office Action dated Dec. 3, 2018 for Japanese Application No. 2018-024706, 7 pages (including English translation).

Japanese Office Action dated Jun. 12, 2017 for Japanese Application No. 2014-537255, 10 pages (including English translation).

Supplemental European Search Report dated Apr. 16, 2015 for European Application No. EP12841768, 7 pages.

Hopkins et al., "ADMET Synthesis of Polyolefins Targeted for Biological Applications," Macromolecules, 2004, vol. 37, No. 4, pp. 1180-1189.

Hopkins et al., "Amino Acid and Dipeptide Functionalized Polyolefins," Macromolecules, 2003, vol. 36, No. 7, pp. 2206-2214.

Meekel et al., "Synthesis of Pyridinium Amphiphiles Used for Transfection and Some Characteristics of Amphiphile/DNA Complex Formation," Eur. J. Org. Chem., 2000, vol. 4, pp. 665-673.

International Search Report and Written Opinion dated Mar. 14, 2013 for International Application No. PCT/US12/60875 (Authorized Officer, Lee W. Young),12 pages.

* cited by examiner

AMINE CATIONIC LIPIDS AND USES THEREOF

CROSS-REFERENCE TO RELATED APPLICATION

This application is a continuation of U.S. application Ser. No. 15/407,512 (now U.S. Pat. No. 10,144,725), filed 17 Jan. 2017, which is a divisional of U.S. Ser. No. 14/255,637, filed Apr. 17, 2014, (now U.S. Pat. No. 9,549,983), which is a continuation application of PCT/US12/060875, filed Oct. 18, 2012, which claims priority to U.S. Provisional Application No. 61/548,598, filed Oct. 18, 2011, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on 25 Oct. 2018, is named 0243 0022-02_Sequence_Listing.txt and is 2 Kilobytes in size.

BACKGROUND OF THE INVENTION

The invention relates, in part, to amine cationic lipid compounds, as well as formulations thereof, and their use in the delivery of therapeutic agents, such as nucleic acid molecules, to cells.

Nucleic acid molecules cannot easily cross cell membranes because of their size and hydrophilicity. Delivery has therefore been one of the major challenges for nucleic acid therapeutics, e.g., antisense payloads and RNAi technology. To trigger RNase H activity or RNAi activity following systemic administration, a formulation containing nucleic acid molecules not only must (1) protect the payload from enzymatic and non-enzymatic degradation and (2) provide appropriate biodistribution of the formulation, but also (3) allow cellular uptake or internalization of the formulation and (4) facilitate delivery of the nucleic acid payload to the cytoplasm of the cell. Many formulations that excel in criteria 1 and 2 above are deficient in criteria 3 and 4, and many nucleic acid formulations therefore show excellent biodistribution but fail to knock down the target gene due to lack of systemic delivery and local delivery.

Accordingly, there is a need for new compounds for the delivery of therapeutic agents, such as RNAi agents. In particular, compounds capable of acting as cationic lipids may be used in lipid particle formulations to deliver nucleic acid payloads to cells.

SUMMARY OF THE INVENTION

We have developed novel amine-based lipid compounds, including amino-amine and amino-amide cationic lipids, as well as formulations thereof, for the delivery of one or more therapeutic agents. In particular, the compounds of the invention (e.g., compounds of formulas (I) or II(a)-II(k)) can be used to deliver a polyanionic payload or an antisense payload (e.g., nucleic acid molecules or RNAi agents) to cells and silence a target gene.

In one aspect, the invention features a compound having the formula:

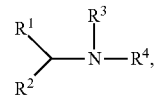
(I)

or a pharmaceutically acceptable salt thereof, where
each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl, where the $R^1$ and $R^2$ is not substituted with an oxo on the carbon adjacent to >CHNR$^3$R$^4$;
$R^3$ is H or optionally substituted $C_{1-6}$ alkyl; and
$R^4$ is unsubstituted $C_{1-6}$ alkyl that is substituted with —NR$^{4a}$R$^{4b}$, substituted $C_{1-6}$ alkyl that is further substituted with —NR$^{4a}$R$^{4b}$, or optionally substituted $C_{3-7}$ heterocyclyl, where each $R^{4a}$ and $R^{4b}$ is, independently, H, C(=NH)NH$_2$, or optionally substituted $C_{1-6}$ alkyl, or where $R^{4a}$ and $R^{4b}$ combine together to form optionally substituted $C_{3-7}$ heterocyclyl; and where $R^3$ and $R^4$ can combine together to form an optionally substituted $C_{3-7}$ heterocyclyl,
where $R^3$ and $R^4$ do not combine together to form optionally substituted imidazolyl or optionally substituted benzimidazolyl or optionally substituted succinimidyl; where one, and only one, primary amine can be present on either $R^3$ or $R^4$ or no primary amine is present on either $R^3$ or $R^4$; and where neither $R^3$ nor $R^4$ is an optionally substituted amide; and
where when $R^1$ or $R^2$ is saturated $C_{11}$ alkyl or saturated $C_{15}$ alkyl, $R^3$ is not H; where when $R^1$ or $R^2$ is saturated $C_{16}$ alkyl or saturated $C_{17}$ alkyl, $R^1$ and $R^2$ is not substituted with hydroxy; where when $R^1$ or $R^2$ is saturated $C_{17}$ alkyl, $R^3$ or $R^4$ is not substituted with hydroxy; and where when $R^1$ or $R^2$ is saturated $C_{18}$ alkyl, $R^4$ is not substituted with optionally substituted imidazolyl.

In some embodiments, $R^3$ is $C_{1-6}$ alkyl substituted with —NR$^{3a}$R$^{3b}$ and where each $R^{3a}$ and $R^{3b}$ is, independently, H or optionally substituted $C_{1-6}$ alkyl. In particular embodiments, each $R^{3a}$ and $R^{3b}$ is, independently, H or $C_{1-6}$ alkyl.

In some embodiments, $R^4$ is unsubstituted $C_{1-6}$ alkyl that is substituted with —NR$^{4a}$R$^{4b}$. In particular embodiments, $R^4$ is substituted $C_{1-6}$ alkyl (e.g., substituted $C_{1-3}$ alkyl, substituted $C_{1-2}$ alkyl, substituted $C_1$ alkyl, substituted $C_2$ alkyl, or substituted $C_3$ alkyl) or $C_{1-6}$ aminoalkyl that is further substituted with —NR$^{4a}$R$^{4b}$. In some embodiments, $R^4$ is $C_{1-6}$ alkyl substituted with an oxo and is further substituted with —NR$^{4a}$R$^{4b}$. In some embodiments, $R^{4a}$ and $R^{4b}$ combine together to form an optionally substituted $C_{3-7}$ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, or optionally substituted pyrazolyl). In some embodiments, each $R^{4a}$ and $R^{4b}$ is, independently, optionally substituted $C_{1-6}$ alkyl. In some embodiments, $R^4$ is unsubstituted $C_{1-6}$ alkyl that is substituted with optionally substituted $C_{3-7}$ heterocyclyl (e.g., any described herein). In some embodiments, $R^4$ is substituted $C_{1-6}$ alkyl (e.g., with an oxo) or a $C_{1-6}$ aminoalkyl that is further substituted with optionally substituted $C_{3-7}$ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, $R^3$ and $R^4$ combine together to form an optionally substituted $C_{3-7}$ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, the compound has the formula:

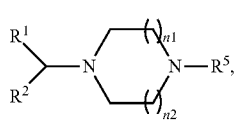

(IIa)

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; each n1 and n2 is, independently, an integer from 0 to 2 (e.g., n1 and n2 are both 1 or n1 is 1 and n2 is 2); and $R^5$ is selected from the group consisting of H, optionally substituted $C_{1-6}$ alkyl, and optionally substituted heterocyclyl (e.g., unsubstituted $C_{1-6}$ alkyl or $C_{1-6}$ alkyl substituted with optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl). In some embodiments, the compound is selected from the group consisting of L-2, L-5, L-6, L-22, L-23, L-24, L-25, L-26, L-28, L-29, L-45, and L-48, or a pharmaceutically acceptable salt thereof.

In some embodiments, the compound has the formula:

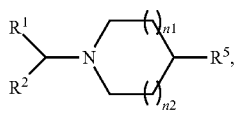

(IIb)

or a pharmaceutically acceptable salt thereof, where each $R^1$ and $R^2$ is, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, optionally substituted $C_{11-24}$ heteroalkynyl; each n1 and n2 is, independently, an integer from 0 to 2 (e.g., n1 and n2 are both 1 or n1 is 1 and n2 is 2); and $R^5$ is selected from the group consisting of H, optionally substituted $C_{1-6}$ alkyl, and optionally substituted heterocyclyl (e.g., unsubstituted $C_{1-6}$ alkyl or $C_{1-6}$ alkyl substituted with optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl). In some embodiments, the compound is selected from the group consisting of L-27 and L-47, or a pharmaceutically acceptable salt thereof.

In some embodiments for any formula described herein (e.g., formulas (I), (IIa), and (IIb)), $R^5$ is $C_{1-6}$ alkyl substituted with $NR^{5a}R^{5b}$, where each $R^{5a}$ and $R^{5b}$ is, independently, H, optionally substituted $C_{1-6}$ alkyl (e.g., optionally substituted $C_{1-6}$ alkyl), and where $R^{5a}$ and $R^{5b}$ can combine together to form optionally substituted $C_{3-7}$ heterocyclyl. In some embodiments, $R^5$ is optionally substituted heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, the compound has the formula:

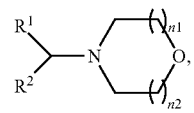

(IIc)

or a pharmaceutically acceptable salt thereof, where each $R^1$ and $R^2$ is, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, optionally substituted $C_{11-24}$ heteroalkynyl; and each n1 and n2 is, independently, an integer from 0 to 2 (e.g., n1 and n2 are both 1 or n1 is 1 and n2 is 2). In some embodiments, the compound is L-46, or a pharmaceutically acceptable salt thereof.

In some embodiments, the compound has the formula:

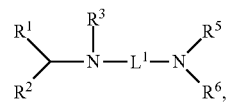

(IId)

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl, or where $R^5$ and $R^6$ combine to form an optionally substituted $C_{3-7}$ heterocyclyl.

In some embodiments, the compound has the formula:

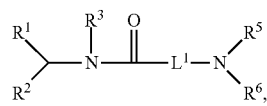

(IIe)

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl, or where $R^5$ and $R^6$ combine to form an optionally substituted $C_{3-7}$ heterocyclyl.

In some embodiments of formulas (IId) or (IIe), $R^5$ and $R^6$ combine to form optionally substituted pyrrolidinyl, optionally substituted imidazolidinyl, optionally substituted pyrazolidinyl, optionally substituted piperidinyl, optionally substituted piperazinyl, or optionally substituted azepanyl.

In some embodiments, the compound is selected from the group consisting of L-1, L-3, L-4, L-7, L-9, L-10, L-11, L-12, L-15, L-16, L-17, L-18, L-19, L-30, L-31, L-32, L-33, L-34, L-42, L-43, and L-49, or a pharmaceutically acceptable salt thereof.

In some embodiments, the compound has the formula:

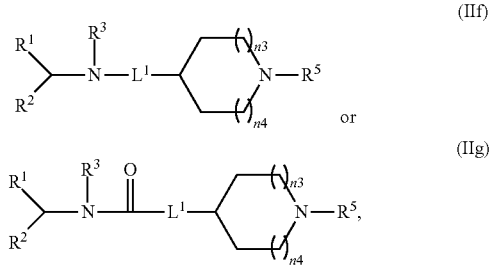

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; each n3 and n4 is, independently, an integer from 0 to 2; and $R^5$ is H or optionally substituted $C_{1-6}$ alkyl.

In some embodiments, the compound is selected from the group consisting of L-14, L-21, and L-36, or a pharmaceutically acceptable salt thereof.

In some embodiments of any formula described herein (e.g., formulas (IId)-(IIj), e.g., formulas (IId)-(IIg)), $R^3$ is $C_{1-6}$ alkyl substituted with $-NR^{3a}R^{3b}$ and where each $R^{3a}$ and $R^{3b}$ is, independently, H or optionally substituted $C_{1-6}$ alkyl. In some embodiments, $R^3$ is unsubstituted $C_{1-6}$ alkyl.

In some embodiments of any formula described herein (e.g., formulas (IId)-(IIj), e.g., formulas (IId)-(IIg)), $L^1$ is $C_{1-6}$ alkylene substituted with methyl, ethyl, propyl, or $-NR^{La}R^{Lb}$, where each $R^{La}$ and $R^{Lb}$ is, independently, H or optionally substituted $C_{1-6}$ alkyl.

In some embodiments, the compound has the formula:

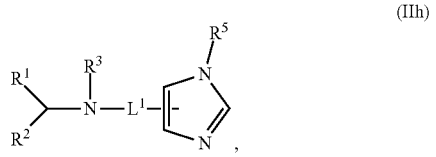

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and $R^5$ is H or optionally substituted $C_{1-6}$ alkyl.

In some embodiments, $L^1$ is linked to the imidazolyl group at the 4-position. In some embodiments, the compound is selected from the group consisting of L-8, L-13, L-20, L-35, and L-44, or a pharmaceutically acceptable salt thereof.

In some embodiments, the compound has the formula:

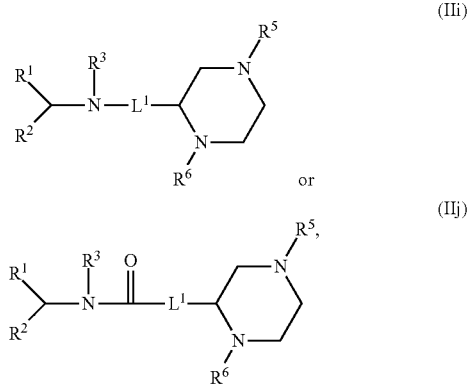

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl.

In some embodiments, the compound has the formula:

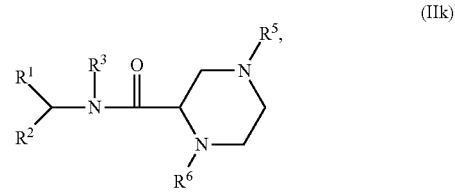

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; and each $R^5$ and $R^6$ is, independently, H or optionally substituted $C_{1-6}$ alkyl.

In some embodiments of any formula described herein (e.g., formulas (IId)-(IIk), e.g., formulas (IIi)-(IIk)), each $R^5$ and $R^6$ is, independently, $C_{1-6}$ alkyl substituted with $-NR^{5a}R^{5b}$ and where each $R^{5a}$ and $R^{5b}$ is, independently, H or optionally substituted $C_{1-6}$ alkyl.

In some embodiments, the compound is selected from the group consisting of L-37, L-38, L-39, L-40, and L-41, or a pharmaceutically acceptable salt thereof.

In some embodiments of any formula described herein (e.g., formulas (IId)-(IIk)), $L^1$ is optionally substituted $C_{1-6}$ alkylene.

In some embodiments of any formula described herein (e.g., formulas (I) or (IIa)-(IIk)), $R^3$ is optionally substituted $C_{1-6}$ alkyl. In some embodiments, each $R^1$ and $R^2$ is, independently, unsubstituted $C_{11-24}$ alkenyl or unsubstituted $C_{11-24}$ heteroalkenyl, including straight and branched forms (e.g., each $R^1$ and $R^2$ is, independently, unsubstituted $C_{11-24}$ alkenyl or unsubstituted $C_{11-24}$ heteroalkenyl containing one or more double bonds). In some embodiments, one of $R^1$ or $R^2$ is not saturated $C_{11-24}$ alkyl. In some embodiments, both $R^1$ and $R^2$ are not saturated $C_{11-24}$ alkyl. In some embodiments, each $R^1$ and $R^2$ is, independently, selected from the group consisting of linolenyl (C18:3), linolenyloxy (C18:3), linolenoyl (C18:3), linoleyl (C18:2), linoleyloxy (C18:2), linoleoyl (C18:2), oleyl (C18:1), oleyloxy (18:1), oleyloxymethylene (18:1), oleoyl (C18:1), oleoylmethylene (C18:1), stearyl (C18:0), stearyloxy (C18:0), stearoyl (C18:0), palmityl (C16:0), palmityloxy (C16:0), palmitoyl (C16:0), palmitoylmethylene (C16:0), myristyl (C14:0), myristyloxy (C14:0), myristoyl (C14:0), lauryl (C12:0), lauryloxy (C12:0), and lauroyl (C12:0), e.g., linoleyl (C18:2) or oleyl (C18:1). In some embodiments, $R^1$ and $R^2$ are the same or different.

In some embodiments of any formula described herein (e.g., formulas (I) or (IIa)-(IIk)), $R^3$ or $R^4$, but not both $R^3$ and $R^4$, is substituted with a primary amine. In some embodiments, both $R^3$ and $R^4$ is not substituted with a primary amine.

In some embodiments of any formula described herein (e.g., formulas (I) or (IIa)-(IIk)), $R^3$ and $R^4$, together with the N to which they are attached, include a head group of one of H-1 to H-52 from Tables 2 and 3. In some embodiments, each $R^1$ and $R^2$ is, independently, selected from the group consisting of linolenyl (C18:3), linolenyloxy (C18:3), linolenoyl (C18:3), linoleyl (C18:2), linoleyloxy (C18:2), linoleoyl (C18:2), oleyl (C18:1), oleyloxy (18:1), oleyloxymethylene (18:1), oleoyl (C18:1), oleoylmethylene (C18:1), stearyl (C18:0), stearyloxy (C18:0), stearoyl (C18:0), palmityl (C16:0), palmityloxy (C16:0), palmitoyl (C16:0), palmitoylmethylene (C16:0), myristyl (C14:0), myristyloxy (C14:0), myristoyl (C14:0), lauryl (C12:0), lauryloxy (C12:0), and lauroyl (C12:0), e.g., each $R^1$ and $R^2$ is, independently, linoleyl (C18:2) or oleyl (C18:1).

In another aspect, the compound of the invention include $R^1R^2$—CH-A, where $R^1$ and $R^2$ is a tail group (e.g., any described herein, e.g., in Table 4) and A is a head group (e.g., any described herein, e.g., in Tables 2 and 3). In some embodiments, the head group is one of H-1 to H-52, e.g., H-2, H-5, H-6, H-19, H-26, or H-43 (e.g., H-5 or H-43).

In another aspect, the compound of the invention is any compound provided in Table 1, or a pharmaceutically acceptable salt thereof.

In one aspect, the invention features a formulation including any compound described herein (e.g., one or more compound provided in Table 1), or a pharmaceutically acceptable salt thereof.

In some embodiments, the formulation includes two or more of the compounds, e.g., two, three, four, five, six, seven, or more of the compounds.

In some embodiments, the formulation includes between about 10% and about 80% of the compound, e.g., between about 10% and about 15%, between about 10% and about 20%, between about 10% and about 25%, between about 10% and about 30%, between about 10% and about 35%, between about 15% and about 20%, between about 15% and about 25%, between about 15% and about 30%, between about 15% and about 35%, between about 15% and about 40%, between about 20% and about 25%, between about 20% and about 30%, between about 20% and about 35%, between about 20% and about 40%, between about 25% and about 30%, between about 25% and about 35%, between about 25% and about 40%, between about 30% and about 35%, between about 30% and about 40%, or between about 35% and about 40%, of one or more compounds of the invention.

In some embodiments, the formulation further includes a cationic lipid (e.g., DODMA, DOTMA, DPePC, DODAP, or DOTAP), a neutral lipid (e.g., DSPC, POPC, DOPE, or SM), and, optionally, a sterol derivative (e.g., cholesterol; cholestanone; cholestenone; coprostanol; 3β-[-(N—(N',N'-dimethylaminoethane)-carbamoyl]cholesterol (DC-cholesterol); bis-guanidium-tren-cholesterol (BGTC); (2S,3S)-2-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonylamino)ethyl 2,3,4,4-tetrahydroxybutanoate (DPC-1); (2S,3S)-((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4,4-tetrahydroxybutanoate (DPC-2); bis((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate (DPC-3); or 6-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate (DPC-4)). In some embodiments, the formulation further includes a PEG-lipid conjugate (e.g., PEG-DMG, PEG-DMPE, PEG-DPPE, PEG-DPG, PEG-DOPE, or PEG-DOG).

In some embodiments, the formulation includes from about 10 mol % to about 40 mol % of one or more compounds of the invention (e.g., one or more of any compounds described herein, e.g., in Table 1), from about 10 mol % to about 40 mol % of one or more cationic lipids or one or more compounds of the invention (e.g., one or more of any compounds described herein, e.g., in Table 1), from about 1 mol % to about 20 mol % of one or more PEG-lipid conjugates, from about 5 mol % to about 20 mol % of one or more neutral lipids, and from about 20 mol % to about 40 mol % of one or more sterol derivatives.

In particular embodiments, the formulation includes from about 10 mol % to about 80 mol % (e.g., from about 40 mol % to about 55 mol %, such as about 48 mol %) of one or more cationic lipids (e.g., compounds of the invention and/or other cationic lipids, as described herein), from about 1 mol % to about 20 mol % of one or more PEG-lipid conjugates, from about 5 mol % to about 20 mol % of one or more neutral lipids, and from about 20 mol % to about 40 mol % of one or more sterol derivatives. In some embodiments, the formulation includes from about 10 mol % to about 30 mol % (e.g., about 22 mol %) of one or more compounds of the invention (e.g., L-6, L-30, and/or any described herein), from about 15 mol % to about 35 mol % (e.g., about 26 mol %) of one or more cationic lipids (e.g., DODMA or any described herein), from about 3 mol % to about 9 mol % (e.g., about 6 mol %) of one or more PEG-lipid conjugates (e.g., PEG-DSPE, PEG-DMPE, and/or any described herein), from about 10 mol % to about 20 mol % (e.g., about 14 mol %) of one or more neutral lipids (e.g., DSPC or any described herein), and from about 20 mol % to about 40 mol % (e.g., from about 29 mol % to about 33 mol %, such as about 33 mol %) of one or more sterol derivatives (e.g., cholesterol, a derivative thereof, or any described herein).

In some embodiments, one or more compounds of the invention is present in an amount between about 10 mol % to about 40 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 20 mol % and about 25 mol %, between about 20 mol % and about 30 mol %, between about 20 mol % and about 35 mol %, between about 20 mol % and about 40 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 21.0 mol %, 21.2 mol %, 21.4 mol %, 21.6 mol %, 21.8 mol %, 22 mol %, 25 mol %, 26 mol %, 26 mol %, 30 mol %, 35 mol %, or 40 mol %) of one or more compounds of the invention. In some embodiments, one or more compounds of the invention is present in an amount between about 10 mol % to about 80 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 10 mol % and about 40 mol %, between about 10 mol % and about 45 mol %, between about 10 mol % and about 50 mol %, between about 10 mol % and about 55 mol %, between about 10 mol % and about 60 mol %, between about 10 mol % and about 65 mol %, between about 10 mol % and about 70 mol %, between about 10 mol % and about 75 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 15 mol % and about 45 mol %, between about 15 mol % and about 50 mol %, between about 15 mol % and about 55 mol %, between about 15 mol % and about 60 mol %, between about 15 mol % and about 65 mol %, between about 15 mol % and about 70 mol %, between about 15 mol % and about 75 mol %, between about 15 mol % and about 80 mol %, between about 20 mol % and about 25 mol %, between about 20 mol % and about 30 mol %, between about 20 mol % and about 35 mol %, between about 20 mol % and about 40 mol %, between about 20 mol % and about 45 mol %, between about 20 mol % and about 50 mol %, between about 20 mol % and about 55 mol %, between about 20 mol % and about 60 mol %, between about 20 mol % and about 65 mol %, between about 20 mol % and about 70 mol %, between about 20 mol % and about 75 mol %, between about 20 mol % and about 80 mol %, between about 25 mol % and about 30 mol %, between about 25 mol % and about 35 mol %, between about 25 mol % and about 40 mol %, between about 25 mol % and about 45 mol %, between about 25 mol % and about 50 mol %, between about 25 mol % and about 55 mol %, between about 25 mol % and about 60 mol %, between about 25 mol % and about 65 mol %, between about 25 mol % and about 70 mol %, between about 25 mol % and about 75 mol %, between about 25 mol % and about 80 mol %, between about 30 mol % and about 35 mol %, between about 30 mol % and about 40 mol %, between about 30 mol % and about 45 mol %, between about 30 mol % and about 50 mol %, between about 30 mol % and about 55 mol %, between about 30 mol % and about 60 mol %, between about 30 mol % and about 65 mol %, between about 30 mol % and about 70 mol %, between about 30 mol % and about 75 mol %, between about 30 mol % and about 80 mol %, between about 35 mol % and about 40 mol %, between about 35 mol % and about 45 mol %, between about 35 mol % and about 50 mol %, between about 35 mol % and about 55 mol %, between about 35 mol % and about 60 mol %, between about 35 mol % and about 65 mol %, between about 35 mol % and about 70 mol %, between about 35 mol % and about 75 mol %, or between about 35 mol % and about 80 mol %, between about 40 mol % and about 45 mol %, between about 40 mol % and about 50 mol %, between about 40 mol % and about 55 mol %, between about 40 mol % and about 60 mol %, between about 40 mol % and about 65 mol %, between about 40 mol % and about 70 mol %, between about 40 mol % and about 75 mol %, between about 40 mol % and about 80 mol %, between about 45 mol % and about 50 mol %, between about 45 mol % and about 55 mol %, between about 45 mol % and about 60 mol %, between about 45 mol % and about 65 mol %, between about 45 mol % and about 70 mol %, between about 45 mol % and about 75 mol %, or between about 45 mol % and about 80 mol %, between about 50 mol % and about 55 mol %, between about 50 mol % and about 60 mol %, between about 50 mol % and about 65 mol %, between about 50 mol % and about 70 mol %, between about 50 mol % and about 75 mol %, or between about 50 mol % and about 80 mol % (e.g., about 21.0 mol %, 21.2 mol %, 21.4 mol %, 21.6 mol %, 21.8 mol %, 22 mol %, 25 mol %, 26 mol %, 26 mol %, 30 mol %, 35 mol %, 40 mol %, 45 mol %, 48 mol %, 49 mol %, 50 mol %, 55 mol %, 60 mol %, 65 mol %, 70 mol %, or 75 mol %) of one or more compounds of the invention.

In some embodiments, one or more cationic lipids is present in an amount between about 10 mol % to about 40 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 20 mol % and about 25 mol %, between about 20 mol % and about 30 mol %, between about 20 mol % and about 35 mol %, between about 20 mol % and about 40 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 25.1 mol %, 25.2 mol %, 25.3 mol %, 25.4 mol %, 25.5 mol %, 25.6 mol %, 25.7 mol %, 25.8 mol %, 25.9 mol %, 26.0 mol %, 26.2 mol %, 26.4 mol %, 26.6 mol %, 26.8 mol %, or 27 mol %) of one or more cationic lipids (e.g., DODMA or any described herein, such as in Table 1).

In some embodiments, one or more PEG-lipid conjugates is present in an amount between about 1 mol % to about 20 mol %, e.g., between about 1 mol % and about 5 mol %, between about 1 mol % and about 10 mol %, between about 1 mol % and about 15 mol %, between about 2 mol % and about 5 mol %, between about 2 mol % and about 10 mol %, between about 2 mol % and about 15 mol %, between about 2 mol % and about 20 mol %, between about 5 mol % and about 10 mol %, between about 5 mol % and about 15 mol %, between about 5 mol % and about 20 mol %, between about 10 mol % and about 15 mol %, between about 10 mol % and about 20 mol %, between about 15 mol % and about 20 mol % (e.g., about 2.5 mol %, 2.6 mol %, 2.7 mol %, 2.8 mol %, 2.9 mol %, 3 mol %, 3.5 mol %, 4 mol %, 4.3 mol %, 4.5 mol %, 4.7 mol %, 5 mol %, 5.3 mol %, 5.5 mol %, 5.7 mol %, 6 mol %, 6.5 mol %, 6.7 mol %, 7 mol %, 7.5 mol %, 8 mol %, 8.5 mol %, or 9 mol %) of one or more PEG-lipid conjugates (e.g., PEG-DSPE, PEG-DMPE, and/or any described herein).

In some embodiments, one or more neutral lipids is present in an amount between about 5 mol % to about 20 mol %, e.g., between about 5 mol % and about 10 mol %, between about 5 mol % and about 15 mol %, between about 5 mol % and about 20 mol %, between about 7 mol % and about 10 mol %, between about 7 mol % and about 15 mol %, between about 7 mol % and about 20 mol %, between about 10 mol % and about 15 mol %, between about 10 mol % and about 20 mol %, between about 15 mol % and about 20 mol % (e.g., about 13.0 mol %, 13.2 mol %, 13.4 mol %, 13.6 mol %, 13.8 mol %, 14 mol %, 14.1 mol %, 14.3 mol %, 14.5 mol %, 14.7 mol %, or 14.9 mol %) of one or more neutral lipids (e.g., DSPC or any described herein).

In some embodiments, one or more sterol derivatives is present in an amount between about 20 mol % to about 40 mol %, e.g., between about 20 mol % and about 25 mol %, between about 20 mol % and about 30 mol %, between about 20 mol % and about 35 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 28.4 mol %, 28.6 mol %, 28.8 mol %, 29.0 mol %, 30 mol %, 31 mol %, 32 mol %, 33 mol %, 33.2 mol %, 33.4 mol %, 33.6 mol %, 33.8 mol %, 34 mol %, 34.4 mol %, 34.7 mol %, or 34.9 mol %) of one or more sterol derivatives (e.g., cholesterol or any described herein).

In some embodiments, the formulation includes one or more lipid particles comprising one or more RNA-binding agents and one or more transfection lipids, where the one or more RNA-binding agents include from about 10 mol % to about 40 mol % of one or more cationic lipids or one or more compounds of the invention and from about 0.5 mol % to about 10 mol % of one or more PEG-lipid; and where the one or more transfection lipids include from about 10 mol % to about 40 mol % of one or more compounds of the invention, from about 5 mol % to about 20 mol % of one or more neutral lipids, from about 0.5 mol % to about 10 mol % of one or more PEG-lipid conjugates, and from about 20 mol % to about 40 mol % of one or more sterol derivatives. Additional formulation and percentages are as described herein.

In some embodiments, the formulation further includes a polyanionic payload or an antisense payload. In some embodiments, the polyanionic payload is an RNAi agent (e.g., dsRNA, siRNA, miRNA, shRNA, ptgsRNA, or DsiRNA, e.g., DsiRNA). In some embodiments, the RNAi agent has a length of 10 to 40 nucleotides, e.g., length of 10 to 15 nucleotides, 10 to 20 nucleotides, 10 to 25 nucleotides, 10 to 30 nucleotides, 10 to 35 nucleotides, 15 to 20 nucleotides, 15 to 25 nucleotides, 15 to 30 nucleotides, 15 to 35 nucleotides, 15 to 40 nucleotides, 16 to 20 nucleotides, 16 to 25 nucleotides, 16 to 30 nucleotides, 16 to 35 nucleotides, 16 to 40 nucleotides, 20 to 25 nucleotides, 18 to 20 nucleotides, 18 to 25 nucleotides, 18 to 30 nucleotides, 18 to 35 nucleotides, 18 to 40 nucleotides, 19 to 20 nucleotides, 19 to 25 nucleotides, 19 to 30 nucleotides, 19 to 35 nucleotides, 19 to 40 nucleotides, 20 to 30 nucleotides, 20 to 35 nucleotides, 20 to 40 nucleotides, 25 to 30 nucleotides, 25 to 35 nucleotides, 25 to 40 nucleotides, 30 to 35 nucleotides, 30 to 40 nucleotides, or 35 to 40 nucleotides, e.g., a length of 25 to 35 nucleotides, e.g., a length of 16 to 30 nucleotides, e.g., a length of 19 to 29 nucleotides. In some embodiments, the antisense payload has a length of 8 to 50 nucleotides (e.g., a length of 8 to 10 nucleotides, 8 to 15 nucleotides, 8 to 15 nucleotides, 8 to 20 nucleotides, 8 to 25 nucleotides, 8 to 30 nucleotides, 8 to 35 nucleotides, 8 to 40 nucleotides, or 8 to 45 nucleotides), e.g., a length of 14 to 35 nucleotides (e.g., a length of 14 to 15 nucleotides, 14 to 20 nucleotides, 14 to 25 nucleotides, or 14 to 30 nucleotides), e.g., a length of 17 to 24 nucleotides, e.g., a length of 17 to 20 nucleotides.

In some embodiments, the formulation includes from about 1:10 (w/w) to about 1:100 (w/w) ratio of the poly anionic payload to the total lipid present in the formulation, e.g., from about 1:10 (w/w) to about 1:15 (w/w) ratio, from about 1:10 (w/w) to about 1:20 (w/w) ratio, from about 1:10 (w/w) to about 1:40 (w/w) ratio, from about 1:10 (w/w) to about 1:50 (w/w) ratio, from about 1:10 (w/w) to about 1:60 (w/w) ratio, from about 1:10 (w/w) to about 1:70 (w/w) ratio, from about 1:10 (w/w) to about 1:80 (w/w) ratio, from about 1:10 (w/w) to about 1:90 (w/w) ratio, from about 1:10 (w/w) to about 1:95 (w/w) ratio, from about 1:20 (w/w) to about 1:40 (w/w) ratio, from about 1:20 (w/w) to about 1:50 (w/w) ratio, from about 1:20 (w/w) to about 1:60 (w/w) ratio, from about 1:20 (w/w) to about 1:70 (w/w) ratio, from about 1:20 (w/w) to about 1:80 (w/w) ratio, from about 1:20 (w/w) to about 1:90 (w/w) ratio, from about 1:20 (w/w) to about 1:95 (w/w) ratio, from about 1:20 (w/w) to about 1:100 (w/w) ratio, from about 1:40 (w/w) to about 1:50 (w/w) ratio, from about 1:40 (w/w) to about 1:60 (w/w) ratio, from about 1:40 (w/w) to about 1:70 (w/w) ratio, from about 1:40 (w/w) to about 1:80 (w/w) ratio, from about 1:40 (w/w) to about 1:90 (w/w) ratio, from about 1:40 (w/w) to about 1:95 (w/w) ratio, from about 1:40 (w/w) to about 1:100 (w/w) ratio, from about 1:50 (w/w) to about 1:60 (w/w) ratio, from about 1:50 (w/w) to about 1:70 (w/w) ratio, from about 1:50 (w/w) to about 1:80 (w/w) ratio, from about 1:50 (w/w) to about 1:90 (w/w) ratio, from about 1:50 (w/w) to about 1:95 (w/w) ratio, from about 1:50 (w/w) to about 1:100 (w/w) ratio, from about 1:60 (w/w) to about 1:70 (w/w) ratio, from about 1:60 (w/w) to about 1:80 (w/w) ratio, from about 1:60 (w/w) to about 1:90 (w/w) ratio, from about 1:60 (w/w) to about 1:95 (w/w) ratio, from about 1:60 (w/w) to about 1:100 (w/w) ratio, from about 1:80 (w/w) to about 1:90 (w/w) ratio, from about 1:80 (w/w) to about 1:95 (w/w) ratio, or from about 1:80 (w/w) to about 1:100 (w/w) ratio of the polyanionic payload to the total lipid present in the formulation.

In some embodiments, the formulation includes a liposome (e.g., a lipid nanoparticle), a lipoplex, or a micelle.

In one aspect, the invention features a pharmaceutical composition including any compound described herein (e.g., one or more compound provided in Table 1), or a pharmaceutically acceptable salt thereof, or any formulation described herein; and a pharmaceutically acceptable excipient.

In another aspect, the invention features a method of treating or prophylactically treating a disease in a subject, the method including administering to the subject any compound described herein (e.g., one or more compound provided in Table 1), or a pharmaceutically acceptable salt thereof, any formulation described herein, or any composition described in an amount sufficient to treat the disease (e.g., liver cancer (e.g., hepatocellular carcinoma, hepatoblastoma, cholangiocarcinoma, angiosarcoma, or hemangiosarcoma), lung cancer (e.g., small cell lung cancer, non small cell lung cancer), prostate cancer, or neuroblastoma). The invention further features a method of treating or prophylactically treating neoplastic diseases and associated complications including, but not limited to, carcinomas (e.g., lung, breast, pancreatic, colon, hepatocellular, renal, female genital tract, prostate, squamous cell, carcinoma in situ), lymphoma (e.g., histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g., small cell lung cancer, non small cell lung cancer), breast, colon, bladder, prostate, gastrointestinal tract, endometrium, fallopian tube, testes and ovary, gastrointestinal stromal tumors (GISTs), prostate tumors, mast cell tumors (including canine mast cell tumors), acute myeloid myelofibrosis, leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g., sarcomas of neuroectodermal origin or leiomyosarcoma), metastasis of tumors to other tissues, and chemotherapy-induced hypoxia.

In another aspect, the invention features a method of modulating the expression of a target nucleic acid in a subject, the method including administering any compound described herein (e.g., one or more compound provided in Table 1), or a pharmaceutically acceptable salt thereof, any formulation described herein, or any composition described in an amount sufficient to reduce the expression of the target gene (e.g., any described herein, e.g., one or more target genes selected from the group consisting of ABL1, AR, β-Catenin (CTNNB1), BCL1, BCL2, BCL6, CBFA2, CBL, CSF1R, ERBA1, ERBA2, ERBB1, ERBB2, ERBB3, ERBB4, ETS1, ETS2, ETV6, FGR, FOS, FYN, HCR, HRAS, JUN, KRAS, LCK, LYN, MET, MDM2, MLL1, MLL2, MLL3, MYB, MYC, MYCL1, MYCN, NRAS, PIM1, PML, RET, SRC, TAL1, TAL2, TCL3, TCL5, YES, BRCA1, BRCA2, MADH4, MCC, NF1, NF2, RB1, TP53, WT1, ApoB100, CSN5, CDK6, ITGB1, TGFβ1, Cyclin D1, hepcidin, PCSK9, TTR, PLK1, and KIF1-binding protein) in the subject (e.g., where the method includes reducing the expression of the target gene in the subject).

In another embodiment, the invention features the administration of a dosage of the poly anionic payload or antisense payload of the invention to a subject one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month). A subject may receive dosages of the polyanionic payload or antisense payload in the range of about 0.0001 to about 10 mg/kg, e.g., about 0.0001 to about 1 mg/kg, about 0.0001 to about 5 mg/kg, about 0.001 to about 1 mg/kg, about 0.001 to about 5 mg/kg, about 0.001 to about 10 mg/kg, about 0.01 to about 1 mg/kg, about 0.01 to about 5 mg/kg, about 0.01 to about 10 mg/kg, about 1 to about 5 mg/kg, or about 1 to about 10 mg/kg, in any dosage regimen (e.g., one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month)).

In some embodiments, the invention features the administration of a formulation of the invention to a subject one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month). A subject may receive dosages of the formulation in the range of about 0.001 to about 200 mg/kg, e.g., about 0.001 to about 1 mg/kg, about 0.001 to about 10 mg/kg, about 0.001 to about 20 mg/kg, about 0.001 to about 50 mg/kg, about 0.001 to about 100 mg/kg, about 0.01 to about 1 mg/kg, about 0.01 to about 10 mg/kg, about 0.01 to about 20 mg/kg, about 0.01 to about 50 mg/kg, about 0.01 to about 100 mg/kg, about 0.01 to about 200 mg/kg, about 0.1 to about 1 mg/kg, about 0.1 to about 10 mg/kg, about 0.1 to about 20 mg/kg, about 0.1 to about 50 mg/kg, about 0.1 to about 100 mg/kg, about 0.1 to about 200 mg/kg, about 1 to about 10 mg/kg, about 1 to about 20 mg/kg, about 1 to about 50 mg/kg, about 1 to about 100 mg/kg, about 1 to about 200 mg/kg, about 10 to about 20 mg/kg, about 10 to about 50 mg/kg, about 10 to about 100 mg/kg, about 10 to about 200 mg/kg, about 20 to about 50 mg/kg, about 20 to about 100 mg/kg, or about 20 to about 200 mg/kg, in any dosage regimen (e.g., one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month)).

In another aspect, the invention features a method of delivering a polyanionic payload or antisense payload to a specific type of tissue. Examples of specific types of tissues to which the payload may be delivered to include, but are not limited to, liver, pancreas, lung, prostate, kidney, bone marrow, spleen, thymus, lymph node, brain, spinal cord, heart, skeletal muscle, skin, oral mucosa, esophagus, stomach, ileum, small intestine, colon, bladder, cervix, ovary, testis, mammary gland, adrenal gland, adipose tissue (white and/or brown), blood (e.g., hematopoietic cells, such as human hematopoietic progenitor cells, human hematopoietic stem cells, CD34+ cells, CD4+ cells), lymphocytes, and other blood lineage cells.

In any of the above aspects, the compounds of the invention includes two unsaturated lipid tail groups (e.g., each $R^1$ and $R^2$ is, independently, optionally substituted $C_{11-24}$ alkenyl, optionally substituted $C_{11-24}$ alkynyl, optionally substituted $C_{11-24}$ heteroalkenyl, or optionally substituted $C_{11-24}$ heteroalkynyl).

In any of the above aspects, the compounds of the invention include lipid tail groups, where these groups do not include an oxygen adjacent to —CHR³R⁴ (e.g., each $R^1$ and $R^2$ is, independently, optionally substituted $C_{11-24}$ alkyl, optionally substituted $C_{11-24}$ alkenyl, or optionally substituted $C_{11-24}$ alkynyl).

In any of the above aspects, the compounds of the invention include lipid tail groups, where these groups do not include one or more biodegradable groups (e.g., one or more ester groups).

In any of the above aspects, the compounds of the invention includes two lipid tail groups having more than 11, 12, 13, 14, 15, 16, or 18 carbons (e.g., each $R^1$ and $R^2$ is, independently, optionally substituted $C_{17-24}$ alkenyl, optionally substituted $C_{15-24}$ alkynyl, optionally substituted $C_{15-24}$ heteroalkenyl, or optionally substituted $C_{15-24}$ heteroalkynyl; each $R^1$ and $R^2$ is, independently, optionally substituted $C_{16-24}$ alkenyl, optionally substituted $C_{16-24}$ alkynyl, optionally substituted $C_{16-24}$ heteroalkenyl, or optionally substituted $C_{16-24}$ heteroalkynyl; each $R^1$ and $R^2$ is, independently, optionally substituted $C_{17-24}$ alkenyl, optionally substituted $C_{17-24}$ alkynyl, optionally substituted $C_{17-24}$ heteroalkenyl, or optionally substituted $C_{17-24}$ heteroalkynyl; or each $R^1$ and $R^2$ is, independently, optionally substituted $C_{18-24}$ alkenyl, optionally substituted $C_{18-24}$ alkynyl, optionally substituted $C_{18-24}$ heteroalkenyl, or optionally substituted $C_{18-24}$ heteroalkynyl).

In any of the above aspects, the compounds of the invention do not contain a urea group (e.g., neither $R^3$ nor $R^4$ is an optionally substituted amide). In some embodiments, the compounds do not contain a carbamyl group. In some embodiments, the compounds do not contain more than one primary amine group (e.g., do not contain two primary amine groups or do not contain any primary amine groups in one or more of $R^1$-$R^6$, e.g., in either $R^3$ or $R^4$). In particular embodiments, the compounds include only one primary amine or no primary amines (e.g., only one primary amine or no primary amines are present in one or more of $R^1$-$R^6$, e.g., in either $R^3$ or $R^4$).

In any of the above aspects, the compounds of the invention do not contain a hydroxy group (e.g., neither $R^1$ nor $R^2$ is substituted with one, two, or three hydroxy groups; or neither $R^3$ nor $R^4$ is substituted with one, two, or three hydroxy groups). In some embodiments, when $R^1$ or $R^2$ is a saturated $C_{11-24}$ alkyl group (e.g., a saturated $C_{15}$ alkyl, a saturated $C_{16}$ alkyl, a saturated $C_{17}$ alkyl, or a saturated $C_{18}$ alkyl), $R^1$ and/or $R^2$ is not substituted with one, two, or three hydroxy groups. In some embodiments, when $R^1$ or $R^2$ is a saturated $C_{11-24}$ alkyl group (e.g., a saturated $C_{15}$ alkyl, a saturated $C_{16}$ alkyl, a saturated $C_{17}$ alkyl, or a saturated $C_{18}$ alkyl), $R^3$ and/or $R^4$ is not substituted with one, two, or three hydroxy groups.

In any of the above aspects, the compounds of the invention include no more than two amide groups (e.g., no more than two or one amide groups in the head group of the compound). In other embodiments, the compounds include zero, one, or two amide groups in one or more of $R^1$-$R^6$ (e.g., zero, one, or two amide groups in $R^3$ or $R^4$). In yet other embodiments, the compounds can include one, and only one, amide group (e.g., can include one, and only one, amide groups in $R^3$ or $R^4$). In further embodiments, the compounds include one, and only, amide group or no amide groups (e.g., include one, and only one, amide group or no amide groups in $R^3$ or $R^4$).

In any of the above aspects, the compounds of the invention exclude N-(4-N',N'-dimethylamino)butanoyl-(6Z, 9Z,28Z,31Z)-heptatriaconta-6,9,28,31-tetraen-19-amine or N-(3-N',N'-dimethylamino)propanoyl-(6Z,9Z,28Z,31Z)-heptatriaconta-6,9,28,31-tetraen-19-amine, or salts thereof. In some embodiments, the compounds of the invention exclude N-methyl-N-(4-N',N'-dimethylamino)butanoyl-(6Z, 9Z,28Z,31Z)-heptatriaconta-6,9,28,31-tetraen-19-amine or N-methyl-N-(3-N',N'-dimethylamino)propanoyl-(6Z,9Z, 28Z,31Z)-heptatriaconta-6,9,28,31-tetraen-19-amine, or salts thereof.

In any of the above aspects, the compounds of the invention exclude N-(4-N',N'-dimethylamino)butanoyl-(6Z, 9Z,28Z)-heptatriaconta-6,9,28-trien-19-amine, N-methyl-N-(4-N',N'-dimethylamino)butanoyl-(6Z,9Z,28Z)-heptatriaconta-6,9,28-trien-19-amine, N-(4-N',N'-dimethylamino) butanoyl-(6Z,9Z,28Z,31Z,34Z)-heptatriaconta-6,9,28,31, 34-pentaen-19-amine, N-methyl-N-(4-N',N'-dimethylamino)butanoyl-(6Z,9Z,28Z,31Z,34Z)-heptatriaconta-6,9,28,31,34-pentaen-19-amine, N-(3-N',N'-dimethylamino)propanoyl-(6Z,9Z,28Z)-heptatriaconta-6,9, 28-trien-19-amine, N-methyl-N-(3-N',N'-dimethylamino) propanoyl-(6Z,9Z,28Z)-heptatriaconta-6,9,28-trien-19-amine, N-(3-N',N'-dimethylamino)propanoyl-(6Z,9Z,28Z, 31Z,34Z)-heptatriaconta-6,9,28,31,34-pentaen-19-amine, N-methyl-N-(3-N',N'-dimethylamino)propanoyl-(6Z,9Z, 28Z,31Z,34Z)-heptatriaconta-6,9,28,31,34-pentaen-19-amine, or salts thereof.

In any of the above aspects, the compounds of the invention exclude di((Z)-non-2-en-1-yl) 9-((3-(dimethylamino)propanoyl)amino)heptadecanedioate, di((Z)-non-2-en-1-yl) 9-((4-(dimethylamino)butanoyl)amino)heptadecanedioate, di((Z)-non-2-en-1-yl) 9-((5-(dimethylamino) pentanoyl)amino)heptadecanedioate, or salts thereof.

In any of the above aspects, the compounds of the invention has a pKa value less than 6.2 and more than 6.5 (e.g., a pKa value between 4.0 and 6.2, such as between 4.0 and 5.2, between 4.0 and 5.6, or between 4.0 and 5.8; or between 6.5 and 8.5, e.g., between 6.5 and 7.0, between 6.5 and 7.5, or between 6.5 and 8.0). In particular embodiments, the pKa value is between about 5.0 and about 6.0 (e.g., between 5.0 and 5.5, between 5.0 and 5.6, between 5.0 and 5.7, between 5.0 and 5.8, between 5.0 and 5.9, between 5.0 and 6.0, between 5.2 and 5.5, between 5.2 and 5.6, between 5.2 and 5.7, between 5.2 and 5.8, between 5.2 and 5.9, between 5.2 and 6.0, between 5.4 and 5.5, between 5.4 and 5.6, between 5.4 and 5.7, between 5.4 and 5.8, between 5.4 and 5.9, between 5.4 and 6.0, between 5.6 and 5.7, between 5.6 and 5.8, between 5.6 and 5.9, or between 5.6 and 6.0). The pKa value can be determined by any useful method, e.g., measuring fluorescence of 2-(p-toluidino)-6-napthalene sulfonic acid (TNS), zeta potential measurements, etc. In particular embodiments, the pKa value is the ratio of the concentration of charged cationic lipid and the concentration of uncharged lipid (e.g., as measured by in situ TNS fluorescence titration, where pKa is defined as the pH at half-maximal fluorescence intensity).

Definitions

As used herein, the term "about" means±10% of the recited value.

By "alkenyl" is meant a monovalent straight or branched chain group of, unless otherwise specified, from 2 to 24 carbon atoms containing one or more carbon-carbon double bonds. Alkenyl groups are exemplified by ethenyl, 1-propenyl, 2-propenyl, 2-methyl-1-propenyl, 1-butenyl, 2-butenyl, oleyl, linoleyl, linolenyl, and the like. The term "$C_{x-y}$ alkenyl" represents alkenyl groups having between x and y carbons. Exemplary values for x are 2, 3, 4, 5, and 11; for y are 3, 4, 5, 6, and 24; and for x to y are 2 to 10, 2 to 9, 2 to 8, 2 to 7, 2 to 6, 2 to 5, 2 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20. In some embodiments, the alkenyl can be further substituted with 1, 2, 3, or 4 substituent groups as defined herein for an alkyl group.

By "alkyl" is meant a monovalent straight or branched saturated group of, unless otherwise specified, 1 to 24 carbon atoms. Alkyl groups are exemplified by methyl, ethyl, n-propyl, iso-propyl, n-butyl, sec-butyl, iso-butyl, tert-butyl, neopentyl, lauryl, myristyl, palmityl, stearyl, and the like, and may be optionally substituted with one, two, three, or, in the case of alkyl groups of two carbons or more, four substituents independently selected from the group consisting of: (1) alkoxy; (2) amino, as defined herein; (3) halo, such as F, Cl, Br, or I; (4) (heterocyclyl)oxy; (5) heterocyclyl; (6) alkyl; (7) alkenyl; (9) alkynyl; (10) cycloalkyl; (11) hydroxy; (12) nitro; or (13) oxo (e.g., carboxyaldehyde or acyl). In some embodiments, each of these groups can be further substituted as described herein. The term "$C_{x-y}$ alkyl" represents alkyl groups having between x and y carbons. Exemplary values for x are 1, 2, 3, 4, 5, and 11; for y are 2, 3, 4, 5, 6, and 24; and for x to y are 1 to 10, 1 to 9, 1 to 8, 1 to 7, 1 to 6, 1 to 5, 1 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20.

The term "alkylene" and the prefix "alk-," as used herein, represent a polyvalent (e.g., divalent) hydrocarbon group derived from a straight or branched chain hydrocarbon by the removal of two hydrogen atoms. Alkylene groups are exemplified by methylene, ethylene, isopropylene, and the like. The term "$C_{x-y}$ alkylene" represent alkylene groups having between x and y carbons. Exemplary values for x are 1, 2, 3, 4, and 5, and exemplary values for y are 2, 3, 4, 5, and 6. In some embodiments, the alkylene can be further substituted with 1, 2, 3, or 4 substituent groups as defined herein for an alkyl group.

By "alkynyl" is meant a monovalent straight or branched chain group of, unless otherwise specified, from 2 to 24 carbon atoms containing one or more carbon-carbon triple bonds. Alkynyl groups are exemplified by ethynyl, 1-propynyl, and the like. The term "$C_{x-y}$ alkynyl" represents alkynyl groups having between x and y carbons. Exemplary values for x are 2, 3, 4, 5, and 11; for y are 3, 4, 5, 6, and 24; and for x to y are 2 to 10, 2 to 9, 2 to 8, 2 to 7, 2 to 6, 2 to 5, 2 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20. In some embodiments, the alkynyl can be further substituted with 1, 2, 3, or 4 substituent groups as defined herein for an alkyl group.

By "amide" is meant an amine group, as defined herein, attached to the parent molecular group through a carbonyl group.

By "amino," as used herein, is meant $-N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. In a preferred embodiment, amino is $-NH_2$, or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl. By "primary amine" is meant a group having the structure $-NH_2$.

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group.

As used herein, the term "carbamyl" refers to a carbamate group having the structure $-NR^{N1}C(=O)OR$ or $-OC(=O)N(R^{N1})_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

By "cycloalkyl" is meant a monovalent saturated or partially unsaturated 3- to 10-membered monocyclic or polycyclic (e.g., bicyclic or tricyclic) hydrocarbon ring system. Examples include cyclopropyl, cyclobutyl, cyclopentyl, cyclohexyl, and cycloheptyl.

The term "halo," as used herein, represents a halogen selected from bromine, chlorine, iodine, or fluorine.

By "heteroalkenyl" is meant an alkenyl group, as defined herein, in which one or more of the constituent carbon atoms have each been replaced by O, N, or S. Exemplary heteroalkenyl groups include alkenyl groups, as described herein, substituted with an oxo group and/or attached to the parent molecular group through an oxygen atom. In some embodiments, the heteroalkenyl group can be further substituted with 1, 2, 3, or 4 substituent groups as described herein for alkyl groups.

By "heteroalkyl" is meant an alkyl group, as defined herein, in which one or more of the constituent carbon atoms have each been replaced by O, N, or S. Exemplary heteroalkyl groups include alkyl groups, as described herein, substituted with an oxo group and/or attached to the parent molecular group through an oxygen atom. In some embodiments, the heteroalkyl group can be further substituted with 1, 2, 3, or 4 substituent groups as described herein for alkyl groups.

The term "heteroalkylene," as used herein, refers to an alkylene group, as defined herein, in which 1 or 2 of the constituent carbon atoms have each been replaced by O, N, or S. In some embodiments, the heteroalkylene group can be further substituted with 1, 2, 3, or 4 substituent groups as described herein for alkylene groups. The term "$C_{x-y}$ heteroalkylene" represent heteroalkylene groups having between x and y carbons. Exemplary values for x are 1, 2, 3, 4, 5, and 11; for y are 2, 3, 4, 5, 6, and 24; and for x to y are 1 to 10, 1 to 9, 1 to 8, 1 to 7, 1 to 6, 1 to 5, 1 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20.

By "heteroalkynyl" is meant an alkynyl group, as defined herein, in which one or more of the constituent carbon atoms have each been replaced by O, N, or S. Exemplary heteroalkynyl groups include alkynyl groups, as described herein, substituted with an oxo group and/or attached to the parent molecular group through an oxygen atom. In some embodiments, the heteroalkynyl group can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. In some embodiment, the heteroaryl is substituted with 1, 2, 3, or 4 substituents groups as defined for a heterocyclyl group.

The term "heterocyclyl," as used herein represents a 3-, 4-, 5-, 6-, 7-, or 8-membered ring, unless otherwise specified, containing one, two, three, or four heteroatoms independently selected from the group consisting of nitrogen, oxygen, and sulfur. The heterocyclyl may be saturated or unsaturated and contain between 0 and 3 unsaturated bonds. For example, the 5-membered ring has zero to two double bonds, and the 6- and 7-membered rings have zero to three double bonds. Certain heterocyclyl groups include from 2 to 9 carbon atoms, e.g., from 3 to 7 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. Examples of heterocyclic groups include aziridinyl, azetidinyl, pyrrolinyl, pyrrolyl, pyrrolidinyl, pyrazolyl, pyrazolinyl, pyrazolidinyl, imidazolyl, imidazolinyl, imidazolidinyl, pyridyl, pyrimidinyl, piperidinyl, azepanyl, pyrazinyl, piperazinyl, diazepanyl, morpholinyl, tetrahydrofuranyl, dihydrofuranyl, and the like.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydroxy," as used herein, represents an —OH group.

By "linker" is meant an optionally substituted polyvalent (e.g., divalent) group containing one or more atoms. Examples of linkers include optionally substituted alkylene and heteroalkylene groups, as described herein.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "oxo" as used herein, represents =O.

The term "urea" refers to a group having the structure $NR^{N1}C(=O)NR^{N1}$, where the meaning of each $R^{N1}$ is found in the definition of "amino" provided herein.

By "amount sufficient" of an agent is meant the amount of the agent sufficient to effect beneficial or desired results, such as clinical results, and, as such, an amount sufficient depends upon the context in which it is applied. For example, in the context of administering a formulation that reduces the expression level of a target gene, the amount sufficient of the formulation is an amount sufficient to achieve a reduction in the expression level of the target gene as compared to the response obtained without administration of the formulation.

By "anionic lipid" is meant any lipid molecule that has a net negative charge at physiological pH.

As used herein, the term "antisense compound" or "antisense payload" encompasses, inter alio, single-stranded antisense oligonucleotides (DNA, DNA-like, RNA, RNA-like) or certain double-stranded or self-hybridizing constructs comprising an antisense orientation oligonucleotide, antisense PNAs, ribozymes and external guide sequences (sequences that recruit RNase P, as described, e.g., in Guerrier-Takada et al., *Proc. Natl. Acad. Sci. USA* 94:8468, 1997). Antisense compounds can exert their effect by a variety of means. One such means is the antisense-mediated direction of an endogenous nuclease, such as RNase H in eukaryotes or RNase P in prokaryotes (Chiang et al., *J. Biol. Chem.* 1266:18162, 1991; Forster et al., *Science*, 249:783, 1990).

By "cationic lipid" is meant any lipid molecule that has a net positive charge at physiological pH. Exemplary cationic lipids include any described herein, e.g., in Table 1.

By "Dicer-substrate RNA" or "DsiRNA" is meant a class of 25-35 (e.g., 25-27, such as 27) nucleotide double-stranded molecules that are capable of gene silencing. Due to its longer length compared to other RNAi agents, DsiRNA are likely substrates of Dicer.

By "double-stranded molecule" is meant a double-stranded RNA:RNA or RNA:DNA molecule that can be used to silence a gene product through RNA interference.

By "expression" is meant the detection of a gene or polypeptide by methods known in the art. For example, DNA expression is often detected by Southern blotting or polymerase chain reaction (PCR), and RNA expression is often detected by Northern blotting, RT-PCR, gene array technology, or RNAse protection assays. Methods to measure protein expression level generally include, but are not limited to, Western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), and flow cytometry, as well as assays based on a property of the protein including, but not limited to, enzymatic activity or interaction with other protein partners.

By "hybridize" is meant to pair to form a double-stranded molecule between sufficiently complementary polynucleotides, as defined herein, or portions thereof, under various conditions of stringency. (See, e.g., Wahl et al., *Methods Enzymol.* 152:399 (1987); Kimmel, *Methods Enzymol.* 152: 507 (1987)). For example, high stringency salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. High stringency temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 50° C. or 70° C. in 400 mM NaCl, 40 mM PIPES, and 1 mM EDTA, at pH 6.4, after hybridization for 12-16 hours, followed by washing. Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Useful variations on these conditions will be readily apparent to those skilled in the art. One such exemplary variation includes assessment of hybridization under conditions designed to mimic physiological intracellular conditions, wherein cations and anions are assorted in the following proportions: for cations, Sodium:Potassium:Calcium:Magnesium at 10:160:2:26; and for anions, Chloride:Bicarbonate:Phosphate:Sulfate:Gluconate at 3:10:100:20:65.

By "lipid vector" is meant a liposome, lipoplex, micelle, lipid nanoparticle, core-based particle, particle comprising an RNA binding agent-RNA aggregate which is combined with transfection lipid(s), or vesicle-based particle comprising one or more compounds of the invention.

By "microRNA" (miRNA) is meant a single-stranded RNA molecule that can be used to silence a gene product through RNA interference.

By "modulate" is meant that the expression of a gene, or level of an RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term modulate can include inhibition or gene silencing, and the level of expression of a gene or the level of an RNA molecule, or an equivalent thereof, is reduced by at least 10% (e.g., 15%, 20%, 25%, 30%, 35%, 40%, 50%, 60%, 70%, 80%, 85%, 90%, 95%, 97%, 98%, 99%, or 100%), as compared to a control.

By "neutral lipid" is meant any lipid molecule that exists either in an uncharged or neutral zwitterionic form at physiological pH.

By "polyanionic payload" is meant a chemical moiety comprising multiple negatively charged atoms that may be incorporated into a formulation. Examples of a polyanionic payload include nucleic acids, RNAi agents, siRNA, dsRNA, miRNA, shRNA, DsiRNA, and antisense payloads.

By "RNA-binding agent" is meant any agent or combination of agents capable of binding or hybridizing a nucleic acid, e.g., a nucleic acid payload of a therapeutic formulation. RNA-binding agents include any lipid described herein (e.g., one or more cationic lipids, combinations of one or more cationic lipids, such as those described herein or in Table 1, as well as combinations of one or more cationic lipids and any other lipid, such as neutral lipids or PEG-lipid conjugates). The RNA-binding agent can form any useful structure within a formulation, such as an internal aggregate.

By "RNAi agent" is meant any agent or compound that exerts a gene silencing effect by hybridizing a target nucleic acid. RNAi agents include any nucleic acid molecules that are capable of mediating sequence-specific RNAi (e.g., under stringent conditions), for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and Dicer-substrate RNA (DsiRNA).

By "short hairpin RNA" or "shRNA" is meant a sequence of RNA that makes a tight hairpin turn and is capable of gene silencing.

By "sense region" is meant a nucleotide sequence of a nucleic acid of the invention having sufficient complementarity to an antisense region of another nucleic acid. In addition, the sense region of a nucleic acid of the invention can include a nucleotide sequence having homology with a target gene nucleotide sequence. By "antisense region" is meant a nucleotide sequence of a nucleic acid of the invention having sufficient complementarity to a target gene nucleotide sequence.

By "silencing" or "gene silencing" is meant that the expression of a gene or the level of an RNA molecule that encodes one or more proteins is reduced in the presence of an RNAi agent below that observed under control conditions (e.g., in the absence of the RNAi agent or in the presence of an inactive or attenuated molecule such as an RNAi molecule with a scrambled sequence or with mismatches). Gene silencing may decrease gene product expression by 1%, 2%, 3%, 4%, 5%, 6%, 7%, 8%, 9%, 10%, 15%, 20%, 25%, 30%, 35%, 40%, 50%, 60%, 70%, 80%, 85%, 90%, 95%, 97%, 98%, 99%, or 100% (i.e., complete inhibition).

By "small inhibitory RNA," "short interfering RNA," or "siRNA" is meant a class of 10-40 (e.g., 15-25, such as 21) nucleotide double-stranded molecules that are capable of gene silencing. Most notably, siRNA are typically involved in the RNA interference (RNAi) pathway by which the siRNA interferes with the expression of a specific gene product.

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full-length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "sufficiently complementary" is meant a polynucleotide sequence that has the exact complementary polynucleotide sequence, as a target nucleic acid, or has a specified percentage or nucleotides that are the exact complement at the corresponding location within the target nucleic acid when the two sequences are optimally aligned. For example, a polynucleotide sequence that is "substantially complementary" to a target nucleic acid sequence has at least 50%, 60%, 70%, 75%, 80%, 85%, 90%, 95%, 96%, 97%, 98%, 99%, or 100% complementarity to the target nucleic acid sequence. For RNAi agents having a length between 10 to 40 nucleotides, sufficiently complementary sequences include those having one, two, three, four, or five non-complementary nucleotides. Indeed, in certain embodiments that include, e.g., DsiRNA agents, an active double-stranded RNAi agent can possess as few as 15 to 19 consecutive nucleotides of guide strand which are sufficiently complementary to a target nucleic acid, while there is no requirement for the remainder of the guide strand to possess any extent of complementarity with the target nucleic acid (though in certain embodiments, the remainder of the guide strand may partially or fully complementary with the nucleic acid (e.g., mRNA) that is targeted).

By "target nucleic acid" is meant any nucleic acid sequence whose expression or activity is to be modulated. The target nucleic acid can be DNA or RNA. In certain embodiments, the target nucleic acid is a target mRNA.

By "transfection lipid" is meant any lipid or combination of lipids capable of delivering a nucleic acid, e.g., a nucleic acid payload (optionally, the nucleic acid payload is in association with an RNA binding agent, e.g., one or more cationic lipids). Transfection lipids include any lipid described herein (e.g., one or more cationic lipids, combinations of one or more cationic lipids, such as those described herein or in Table 1, as well as combinations of one or more cationic lipids and any other lipid or agent, such as neutral lipids, anionic lipids, PEG-lipid conjugates, or sterol derivatives). The transfection lipid or combinations including such a transfection lipid can form any useful structure within a formulation, such as an external, aggregate surface.

By "pharmaceutical composition" is meant a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

By "pharmaceutically acceptable excipient" is meant any ingredient other than the compounds described herein (for example, a vehicle capable of suspending or dissolving the active compound) and having the properties of being non-toxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

By "pharmaceutically acceptable salt" is meant those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharm. Sci.* 66(1):1, 1977 and in *Pharmaceutical Salts: Properties, Selection, and Use*, P. H. Stahl and C. G. Wermuth (eds.), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, and the like.

By "subject" is meant either a human or non-human animal (e.g., a mammal)

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. By "treating cancer," "preventing cancer," or "inhibiting cancer" is meant causing a reduction in the size of a tumor or the number of cancer cells, slowing or inhibiting an increase in the size of a tumor or cancer cell proliferation, increasing the disease-free survival time between the disappearance of a tumor or other cancer and its reappearance, preventing or reducing the likelihood of an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay. Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after no less than 5, 10, 15, or 20 years. By "prophylactically treating" a disease or condition (e.g., cancer) in a subject is meant reducing the risk of developing (i.e., the incidence) of or reducing the severity of the disease or condition prior to the appearance of disease symptoms. The prophylactic treatment may completely prevent or reduce appears of the disease or a symptom thereof and/or may be therapeutic in terms of a partial or complete cure for a disease and/or adverse effect attributable to the disease. Prophylactic treatment may include reducing or preventing a disease or condition (e.g., preventing cancer) from occurring in an individual who may be predisposed to the disease but has not yet been diagnosed as having it.

DETAILED DESCRIPTION

Figure 1:
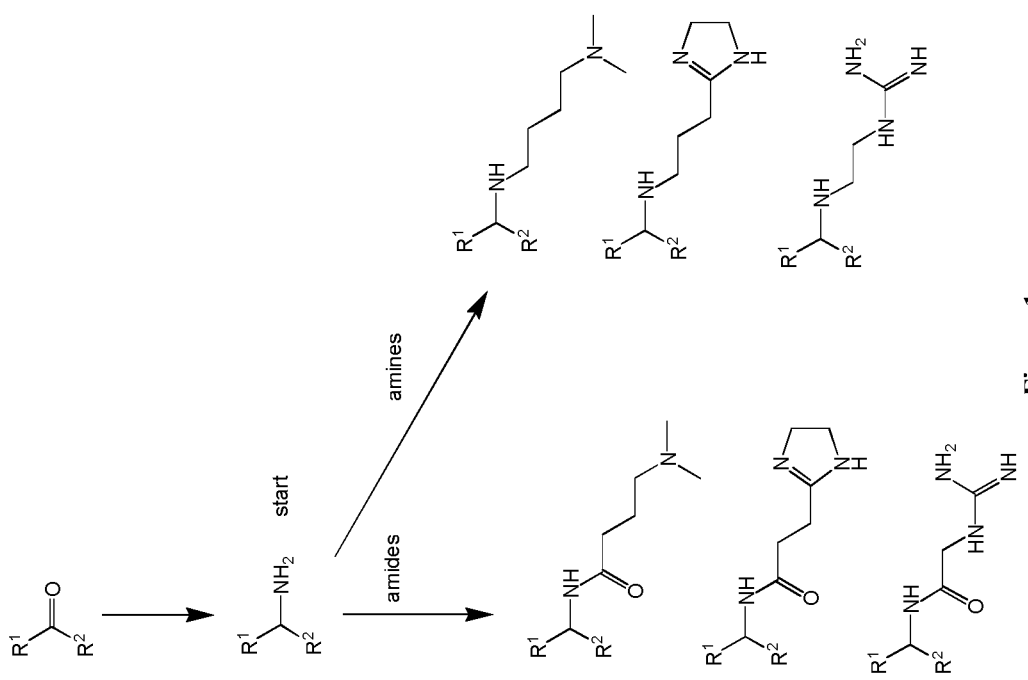
FIG. 1 shows exemplary embodiments of amino-amide (labeled "amide") and amino-amine (labeled "amine") compounds. For these compounds, $R^1$ and $R^2$ can be any tail group described herein, such as optionally substituted $C_{11-24}$ alkyl, alkenyl, alkynyl, heteroalkyl, heteroalkenyl, or heteroalkynyl.

We have now developed amino-amine and amino-amide cationic lipids that may be formulated into lipid particles. The formulations of the invention may be used for the delivery of a polyanionic payload (e.g., nucleic acid molecules or RNAi agents) to cells (e.g., in vitro or in vivo in a subject). The delivery of the polyanionic payload may achieve sequence-specific gene silencing in cells.

Amino-Amine and Amino-Amide Lipids

The compounds of the invention include any compound of formula (I). In particular embodiments, the compound is selected from Table 1.

TABLE 1

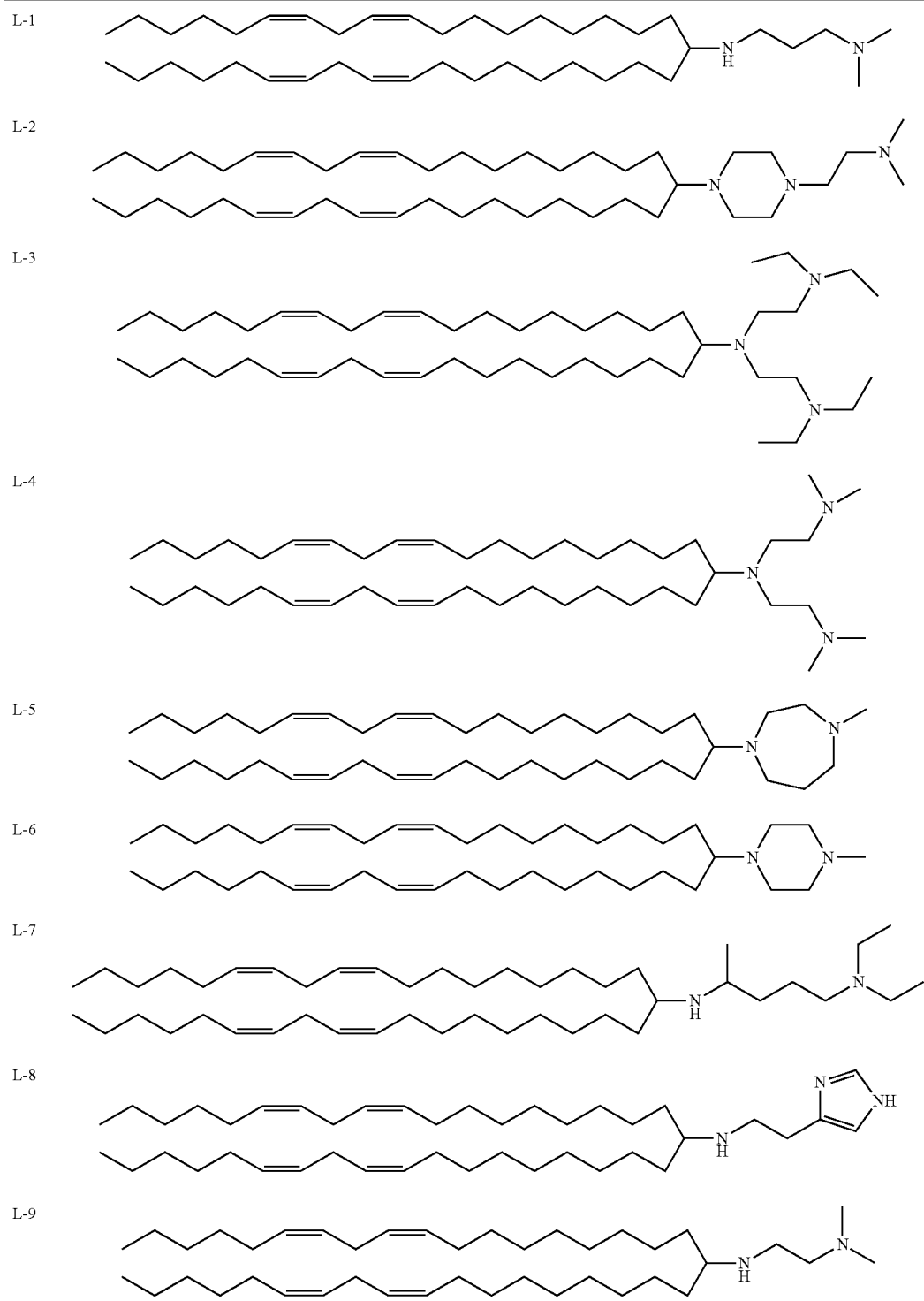

TABLE 1-continued
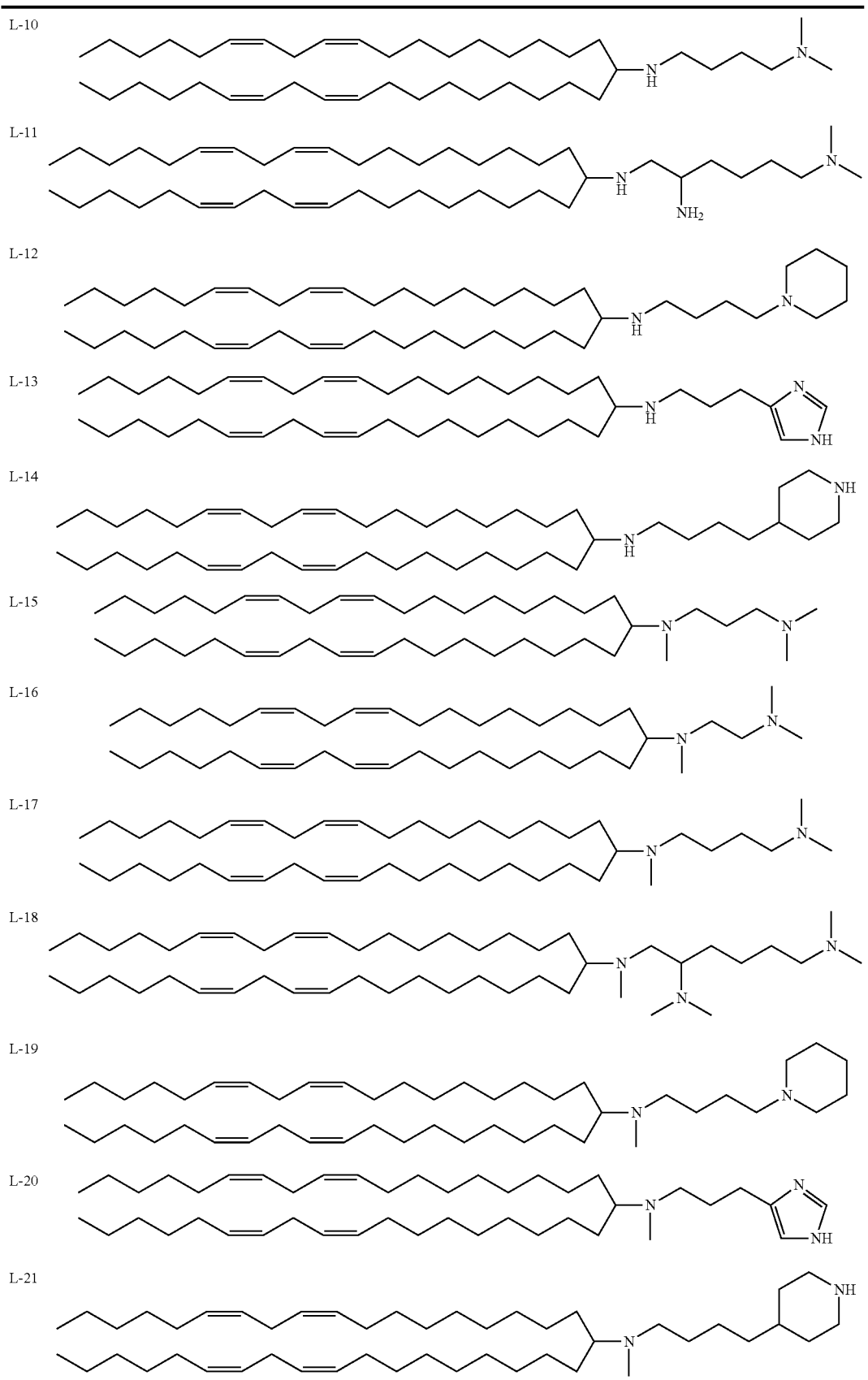

TABLE 1-continued
L-22
L-23
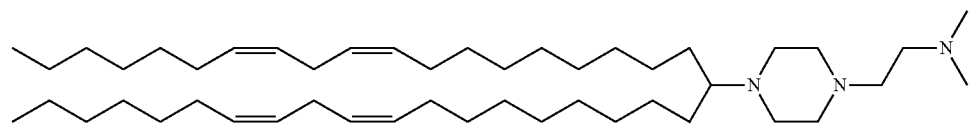 [SMILES: CCCCCC/C=C\C/C=C\CCCCCCCCC(CCCCCCCC/C=C\C/C=C\CCCCCC)N1CCN(CCN(C)C)CC1]
L-24
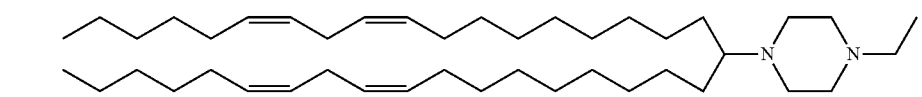
L-25
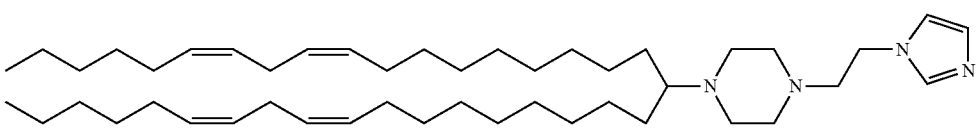 [SMILES: CCCCC/C=C\C/C=C\CCCCCCCCC(CCCCCCCC/C=C\C/C=C\CCCCC)N1CCN(CCn2ccnc2)CC1]
L-26
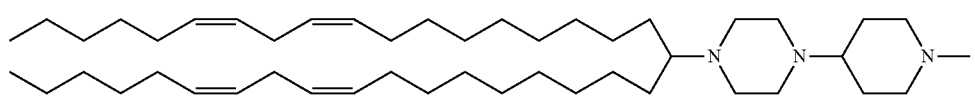 [SMILES: CCCCC/C=C\C/C=C\CCCCCCCCC(CCCCCCCC/C=C\C/C=C\CCCCC)N1CCN(C2CCN(C)CC2)CC1]
L-27
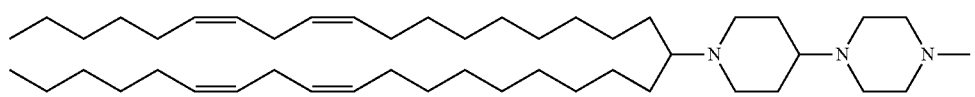 [SMILES: CCCCC/C=C\C/C=C\CCCCCCCCC(CCCCCCCC/C=C\C/C=C\CCCCC)N1CCC(N2CCN(C)CC2)CC1]
L-28
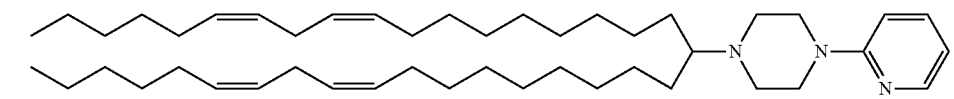 [SMILES: CCCCC/C=C\C/C=C\CCCCCCCCC(CCCCCCCC/C=C\C/C=C\CCCCC)N1CCN(c2ccccn2)CC1]
L-29
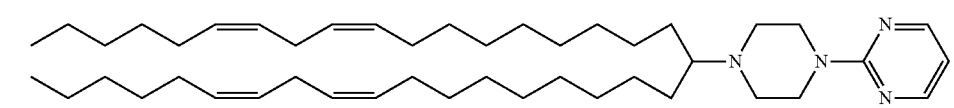 [SMILES: CCCCC/C=C\C/C=C\CCCCCCCCC(CCCCCCCC/C=C\C/C=C\CCCCC)N1CCN(c2ncccn2)CC1]
L-30
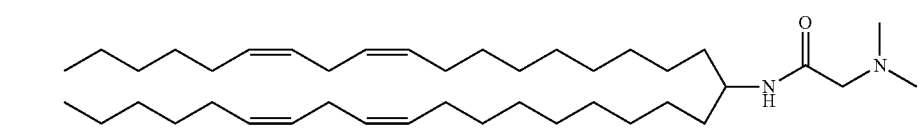 [SMILES: CCCCC/C=C\C/C=C\CCCCCCCCC(CCCCCCCC/C=C\C/C=C\CCCCC)NC(=O)CN(C)C]
L-31
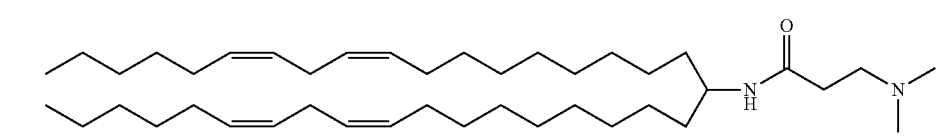 [SMILES: CCCCC/C=C\C/C=C\CCCCCCCCC(CCCCCCCC/C=C\C/C=C\CCCCC)NC(=O)CCN(C)C]
L-32
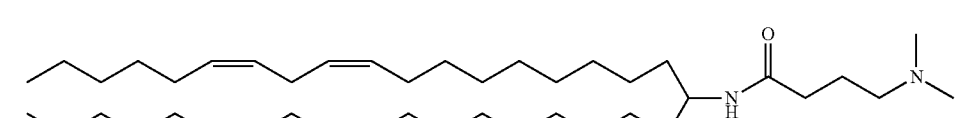
L-33
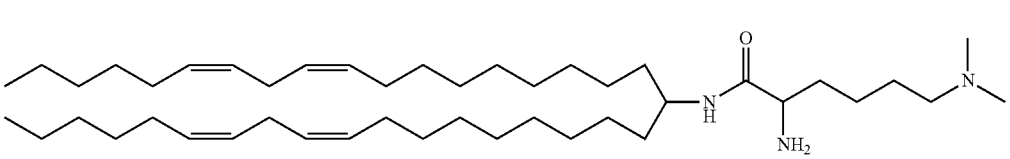

TABLE 1-continued
L-34
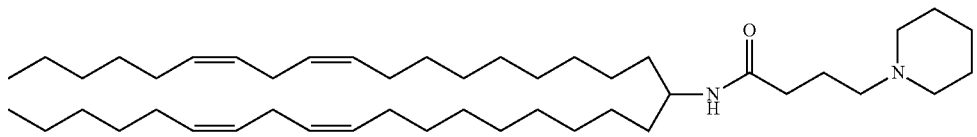 [SMILES: CCCCC/C=C\C/C=C\CCCCCCCCC(CCCCCCCC/C=C\C/C=C\CCCCC)NC(=O)CCCN1CCCCC1]
L35
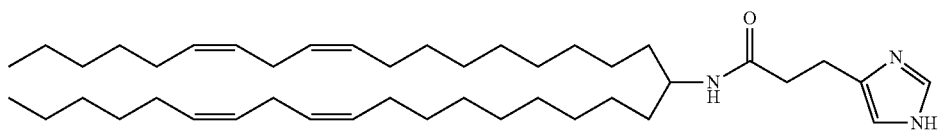 [SMILES: CCCCC/C=C\C/C=C\CCCCCCCCC(CCCCCCCC/C=C\C/C=C\CCCCC)NC(=O)CCc1c[nH]cn1]
L-36
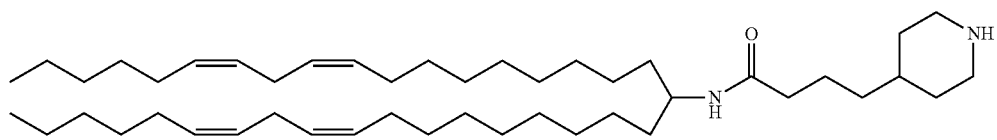 [SMILES: CCCCC/C=C\C/C=C\CCCCCCCCC(CCCCCCCC/C=C\C/C=C\CCCCC)NC(=O)CCCC1CCNCC1]
L-37
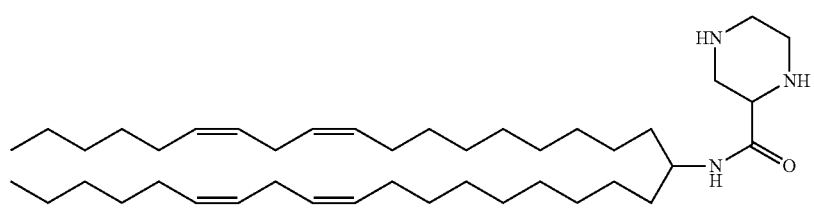 [SMILES: CCCCC/C=C\C/C=C\CCCCCCCCC(CCCCCCCC/C=C\C/C=C\CCCCC)NC(=O)C1CNCCN1]
L-38
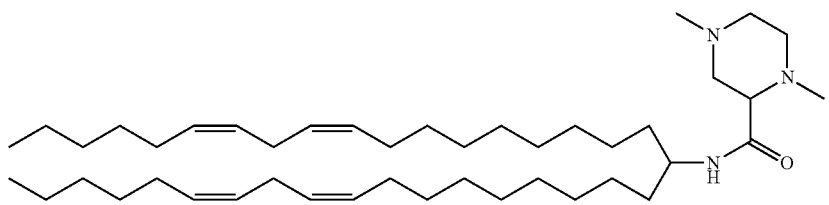 [SMILES: CCCCC/C=C\C/C=C\CCCCCCCCC(CCCCCCCC/C=C\C/C=C\CCCCC)NC(=O)C1CN(C)CCN1C]
L-39
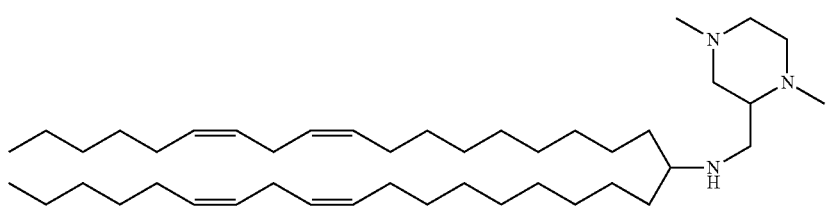 [SMILES: CCCCC/C=C\C/C=C\CCCCCCCCC(CCCCCCCC/C=C\C/C=C\CCCCC)NCC1CN(C)CCN1C]
L-40
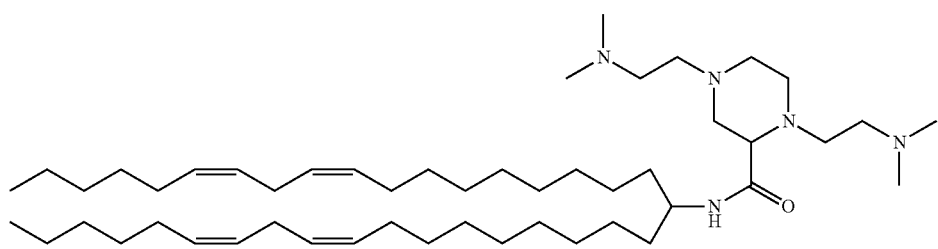 [SMILES: CCCCC/C=C\C/C=C\CCCCCCCCC(CCCCCCCC/C=C\C/C=C\CCCCC)NC(=O)C1CN(CCN(C)C)CCN1CCN(C)C]
L-41
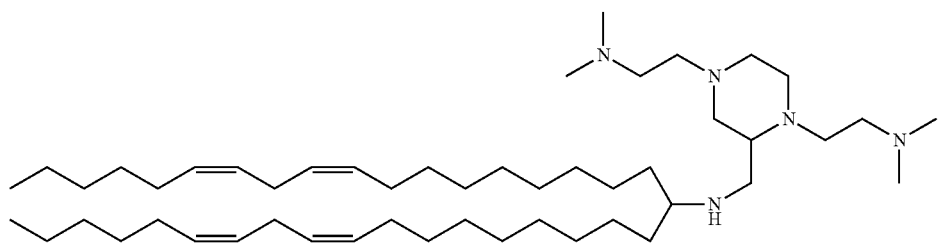 [SMILES: CCCCC/C=C\C/C=C\CCCCCCCCC(CCCCCCCC/C=C\C/C=C\CCCCC)NCC1CN(CCN(C)C)CCN1CCN(C)C]

TABLE 1-continued

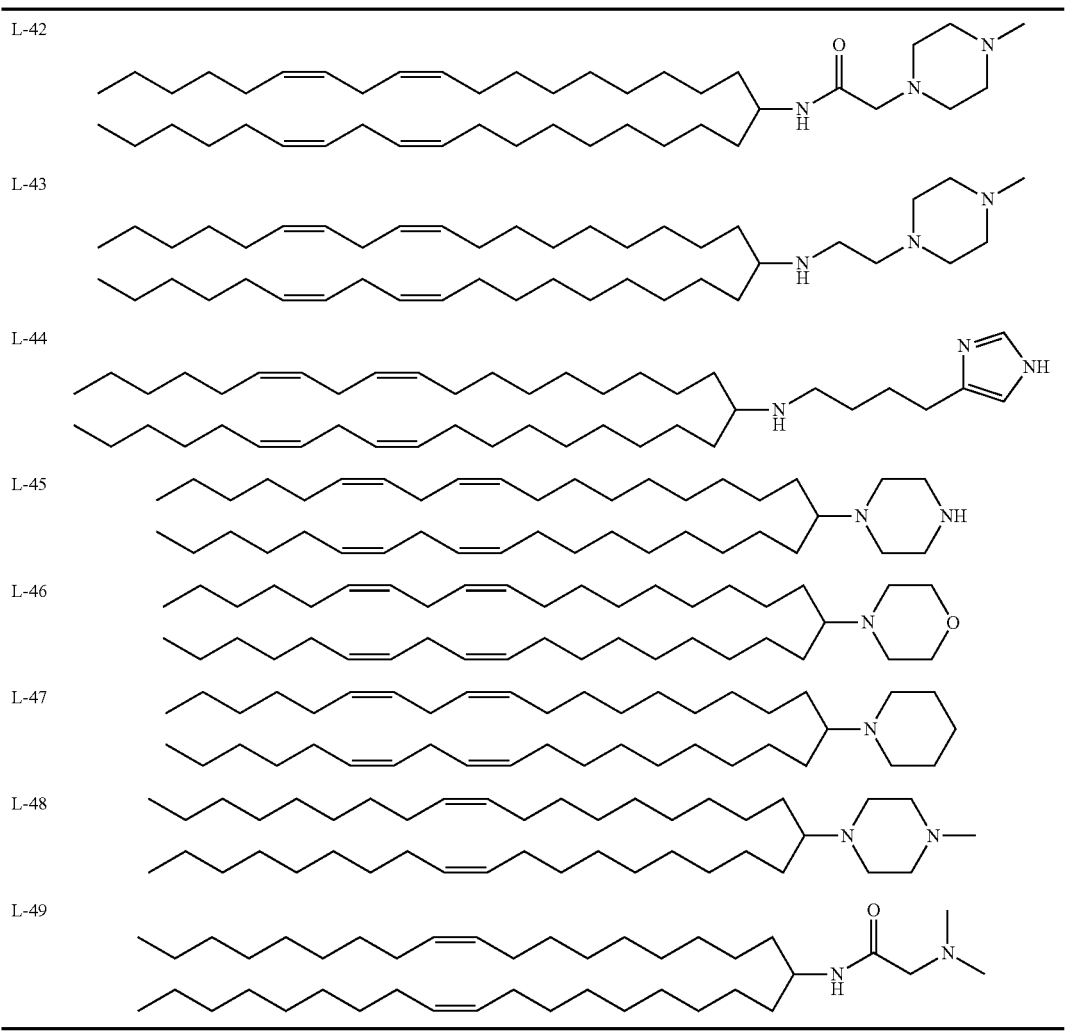

The compounds of the invention (e.g., as provided in Table 1) may be prepared by processes analogous to those established in the art, for example, by the reaction sequences shown in Schemes 1-4. Exemplary lipids produced by these reactions sequences, or modifications thereof, are provided in FIGS. 1-9 and FIG. 17.

form a corresponding amino-amide lipid having an oxo group on the carbon in $R^3$ that is adjacent to the nitrogen. In other embodiments, the amino-amine lipid of C1 is further subject to alkylation at the nitrogen or on any carbon in $R^4$. Exemplary compounds that can be produced using this scheme are provided in FIG. 1.

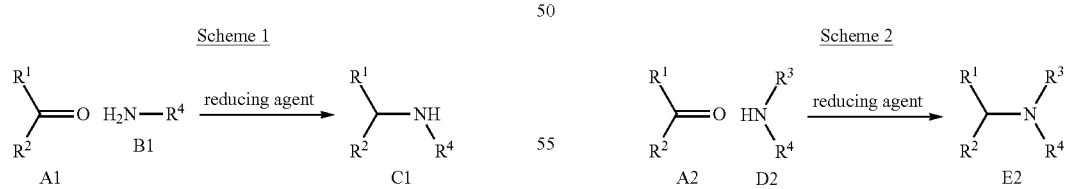

The secondary amine of formula C1 may be prepared under reductive amination conditions by treating ketone A1, where $R^1$ and $R^2$ is a lipid tail group, as described herein, with a primary amine B1, wherein $R^4$ is described herein. Conditions for reductive amination include combining ketone A1 and primary amine B1 with a reducing agent, such as sodium cyanoborohydride or sodium trioacetoxyborohydride, in an appropriate solvent. In particular embodiments, the amino-amine lipid of C1 is further oxidized to The tertiary amine of formula E2 may be prepared under reductive amination conditions by treating ketone A2, where each $R^1$ and $R^2$ is a lipid tail group, as described herein, with a secondary amine D2, where $R^3$ and $R^4$ is described herein. Conditions for reductive amination include combining ketone A2 and secondary amine D2 with a reducing agent, such as sodium cyanoborohydride or sodium trioacetoxyborohydride, in an appropriate solvent. In some embodiments of D2, $R^3$ and $R^4$ join to form a heterocyclic ring containing one or more heteroatoms, and the resultant tertiary amine E2 includes such $R^3$ and $R^4$ groups. In particular embodiments, the amino-amine lipid of E2 is further oxidized to form a corresponding amino-amide lipid having an oxo group on a carbon in $R^3$ or $R^4$ that is adjacent to the nitrogen. In other embodiments, the amino-amine lipid of E2 is further subject to alkylation on any carbon in $R^3$ and/or $R^4$.

Scheme 3

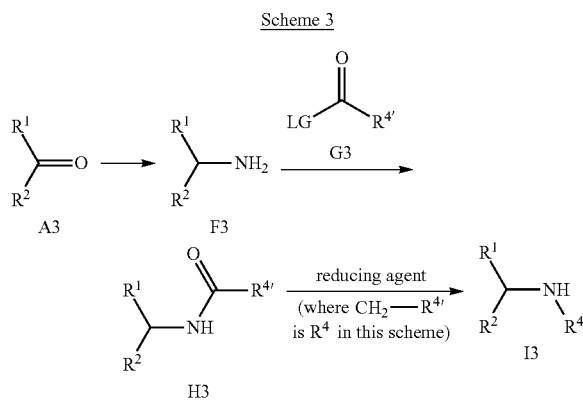

The amine of formula F3 may be prepared by combining ketone A3, ammonia, dihydrogen, and a catalyst in an appropriate solvent, optionally, under high pressure. The amino-amide lipid of formula H3 may be prepared by combining amine F3 with an activated carboxylic acid G3 in an appropriate solvent, where LG is a leaving group and $R^4$ is described herein. Exemplary LG's include halo (e.g., chloride, bromine, or iodine), tosylate, and triflate. The amino-amine lipid of I3 may be prepared by combining amide H3 with a reducing agent (e.g., lithium aluminum hydride, borane-tetrahydrofuran, or borane-dimethylsulfide). In particular embodiments, the amino-amide lipid of H3 is further subject to alkylation at the nitrogen or on any carbon in $R^{4'}$. In other embodiments, the amino-amine lipid of I3 is further subject to alkylation at the nitrogen or on any carbon in $R^4$.

Scheme 4

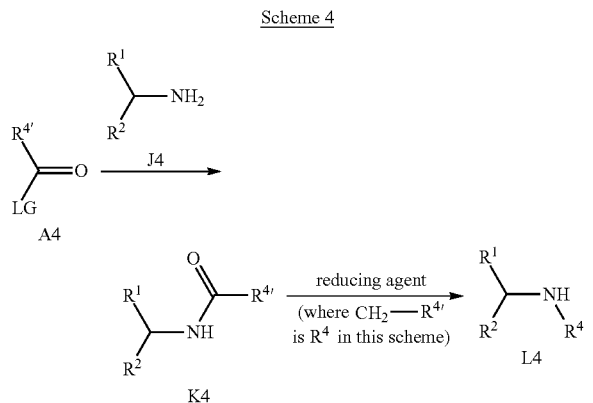

The amino-amide lipid of formula K4 may be prepared by combining ketone A4 and amine J4 in an appropriate solvent, where LG is a leaving group and $R^1$, $R^2$, and $R^4$ are described herein. Exemplary LG's include halo (e.g., chloride, bromine, or iodine), tosylate, and triflate. The amino-amine lipid of L4 may be prepared by combining amide K4 with a reducing agent (e.g., lithium aluminum hydride, borane-tetrahydrofuran, or borane-dimethylsulfide). In other embodiments, the amino-amide lipid of K4 is further subject to alkylation at the nitrogen or on any carbon in $R^{4'}$. In other embodiments, the amino-amine lipid of L4 is further subject to alkylation at the nitrogen or on any carbon in $R^4$. Exemplary compounds produced by this method are provided in FIG. 7.

In any of the above schemes, $R^4$ can be optionally substituted heterocyclyl, optionally substituted -$L^1$-$NR^5R6^5$, optionally substituted —C(O)-$L^1$-$NR^5R^6$, or optionally substituted -$L^1$-heterocyclyl, as described herein.

Figure 3:
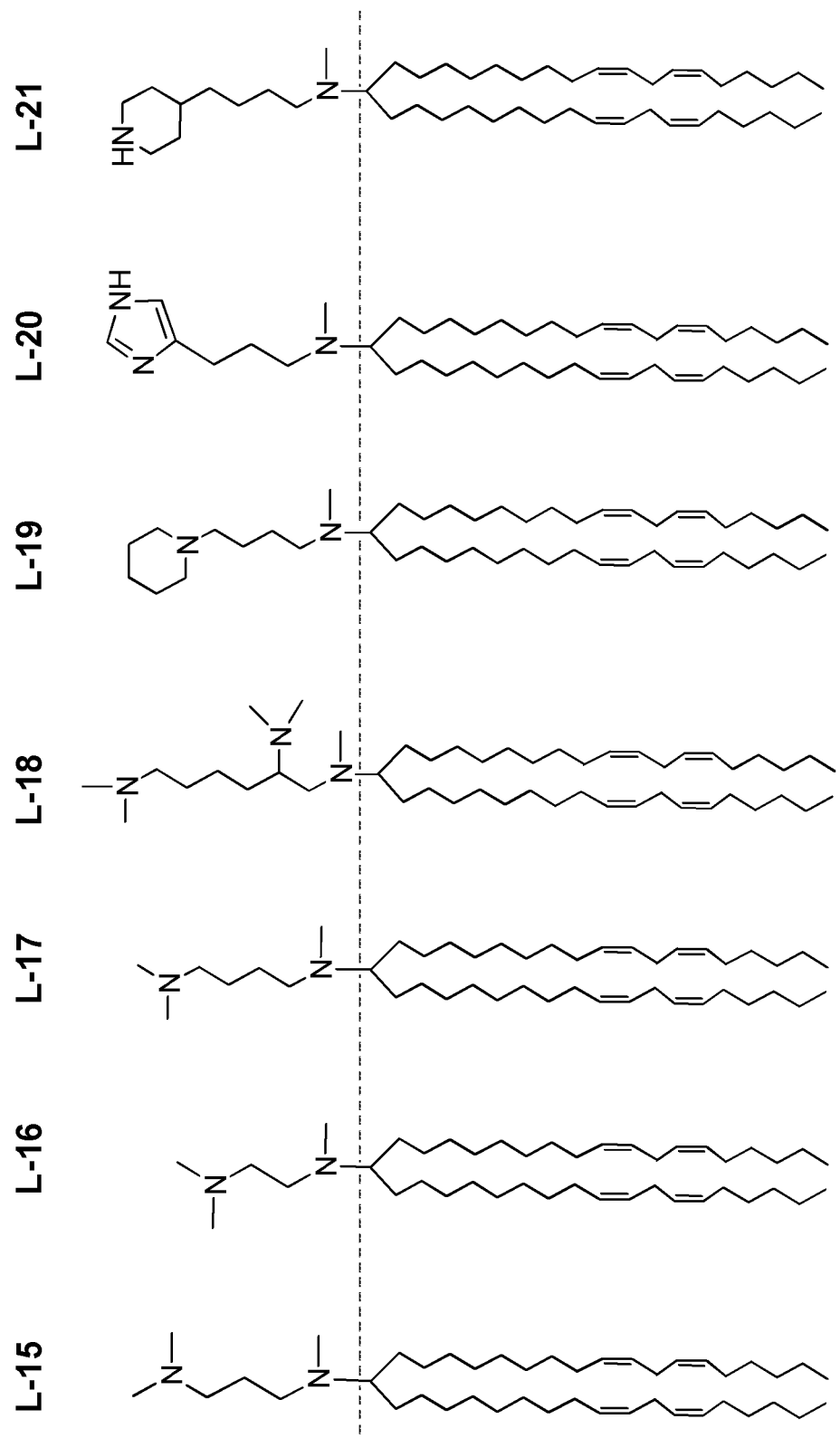
FIG. 3 shows exemplary compounds L-15 to L-21 having a tertiary amine.

In any of the above schemes, the compounds can be further alkylated to introduce an optionally substituted $C_{1-6}$ alkyl on N (i.e., $R^3$ is an optionally substituted $C_{1-6}$ alkyl) to form a tertiary amine Exemplary compounds having a tertiary amine are provided in FIG. 3.

Any of the lipids described herein, e.g., as in FIGS. 1-9 and FIG. 17, can be produced by applying the synthetic schemes provided above or in the Examples 1-5 and, if needed, by making modifications known to one skilled in the art.

Lipid Head Groups

The compounds of the invention generally include a lipid head group, a headpiece, and one or more lipid tail groups. The headpiece, e.g., >CH—, connects the head group to the tail group(s). In particular embodiments, the head group includes two or more nitrogen atoms. Any of the head groups described herein, e.g., in Tables 2 or 3, may be optionally substituted with one or more substituents (e.g., one or more substituents described herein for alkyl).

A non-limiting list of head groups having an amine group is provided in Table 2. Any of the head groups described herein, e.g., head groups H-1 to H-39 in Table 2, can be combined with any of the tail groups described herein, e.g., in Table 4, via headpiece >CH— to form a compound of the invention.

TABLE 2

Examples of lipid head groups

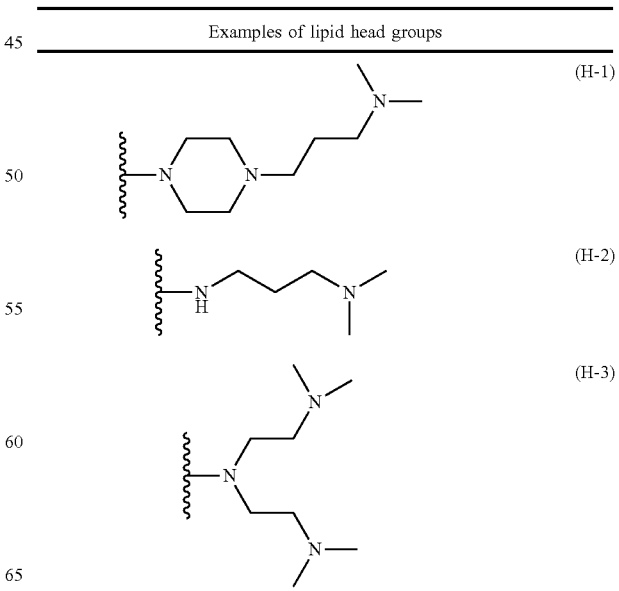

TABLE 2-continued
Examples of lipid head groups
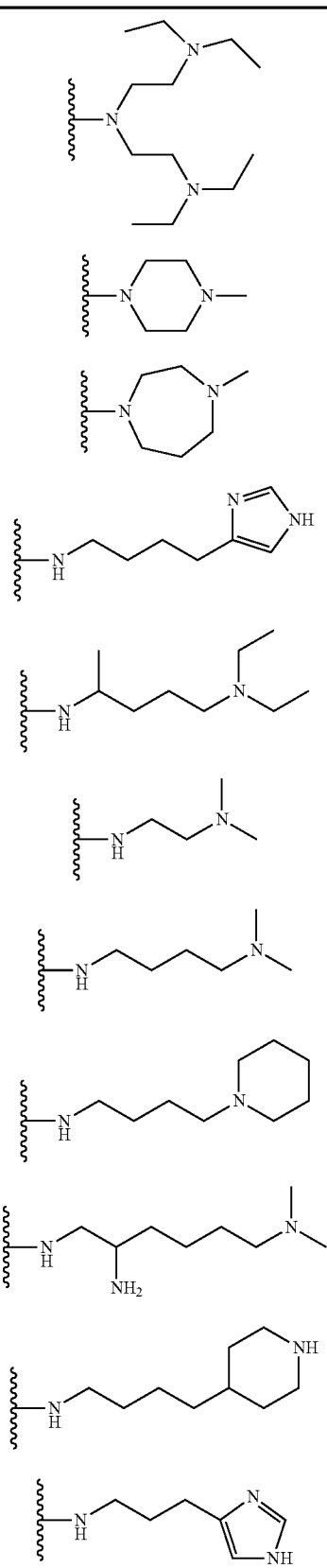
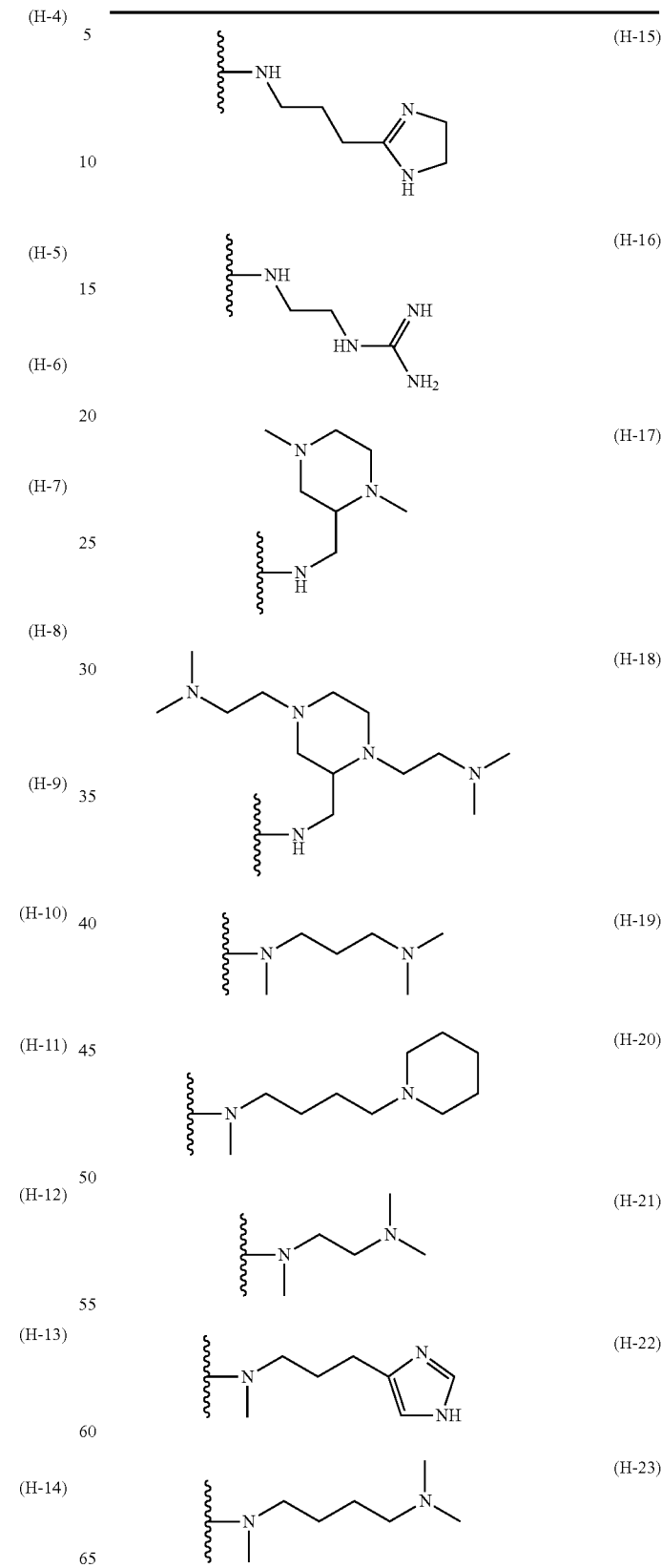

TABLE 2-continued

Examples of lipid head groups

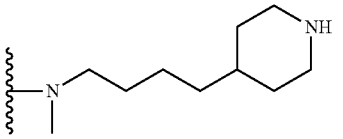 (H-24)

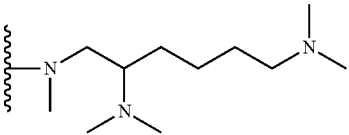 [SMILES: *N(C)CC(CCCCN(C)C)N(C)C] (H-25)

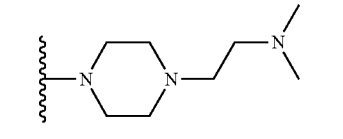 [SMILES: *N1CCN(CCN(C)C)CC1] (H-26)

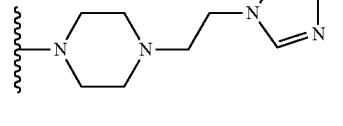 (H-27)

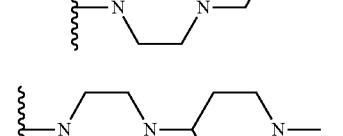 (H-28)

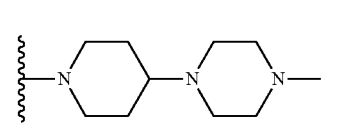 (H-29)

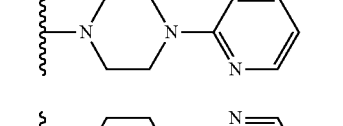 (H-30)

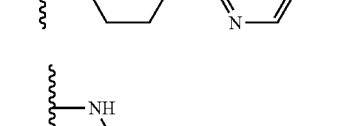 (H-31)

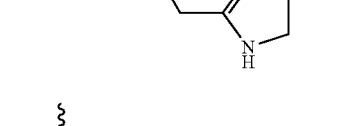 (H-32)

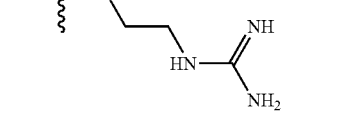 (H-33)

 (H-34)

TABLE 2-continued

Examples of lipid head groups

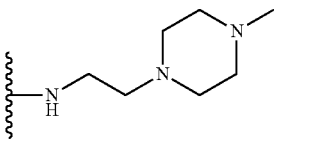 [SMILES: *NCCN1CCN(C)CC1] (H-35)

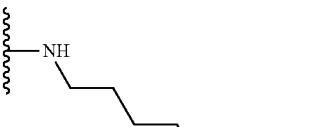 (H-36)

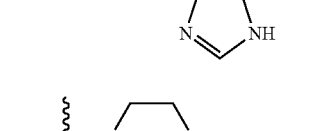 (H-37)

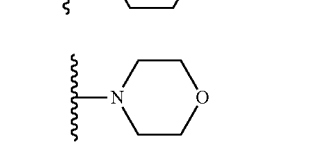 (H-38)

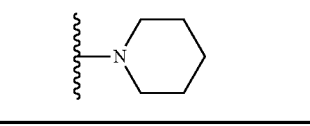 (H-39)

A non-limiting list of head groups having an amide group is provided in Table 3. Any of the head groups described herein, e.g., head groups H-40 to H-52 in Table 3, can be combined with any of the tail groups described herein, e.g., in Table 4, via headpiece >CH— to form a compound of the invention.

TABLE 3

Examples of lipid head groups containing an amide

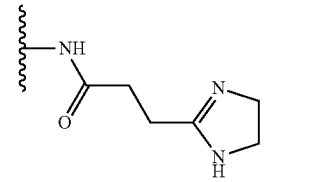 [SMILES: *NC(=O)CCC1=NCCN1] (H-40)

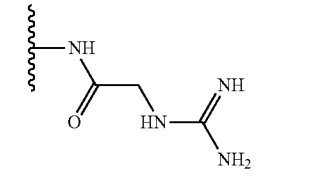 [SMILES: *NC(=O)CNC(=N)N] (H-41)

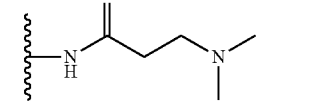 (H-42)

TABLE 3-continued

Examples of lipid head groups containing an amide

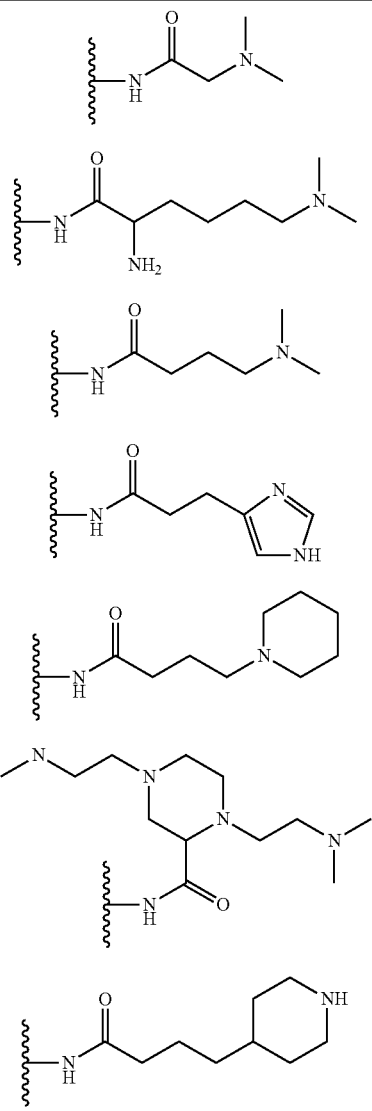

(H-43)
(H-44)
(H-45)
(H-46)
(H-47)
(H-48)
(H-49)

TABLE 3-continued

Examples of lipid head groups containing an amide (H-50)
(H-51)
(H-52)

Lipid Tail Groups

As described herein, the compounds of the invention generally include one or more tail groups that can optionally include one or more heteroatoms. For each compound, the tail groups can be the same or different. Any of the tail groups described herein, e.g., in Tables 4, may be optionally substituted with one or more substituents (e.g., one or more substituents described herein for alkyl).

Exemplary tail groups include saturated and unsaturated groups having carbon or one or more heteroatoms (e.g., O), such as linolenyl (C18:3), linolenyloxy (C18:3), linolenoyl (C18:3), linoleyl (C18:2), linoleyloxy (C18:2), and linoleoyl (C18:2); and any heteroatomic tail group described herein that is connected to the headpiece by a methylene, e.g., tail groups selected from the group of linolenyloxymethylene (C18:3), linolenoylmethylene (C18:3), and linoleyloxymethylene (C18:2), or linoleoylmethylene (C18:2). Additional non-limiting list of lipid tail groups is provided in Table 4.

TABLE 4

Examples of lipid tail groups

| | |
|---|---|
| linolenyl (C18:3) | 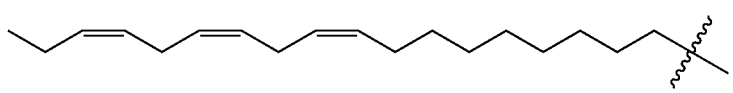 |
| linolenyloxy (C18:3) | 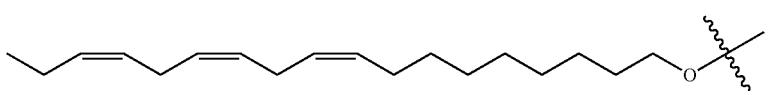 |
| linolenoyl (C18:3) | 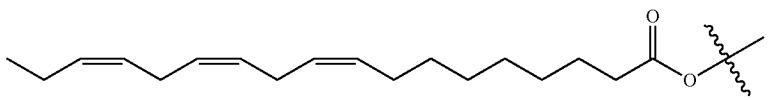 |

TABLE 4-continued

Examples of lipid tail groups

| Name | Structure |
|---|---|
| linoleyl (C18:2) | |
| linoleyloxy (C18:2) | |
| linoleoyl (C18:2) | |
| oleyl (C18:1) | |
| oleyloxy (18:1) | |
| oleyloxymethylene (18:1) | |
| oleoyl (C18:1) | |
| oleoylmethylene (C18:1) | |
| stearyl (18:0) | |
| stearyloxy (C18:0) | |
| stearoyl (C18:0) | |
| palmityl (16:0) | |
| palmityloxy (C16:0) | |
| palmitoyl (C16:0) | |

TABLE 4-continued

Examples of lipid tail groups palmitoylmethylene
(C16:0)

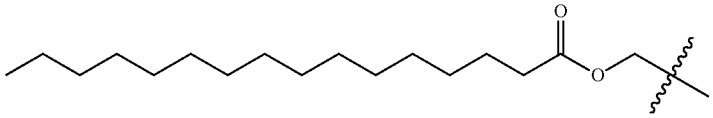 [SMILES: *COC(=O)CCCCCCCCCCCCCCC]

myristyl
(14:0)

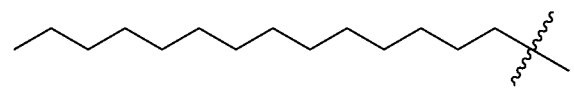 [SMILES: *CCCCCCCCCCCCCC]

myristyloxy
(C14:0)

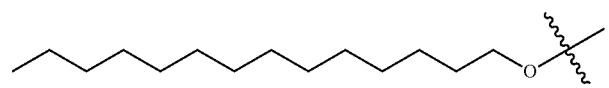 [SMILES: *OCCCCCCCCCCCCCC]

myristoyl
(C14:0)

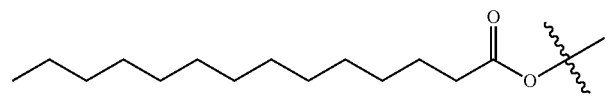 [SMILES: *OC(=O)CCCCCCCCCCCCC]

lauryl
(12:0)

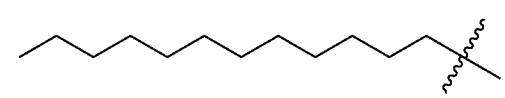 [SMILES: *CCCCCCCCCCCC]

lauryloxy
(12:0)

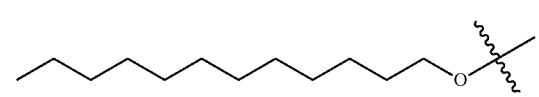 [SMILES: *OCCCCCCCCCCCC]

lauryloyl
(12:0)

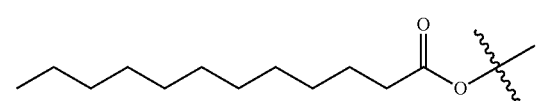 [SMILES: *OC(=O)CCCCCCCCCCC]

Formulations

The compounds of the invention may be combined with one or more lipid molecules (e.g., cationic, anionic, or neutral lipids) to produce a formulation. The formulation can also include one or more components (e.g., sterol derivatives, PEG-lipid conjugates, polyamide-lipid conjugates, gangliosides, antioxidants, surfactants, amphiphilic agents, or salts) and/or one or more polyanionic payloads (e.g., one or more nucleic acids or RNAi agents). Methods of formulating lipids to incorporate nucleic acid payloads have been described, see, for example, Judge et al., *J. Clin. Invest.* 119(3):661, 2009; Noble et al., *Cancer Chemother. Pharmacol.* 64(4):741, 2009; Abrams et al., *Mol. Ther.* 18(1):171, 2009; Yagi et al., *Cancer Res.* 69(16):6531, 2009; Ko et al., *J. Control. Release* 133(2):132, 2009; Mangala et al., *Methods Mol. Biol.* 555:29, 2009, which are hereby incorporated by reference.

Formulations with More than One Lipid Molecule

The formulations of the invention may include any useful combination of lipid molecules (e.g., a compound of the invention, a cationic lipid (optionally including one or more cationic lipids, e.g., one or more cationic lipids of the invention as described herein and/or optionally including one or more cationic lipids known in the art), a neutral lipid, an anionic lipid, and a PEG-lipid conjugate), including polypeptide-lipid conjugates and other components that aid in the formation or stability of a lipid vector, as described herein. A person of skill in that art will know how to optimize the combination that favor encapsulation of a particular agent, stability of the lipid formulation, scaled-up reaction conditions, or any other pertinent factor. The formulations of the invention may include other components that aid in formation or stability.

The percentage of each component in the formulation can be balanced to produce a lipid vector capable of encapsulating an RNAi agent and transfecting the agent into a cell. An exemplary formulation includes from about 10 mol % to about 40 mol % of one or more compounds of the invention, from about 10 mol % to about 40 mol % of one or more cationic lipids, from about 1 mol % to about 20 mol % of one or more PEG-lipid conjugates, from about 5 mol % to about 20 mol % of one or more neutral lipids, and from about 20 mol % to about 40 mol % of one or more sterol derivatives. In particular embodiments, the formulation includes from about 20 mol % to about 25 mol % (e.g., about 21.0 mol %, 21.2 mol %, 21.4 mol %, 21.6 mol %, 21.8 mol %, or 22 mol %) of one or more compounds of the invention, from about 25 mol % to about 30 mol % (e.g., about 25.1 mol %, 25.2 mol %, 25.3 mol %, 25.4 mol %, 25.5 mol %, 25.6 mol %, 25.7 mol %, 25.8 mol %, 25.9 mol %, 26.0 mol %, 26.2 mol %, 26.4 mol %, 26.6 mol %, 26.8 mol %, or 27 mol %) of one or more cationic lipids (e.g., DODMA), from about 10 mol % to about 15 mol % (e.g., about 13.0 mol %, 13.2 mol %, 13.4 mol %, 13.6 mol %, 13.8 mol %, 14 mol %, 14.1 mol %, 14.3 mol %, 14.5 mol %, 14.7 mol %, or 14.9 mol %) of one or more neutral lipids (e.g., DSPC), from about 2.5 mol % to about 10 mol % (e.g., about 2.5 mol %, 2.6 mol %, 2.7 mol %, 2.8 mol %, 2.9 mol %, 3 mol %, 3.5 mol %, 4 mol %, 4.3 mol %, 4.5 mol %, 4.7 mol %, 5 mol %, 5.3 mol %, 5.5 mol %, 5.7 mol %, 6 mol %, 6.5 mol %, 6.7 mol %, 7 mol %, 7.5 mol %, 8 mol %, 8.5 mol %, or 9 mol %) of one or more PEG-lipid conjugates (e.g., about 2.8 mol %, 2.9 mol %, 3.0 mol %, 3.5 mol %, 3.7 mol %, 3.9 mol %, 4 mol %, 4.1 mol %, 4.3 mol %, 4.5 mol %, 4.7 mol %, 4.9 mol %, 5 mol %, 5.1 mol %, 5.3 mol %, 5.5 mol %, 5.7 mol %, 5.9 mol %, 6 mol %, 6.3 mol %, 6.5 mol %, 6.7 mol %, or 7 mol % of PEG2000-DSPE and/or PEG2000-DMPE and/or 3 mol %, 3.5 mol %, 3.7 mol %, 3.9 mol %, 4 mol %, 4.1 mol %, 4.3 mol %, 4.5 mol %, 4.7 mol %, 4.9 mol %, 5 mol %, 5.1 mol %, 5.3 mol %, 5.5 mol %, 5.7 mol %, 5.9 mol %, 6 mol %, 6.3 mol %, 6.5 mol %, 6.7 mol %, or 7 mol % of PEG2000-DMG), and about 25 mol % to about 35 mol % (e.g., about 28.4 mol %, 28.6 mol %, 28.8 mol %, 29.0 mol %, 30 mol %, 31 mol %, 32 mol %, 33 mol %, 33.2 mol %, 33.4 mol %, 33.6 mol %, 33.8 mol %, 34 mol %, 34.4 mol %, 34.7 mol %, or 34.9 mol %) of a sterol derivative (e.g., cholesterol).

The formulation can include any useful amount of one or more cationic lipids. In some embodiments, the content of the cationic lipid in the formulation is from about 10 mol % to about 40 mol % (e.g., from about 10 mol % to 15 mol %, from about 15 mol % to 20 mol %, from about 20 mol % to 25 mol %, from about 25 mol % to 30 mol %, from about 30 mol % to 35 mol %, and from about 35 mol % to 40 mol %). In particular embodiments, mixed cationic lipids (e.g., 10.8 mol % of L-1 and 10.8 mol % of L-2) are used.

In some embodiments, the formulation includes lipid particles having one or more RNA-binding agents and one or more transfection lipids, where the one or more RNA-binding agents include about 10 mol % to about 40 mol % of one or more cationic lipids (e.g., DODMA) and about 0.5 mol % to about 10 mol % of one or more PEG-lipid conjugates (e.g., PEG-DSPE, such as PEG2000-DSPE, and/or PEG-DMPE, such as PEG2000-DMPE); and where the one or more transfection lipids include about 10 mol % to about 40 mol % of one or more compounds of the invention (e.g., L-6, -30, or any in Table 1), about 5 mol % to about 20 mol % of one or more neutral lipids (e.g., DSPC), about 0.5 mol % to about 10 mol % of one or more PEG-lipid conjugates (e.g., PEG-DSPE, such as PEG2000-DSPE, and/or PEG-DMPE, e.g., PEG2000-DMPE), and about 20 mol % to about 40 mol % of one or more sterol derivatives (e.g., cholesterol).

The RNA-binding agent(s) of a lipid particle can include a combination of any useful lipids and conjugates. In particular embodiments, the content of the cationic lipid (e.g., DODMA) is from about 10 mol % to about 40 mol % (e.g., from about 20 mol % to 40 mol %, 20 mol % to 35 mol %, 20 mol % to 30 mol %, 15 mol % to 40 mol %, 15 mol % to 35 mol %, 15 mol % to 25 mol %, or 15 mol % to 20 mol %). In some embodiments, the PEG-lipid conjugate (e.g., PEG-DSPE, such as PEG2000-DSPE, and/or PEG-DMPE, such as PEG2000-DMPE) is from about 0.5 mol % to about 10 mol % (e.g., from about 0.5 mol % to 1 mol %, 0.5 mol % to 5 mol %, 0.5 mol %, to 10 mol %, 1 mol % to 5 mol %, or 1 mol % to 10 mol %).

The transfection lipid(s) of a lipid particle can include a combination of any useful lipids and conjugates. In particular embodiments, the content of one or more compounds of the invention (e.g., L-6, –30, or any in Table 1) is from about 10 mol % to about 40 mol % (e.g., from about 10 mol % to 20 mol %, 10 mol % to 30 mol %, 10 mol % to 35 mol %, 15 mol % to 20 mol %, 15 mol % to 25 mol %, 15 mol % to 30 mol %, 15 mol % to 35 mol %, 15 mol % to 40 mol %, 20 mol % to 25 mol %, 20 mol % to 30 mol %, 20 mol % to 35 mol %, 20 mol % to 40 mol %, 25 mol % to 30 mol %, 25 mol % to 35 mol %, or 25 mol % to 40 mol %). In some embodiments, the content of one or more neutral lipids (e.g., DSPC) is about 5 mol % to about 20 mol % (e.g., from about 5 mol % to 10 mol %, 5 mol % to 15 mol %, 7 mol % to 10 mol %, 7 mol % to 15 mol %, 7 mol % to 20 mol %, 10 mol % to 15 mol %, or 10 mol % to 20 mol %). In some embodiments, the content of one or more PEG-lipid conjugates (e.g., PEG-DSPE, such as PEG2000-DSPE, and/or PEG-DMPE, such as PEG2000-DMPE) is about 0.5 mol % to about 10 mol % (e.g., from about 0.5 mol % to 1 mol %, 0.5 mol % to 5 mol %, 0.5 mol %, to 10 mol %, 1 mol % to 5 mol %, or 1 mol % to 10 mol %). In some embodiments, the content of one or more sterol derivatives (e.g., cholesterol) is about 20 mol % to about 40 mol % (e.g., from about 20 mol % to 25 mol %, 20 mol % to 30 mol %, 20 mol % to 35 mol %, 20 mol % to 40 mol %, 25 mol % to 30 mol %, 25 mol % to 35 mol %, or 25 mol % to 40 mol %).

In other embodiments, the compounds of the invention are used in the formulation of the RNA-binding agent(s) (e.g., about 25.9 mol % of L-6, L-30, L-48, or L-49). In particular embodiments, the compound of the invention used in the formulation of the RNA-binding agent(s) is different from the compound of the invention used in the formulation of the transfection lipid(s) (e.g., 25.9 mol % L-48 as the RNA-binding agent, and 21.6 mol % L-30 as the transfection lipid). In some embodiments of the formulation, the one or more RNA-binding agents form an internal aggregate, and the one or more transfection lipids form an external, aggregate surface. In particular embodiments, the external, aggregate surface is not a membrane, a lipid bilayer, and/or a multilamellar layer.

The formulation can also include any useful amount of one or more PEG-lipid conjugates. In some embodiments, the content of the PEG-lipid conjugate in the formulation is from about 1 mol % and about 20 mol % (e.g., from about 1 mol % to about 2 mol %, from about 2 mol % to about 4 mol %, from about 2 mol % to about 7 mol %, from about 4 mol % to about 8 mol %, from about 8 mol % to about 12 mol %, from about 12 mol % to about 16 mol %, or from about 16 mol % to about 20 mol %). In other embodiments, the content of PEG-lipid conjugate is about 7 mol %, 6 mol %, 3.0 mol %, or 2.5 mol %. Moreover, the PEG-lipid content may be varied from about 1 mol % to about 20 mol %, by appropriate adjustment of the content of either DSPC or cholesterol, or both. The PEG-lipid may be varied by using C14:0 (as in Table 4, e.g., PEG-DSPE or PEG-DMPE, etc.), C16 (PEG-DPPE, PEG-DPG, etc.), C18:0 (PEG-DSPE, PEG-DSG, etc.), or C18:1 (PEG-DOPE, PEG-DOG, etc.). Furthermore, different molecular weight PEG moieties can be used (PEG2000, PEG3400, PEG5000, etc.). In particular embodiments, mixed PEG-conjugates are used, as described herein. In particular embodiments, PEG2000-DSPE is used. In particular embodiments, PEG2000-DMPE is used.

Formulations with RNAi Agents

The formulations of the invention may be formulated with an amino-amine cationic lipid and/or an amino-amide lipid with an RNAi agent by any of the methods described herein. For example, see: Judge et al., *J. Clin. Invest.* 119(3):661, 2009; Noble et al., *Cancer Chemother. Pharmacol.* 64(4): 741, 2009; Abrams et al., *Mol. Ther.* 18(1):171, 2009; Yagi et al., *Cancer Res.* 69(16):6531, 2009; Ko et al., *J. Control. Release* 133(2):132, 2009; Mangala et al., *Methods Mol. Biol.* 555:29, 2009, which are hereby incorporated by reference.

The formulation can include an RNAi agent and a lipid molecule and/or one or more components in any useful ratio. Exemplary ratios include from a (w/w) ratio of from about 1:10 to about 1:100 (w/w) (e.g., from about 1:10 to about 1:50, e.g., about 1:20) of RNAi agent:total lipid ratio, where the total lipid ratio is the weight of the combination of one or more lipid molecules (e.g., cationic, anionic, or neutral lipids) and one or more components (e.g., sterol derivatives, PEG-lipid conjugates, polyamide-lipid conjugates, gangliosides, antioxidants, surfactants, amphiphilic agents, or salts).

The formulation can include an RNAi agent in a dose ranging from about 1 mg/kg to about 10 mg/kg of any RNAi agent described here. Exemplary doses include 1 mg/kg, 2 mg/kg, 3 mg/kg, 4 mg/kg, 5 mg/kg, 6 mg/kg, 7 mg/kg, 8 mg/kg, 9 mg/kg, and 10 mg/kg of an RNAi agent in the formulation.

Methods of Preparing Formulations

The formulations of the invention can be prepared with any useful process. In one exemplary procedure, the components of the formulation (e.g., one or more RNA-binding agents, transfection lipids, or any lipid described herein) are dissolved in a solvent (e.g., an aqueous solvent, a non-aqueous solvent, or solvent mixtures thereof). The resultant lipid suspension can be optionally filtered, mixed (e.g., batch mixed, in-line mixed, and/or vortexed), evaporated (e.g., using a nitrogen or argon stream), re-suspended (e.g., in an aqueous solvent, a non-aqueous solvent, or solvent mixtures thereof), freeze-thawed, extruded, and/or sonicated. Furthermore, the lipid suspension can be optionally processed by adding any desired components (e.g., one or more RNAi agents, RNA-binding agents, transfection lipids, and/or any lipids described herein) to produce a final suspension. The one or more desired components can be provided in the same or different solvent as the suspension. For example, the lipid suspension can be provided in a first solvent or solvent system (e.g., one or more aqueous or non-aqueous solvent(s), such as water, water-HCl, water-ethanol, buffer (e.g., phosphate buffered saline (PBS), Hank's balanced salt solution (HBSS), Dulbecco's phosphate-buffered saline (DPBS), Earle's balanced salt solution (EBSS), carbonate, lactate, ascorbate, and citrate, such as 5 mM, 10 mM, 50 mM, 75 mM, 100 mM, or 150 mM)), physiological osmolality solution (290 mOsm/kg, e.g., 0.9% saline, 5% dextrose, and 10% sucrose), saline, methanol, ethanol, n-propanol, isopropanol, n-butanol, isobutanol, tert-butanol, glycerol, ethylene glycol, propylene glycol, polyethylene glycol, chloroform, dichloromethane, hexane, cyclohexane, acetone, ether, diethyl ether, dioxan, isopropyl ether, tetrahydrofuran, or combinations thereof), and the RNAi agent can be provided in a second solvent or solvent system e.g., one or more aqueous or non-aqueous solvent(s), such as water, water-HCl, water-ethanol, buffer (e.g., phosphate buffered saline (PBS), Hank's balanced salt solution (HBSS), Dulbecco's phosphate-buffered saline (DPBS), Earle's balanced salt solution (EBSS), carbonate, lactate, ascorbate, and citrate, such as 5 mM, 10 mM, 50 mM, 75 mM, 100 mM, or 150 mM)), physiological osmolality solution (290 mOsm/kg, e.g., 0.9% saline, 5% dextrose, and 10% sucrose), saline, methanol, ethanol, n-propanol, isopropanol, n-butanol, isobutanol, tert-butanol, glycerol, ethylene glycol, propylene glycol, polyethylene glycol, chloroform, dichloromethane, hexane, cyclohexane, acetone, ether, diethyl ether, dioxan, isopropyl ether, tetrahydrofuran, or combinations thereof). Exemplary concentrations of aqueous solvents and/or buffers include from about 4% to about 8% ethanol (e.g., from about 4% to 5%, 5% to 6%, 6%, to 7%, or 7% to 8%), from about 10 mM to about 100 mM citrate (e.g., from about 10 mM to 30 mM, 30 mM to 50 mM, 50 mM to 70 mM, 70 mM to 90 mM, or 90 mM to 100 mM). Any of the solvents or solvent systems can include one or more stabilizers, such as an antioxidant, a salt (e.g., sodium chloride), citric acid, ascorbic acid, glycine, cysteine, ethylenediamine tetraacetic acid (EDTA), mannitol, lactose, trehalose, maltose, glycerol, and/or glucose. In further examples, the one or more RNA-binding agents are introduced into a lipid suspension using a first solvent or solvent system and then followed by addition of one or more transfection lipids in a second solvent or solvent system, where first and second solvents or solvent systems are the same or different (e.g., the first solvent or solvent system is any described herein; and the second solvent or solvent system is any described herein). In particular embodiments, the second solvent or solvent system include one or more aqueous or non-aqueous solvents selected from the group consisting of saline, buffer (e.g., citrate or PBS), water, and ethanol. The final suspension can be optionally separated (e.g., by ultracentrifuge), mixed (e.g., batch mixed, in-line mixed, and/or vortexed), re-suspended, adjusted (e.g., with one or more solvents or buffer systems), sonicated, freeze-thawed, extruded, and/or purified.

Cationic Lipids

One or more cationic lipids can be included in the formulation. In addition to the compounds of the invention, other cationic lipids include, but are not limited to: N,N-dioleyl-N,N-dimethylammonium chloride (DODAC), 1,2-di-O-octadecenyl-3-trimethylammonium propane (DOTMA), N,N-distearyl-N,N-dimethylammonium (DDAB), 1,2-dioleoyl-3-trimethylammonium-propane (DOTAP, including chiral forms R-DOTAP and S-DOTAP), N-(1-(2,3-dioleyloxy)propyl)-N-2-(sperminecarboxamido) ethyl)-N,N-dimethylammonium (DOSPA), dioctadecylamidoglycyl carboxyspermine (DOGS), 1,2-dioleoyl-3-dimethylammonium propane (DODAP), N,N-dimethyl-(2,3-dioleyloxy)propylamine (DODMA), N-(1,2-dimyristyloxyprop-3-yl)-N,N-dimethyl-N-hydroxyethylammonium (DMRIE), 1,2-dilinoleyloxy-3-dimethylaminopropane (DLinDMA), 1,2-dilinolenyloxy-3-dimethylaminopropane (DLenDMA), 1,2-dilinoleoyl-3-dimethylaminopropane (DLinDAP), 1-linoleoyl-2-linoleyloxy-3-dimethylaminopropane (DLin-2-DMAP), 1,2-dilinoleylcarbamoyloxy-3-dimethylaminopropane (DLin-C-DAP), 1,2-dilinoleylthio-3-dimethylaminopropane (DLin-S-DMA), 2,2-dilinoleyl-4-dimethylaminomethyl-[1,3]-dioxolane (DLin-K-DMA), 2,2-dilinoleyl-4-(2-dimethylaminoethyl)-[1,3]-dioxolane (DLin-KC$_2$-DMA), 1,2-dipalmitoyl-sn-glycero-O-ethyl-3-phosphocholine (DPePC), distearyldimethylammonium chloride (DSDMA), 1,2-dilauroyl-sn-glycero-3-ethylphosphocholine (12:0 EPC, e.g., or a chloride salt thereof), 1,2-dipalmitoyl-sn-glycero-3-ethylphosphocholine (16:0 EPC, e.g., or a chloride salt thereof), 1,2-distearoyl-sn-glycero-3-ethylphosphocholine (18:0 EPC, e.g., or a chloride salt thereof), 1,2-dioleoyl-sn-glycero-3-ethylphosphocholine (18:1 EPC, e.g., or a chloride salt thereof), dipalmitoyl phosphatidylethanolamidospermine (DPPES), dipalmitoyl phosphatidyl ethanolamido L-lysine (DPPEL), 1-[2-dioleoyloxy)ethyl]-2-oleyl-3-(2-hydroxyethyl)imidazolinium chloride (DOTIM), (1-methyl-4-(cis-9-dioleyl) methyl-pyridinium-chloride)) (SAINT), and C12-

200, as described in Love et al., *Proc Natl Acad Sci USA*, 107(5):1864-1869 (2010), which is incorporated herein by reference.

Cationic lipids include those of different chiral forms (e.g., R or S forms of any cationic lipid described herein) or any salt forms (e.g., a chloride, bromide, trifluoroacetate, or methanesulfonate salt of any cationic lipid described herein).

Additionally, a number of commercial preparations of cationic lipids may be included in the formulation. Such commercial preparations include, but are not limited to: Lipofectamine™ (a combination of DOSPA and DOPE) and Lipofectin® (a combination of DOTMA and DOPE) from Invitrogen Corp.; and Transfectam® (a composition including DOGS) and Transfase™ from Promega Corp.

Anionic Lipids

One or more anionic lipids can be included in the formulation. Such anionic lipids include, but are not limited to: phosphatidylglycerols (PGs), cardiolipins (CLs), diacylphosphatidylserines (PSs), diacylphosphatidic acids (PAs), phosphatidylinositols (PIs), N-acylphosphatidylethanolamines (NAPEs), N-succinylphosphatidylethanolamines, N-glutarylphosphatidylethanolamines, lysylphosphatidylglycerols, and palmitoyloleoylphosphatidylglycerol (POPG), as well as different chiral forms (e.g., R or S forms), salt forms (e.g., a chloride, bromide, trifluoroacetate, or methanesulfonate salts), and mixtures thereof.

Neutral Lipids

One or more neutral lipids can be included in the formulation. Such neutral lipids include, but are not limited to: ceramides, sphingomyelin (SM), diacylglycerols (DAGs), 1,2-distearoyl-sn-glycero-3-phosphocholine (DSPC, including chiral forms R-DSPC and S-DSPC), 1,2-dioleoyl-sn-glycero-3-phosphocholine (DOPC), 1,2-dipalmitoyl-sn-glycero-3-phosphocholine (DPPC), 1,2-dioleoyl-glycero-sn-3-phosphoethanolamine (DOPE), 1-palmitoyl-2-oleoyl-sn-glycero-3-phosphocholine (POPC), 1-palmitoyl-2-oleoyl-sn-glycero-3-phosphoethanolamine (POPE), 1,2-dipalmitoyl-sn-glycero-3-phosphoethanolamine (DPPE), 1,2-dimyristoyl-sn-glycero-3-phosphoethanolamine (DMPE), 1,2-distearoyl-sn-glycero-3-phosphoethanolamine (DSPE), 1,2-dielaidoyl-sn-glycero-3-phosphoethanolamine (DEPE), 1-stearoyl-2-oleoyl-sn-glycero-3-phosphoethanolamine (SOPE), 1,2-dilinoleoyl-sn-glycero-3-phosphocholine (DLPC), as well as different chiral forms (e.g., R or S forms), salt forms (e.g., a chloride, bromide, trifluoroacetate, or methanesulfonate salts), and mixtures thereof. Other diacyl-sn-glycero-3-phosphocholine and diacyl-glycero-sn-3-phosphoethanolamine lipids may also be used in the lipids particles of the invention.

In some embodiments, the neutral lipid component present in the formulation comprises one or more phospholipids. In further embodiments, the neutral lipid component comprises a mixture of one or more phospholipids and cholesterol. In some embodiments, the selection of neutral lipids for use in the formulation is guided by consideration of pharmacokinetic and/or pharmacodynamic properties, e.g., lipid particle size and stability in the bloodstream.

Sterol Derivatives

One or more sterol derivatives can be included in the formulation. Without wishing to be limited by theory, sterol derivatives can be used to stabilize the formulation and/or increase transfection. Exemplary sterol derivatives include cholesterol, derivatives of cholestanol (e.g., cholestanone, cholestenone, or coprostanol); 3β-[-(N—(N',N'-dimethylaminoethane)-carbamoyl]cholesterol (DC-cholesterol, e.g., a hydrochloride salt thereof); bis-guanidium-tren-cholesterol (BGTC); (2S,3S)-2-(((3S,10R,13R,17R)-10,13-dimethyl-17-((R)-6-methylheptan-2-yl)-2,3,4,7,8,9,10,11,12, 13,14,15,16,17-tetradecahydro-1H-cyclopenta[a]phenanthren-3-yloxy)carbonylamino)ethyl 2,3,4,4-tetrahydroxybutanoate (DPC-1); (2S,3S)-((3S,10R,13R,17R)-10,13-dimethyl-17-((R)-6-methylheptan-2-yl)-2,3,4,7,8,9,10,11,12, 13,14,15,16,17-tetradecahydro-1H-cyclopenta[a] phenanthren-3-yl) 2,3,4,4-tetrahydroxybutanoate (DPC-2); bis((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate (DPC-3); and 6-(((3S,10R,13R,17R)-10,13-dimethyl-17-((R)-6-methylheptan-2-yl)-2,3,4,7,8,9,10,11, 12,13,14,15,16,17-tetradecahydro-1H-cyclopenta[a] phenanthren-3-yloxy)oxidophosphoryloxy)-2,3,4,5-tetrahydroxyhexanoate (DPC-4).

PEG-Lipid Conjugates

One or more PEG-lipid conjugates can be included in formulation. Without wishing to be limited by theory, PEG-lipid conjugates could in reducing aggregation of lipid vectors. PEG-lipid conjugates are described in U.S. Pat. No. 5,885,613 and U.S. Patent Publication No. 2003/0077829, which are hereby incorporated by reference.

PEG-lipid conjugates that may be included in the formulation include, but are not limited to: 1,2-dimyristoyl-sn-glycero-3-phosphoethanolamine-N-(carbonyl-methoxy-polyethylene glycol) (PEG-DMPE) (e.g., 1,2-dimyristoyl-sn-glycero-3-phosphoethanolamine-N-(carbonyl-methoxy-polyethylene glycol-2000) (PEG-2000-DMPE)), 1,2-dipalmitoyl-sn-glycero-3-phosphoethanolamine-N-(carbonyl-methoxy-polyethylene glycol) (PEG-DPPE), 1,2-distearoyl-sn-glycero-3-phosphoethanolamine-N-(carbonyl-methoxy-polyethylene glycol) (PEG-DSPE), 1,2-dioleoyl-sn-glycero-3-phosphoethanolamine-N-(carbonyl-methoxy-polyethylene glycol) (PEG-DOPE), 1,2-dimyristoyl-sn-glycerol-3-(methoxy-polyethylene glycol) (PEG-DMG) (e.g., 1,2-dimyristoyl-sn-glycerol-3-(methoxy-polyethylene glycol) (PEG-2000-DMG)), 1,2-dipalmitoyl-sn-glycerol-3-(methoxy-polyethylene glycol) (PEG-DPG), 1,2-distearoyl-sn-glycerol-3-(methoxy-polyethylene glycol) (PEG-DSG), 1,2-dioleoyl-sn-glycerol-3-(methoxy-polyethylene glycol) (PEG-DOG), 3-N-[(ω-methoxypoly(ethylene glycol)2000) carbamoyl]-1,2-dimyristyloxy-propylamine (PEG-C-DMA), R-3-[(ω-methoxy poly(ethylene glycol)2000)carbamoyl)]-1,2-dimyristyloxlpropyl-3-amine (PEG-2000-C-DOMG), and PEG-ceramide conjugates (e.g., PEG-CerC$_{14}$ or PEG-CerC$_{20}$, which are described in U.S. Pat. No. 5,820,873, incorporated herein by reference). Additional PEG-lipid conjugates include PEG conjugated to any lipid described herein, such as phosphatidylethanolamine or ceramide (see, U.S. Pat. Nos. 5,820,873; 5,534,499; and 5,885, 613, which is incorporated herein by reference), and salt forms of any PEG-lipid conjugates described herein (e.g., sodium, ammonium, or trimethylammonium salts).

The PEG-lipid conjugate can include one or more various modifications, such as substitutions with any lipid molecule described herein or with PEG moieties of different molecular weights (e.g., from 300 to 5,000 daltons). Exemplary substitutions include use of one or more of C14:0 (as in Table 4), C16 (PEG-DPPE, PEG-DPG, etc.), C18:0 (PEG-DSPE, PEG-DSG, etc.), or C18:1 (PEG-DOPE, PEG-DOG, etc.) in combination with a polyethyleneglycol moiety (e.g., PEG2000, PEG3400, PEG5000, etc) to form a PEG-lipid conjugate (e.g., mPEG2000-DMG). Examples of PEG moieties with various molecular weights include PEG350, PEG550, PEG750, PEG1000, PEG2000, PEG3000, PEG3400, PEG4000, and PEG5000.

Other Components

The formulation can include any other component to aid in stabilizing the lipid vector, reducing aggregation of lipid vectors, and/or delivering a therapeutic agent (e.g., an RNAi agent). Exemplary components include polyamide-lipid conjugates (ATTA-lipids) based on ω-amino (oligoethyleneglycol) alkanoic acid monomers, such as those described in U.S. Pat. Nos. 6,320,017 and 6,586,559, which is incorporated herein by reference; gangliosides (e.g., asialoganglioside GM1 or GM2; disialoganglioside GD1a, GD1a-NAcGal, GD1-b, GD2, or GD3; globoside, monosialoganglioside GM1, GM2, or GM3, tetrasialoganglioside GQ1b, and trisialoganglioside GT1a or GT1b); antioxidants (e.g., α-tocopherol or β-hydroxytoluidine); one or more surfactants (e.g., sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cetyl ether, as well as polyoxyethylene castor oil or hydrogenated castor oil derivatives and polyglycerine fatty acid esters, such as Pluronic®, Poloxamer®, Span®, Tween®, Polysorbate®, Tyloxapol®, Emulphor®, or Cremophor® (e.g., Cremophor® EL having a major component of glycerol-polyethyleneglycol ricinoleate with fatty acid esters of polyethylene glycol); one or more amphiphilic agents (e.g., vegetable oils, such as soybean oil, safflower oil, olive oil, sesame oil, borage oil, castor oil, and cottonseed oil; mineral oils and marine oils, hydrogenated and/or fractionated triglycerides from such sources; medium chain triglycerides (MCT-oils, e.g., Miglyol®), and various synthetic or semi-synthetic mono-, di- or triglycerides, such as the defined nonpolar lipids disclosed in WO 92/05571, as well as acetylated monoglycerides, or alkyl esters of fatty acids, such isopropyl myristate, ethyl oleate (see EP 0 353 267) or fatty acid alcohols, such as oleyl alcohol, cetyl alcohol); and one or more salts, such as any salt described herein. Typically, the concentration of the lipid component selected to reduce aggregation is about 1 mol % to 15 mol %.

Lipid Vectors

The formulation of the invention can include one or more compound of the invention (e.g., a compound of Formula (I) or selected from Table 1) and any lipid-based composition capable of transporting a therapeutic agent (e.g., an RNAi agent). Exemplary lipid-based compositions include one or more lipid molecules (e.g., compounds of the invention, cationic lipids, anionic lipids, or neutral lipids) and/or one or more components (e.g., sterol derivatives and/or PEG-lipid conjugates).

Lipid vectors can be formed using any biocompatible lipid or combination of lipids capable for forming a lipid vector (e.g., liposomes, lipoplexes, and micelles). Encapsulation of a therapeutic agent into a lipid vector can protect the agent from damage or degradation or facilitate its entry into a cell. Lipid vectors, as a result of charge interactions (e.g., a cationic lipid vector and anionic cell membrane), interact and fuse with the cell membrane, thus releasing the agent into the cytoplasm. A liposome is a bilayered vesicle comprising one or more of compounds of the invention, lipid molecules, and/or components. A lipid nanoparticle is a liposome ranging in size from about 1 nm to about 1,000 nm. A lipoplex is a liposome formed with cationic lipid molecules to impart an overall positive charge to the liposome. A micelle is vesicle with a single layer of lipid molecules.

Liposomes

In certain embodiments, the lipid vector is a liposome. Typically, the lipids used are capable of forming a bilayer and are cationic. Classes of suitable lipid molecules include phospholipids (e.g., phosphotidylcholine), fatty acids, glycolipids, ceramides, glycerides, and cholesterols, or any combination thereof. Alternatively or in addition, the lipid vector can include neutral lipids (e.g., dioleoylphosphatidyl ethanolamine (DOPE)). Other lipids that can form lipid vectors are known in the art and described herein.

As used herein, a "lipid molecule" is a molecule with a hydrophobic head moiety and a hydrophilic tail moiety and may be capable of forming liposomes, including a compound of the invention or any cationic, neutral, or anionic lipid described herein. The lipid molecule can optionally be modified to include hydrophilic polymer groups. Examples of such lipid molecules include 1,2-distearoyl-sn-glycero-3-phosphoethanolamine-N-[methoxy(polyethylene glycol)-2000] (PEG2000-DSPE), e.g., an ammonium salt thereof) and 1,2-distearoyl-sn-glycero-3-phosphoethanolamine-N-[carboxy(polyethylene glycol)-2000] (PEG2000-DSPE carboxy).

Examples of lipid molecules include natural lipids, such as cardiolipin (CL), phosphatidic acid (PA), phosphatidylcholine (PC), lysophosphatidylcholine (LPC), phosphatidylethanolamine (PE), phosphatidylglycerol (PG), phosphatidylinositol (PI), and phosphatidylserine (PS); lipid mixtures, such as lechitin; sphingolipids, such as sphingosine, ceramide, sphingomyelin, cerebrosides, sulfatides, gangliosides, and phytosphingosine; cationic lipids, such as 1,2-dioleoyl-3-trimethylammonium-propane (DOTAP), 1,2-dioleoyl-3-dimethylammonium-propane (DODAP), dimethyldioctadecyl ammonium bromide (DDAB), 3-β-[N—(N',N'-dimethylaminoethane)carbamoly]cholesterol (DC-Chol), N-[1-(2,3, -ditetradecyloxy)propyl]-N,N-dimethyl-N-hydroxyethylammonium bromide (DMRIE), N-[1-(2,3, -dioleyloxy)propyl]-N,N-dimethyl-N-hydroxy ethylammonium bromide (DORIE), and 1,2-di-O-octadecenyl-3-trimethylammonium propane (DOTMA); phosphatidylcholines, such as 1,2-dilauroyl-sn-glycero-3-ethylphosphocholine, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), and 1-palmitoyl-2-oleoyl-sn-glycerol-3-phosphocholine (POPC); phosphoethanolamines, such as 1,2-dibutyryl-sn-glycero-3-phosphoethanolamine, 1,2-distearoyl-sn-glycero-3-phosphoethanolamine (DSPE), 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE), 1-palmitoyl-2-oleoyl-sn-glycero-3-phosphoethanolamine (POPE), and 1,2-dioleoyl-sn-glycero-3-phosphoethanolamine-N-(glutaryl); phosphatidic acids, such as dicetyl phosphate (DCP), 1,2-dimyristoyl-sn-glycero-3-phosphate, 1,2-dipalmitoyl-sn-glycero-3-phosphate, and 1,2-dioleoyl-sn-glycero-3-phosphate; phosphatidylglycerols, such as dipalmitoyl phosphatidylglycerol (DPPG), dioleoyl phosphatidylglycerol (DOPG), 1,2-dimyristoyl-sn-glycero-3-phospho-(1'-rac-glycerol), and 1,2-dioleoyl-sn-glycero-3-phospho-(1'-rac-glycerol); phosphatidylserines, such as 1,2-dimyristoyl-sn-glycero-3-phospho-L-serine, 1,2-dipalmitoyl-sn-glycero-3-phospho-L-serine, and 1,2-dioleoyl-sn-glycero-3-phospho-L-serine; cardiolipins, such as 1',3'-bis[1,2-dimyristoyl-sn-glycero-3-phospho]-sn-glycerol; and PEG-lipid conjugates, such as 1,2-dipalmitoyl-sn-glycero-3-phosphoethanolamine-N-[methoxy(polyethylene glycol)-750], 1,2-dipalmitoyl-sn-glycero-3-phosphoethanolamine-N-[methoxy(polyethylene glycol)-2000], 1,2-dipalmitoyl-sn-glycero-3-phosphoethanolamine-N-[methoxy (polyethylene glycol)-5000], 1,2-distearoyl-sn-glycero-3-phosphoethanolamine-N-[methoxy(polyethylene glycol)-2000], and 1,2-distearoyl-sn-glycero-3-phosphoethanolamine-N-[carboxy(polyethylene glycol)-2000].

The compounds of the invention can be combined with any useful lipid composition, including commercially available lipid compositions. Examples of such compositions include Lipofectamine™ (a combination of DOSPA and DOPE) and Lipofectin® (a combination of DOTMA and DOPE) from Invitrogen Corp.; Transfectam® (a composition including DOGS) and Transfast™ from Promega Corp.; NeuroPORTER™ and Escort™ from Sigma-Aldrich Co.; FuGENE® 6 from Roche; and LipoTAXI® from Strategene. Known lipid compositions include the Trojan Horse Liposome technology, as described in Boado, *Pharm. Res.* 24:1772-1787 (2007).

The liposomes can also include other components that aid in the formation or stability of liposomes. Examples of components include cholesterol, antioxidants (e.g., α-tocopherol or β-hydroxytoluidine), surfactants, and salts.

The liposome can be of any useful combination comprising lipid molecules, including one or more compounds of the invention and other lipid components that aid in the formation or stability of liposomes. A person of skill in that art will know how to optimize the combination that favor encapsulation of a particular agent, stability of the liposome, scaled-up reaction conditions, or any other pertinent factors. Exemplary combinations are described in Boado, *Pharm. Res.* 24:1772-1787 (2007).

Producing liposomes typically occur through a general two-step process. In the first step, the lipids and lipid components are mixed in a volatile organic solvent or mixtures of solvents to ensure a homogenous mixture of lipids. Examples of solvents include chloroform, methanol, cyclohexane, and t-butanol. The solvent is then removed to form a dry lipid mixture in a film, powder, or pellet. The solvent can also be removed by using any known analytical techniques, such as by using nitrogen, rotary evaporation, spray drying, lyophilization, and vacuum-drying.

In the second step, the dry lipid mixture is hydrated with an aqueous solution to form liposomes. The agent can be added to the aqueous solution, which results in the formation of liposomes with encapsulated agent. Alternatively, the liposomes are first formed with a first aqueous solution and then exposed to another aqueous solution containing the agent. Encapsulation of the agent can be promoted by any known technique, such as by repeat freeze-thaw cycles, sonication, or mixing. A further example of this approach is described in Boado, *Pharm. Res.* 24:1772-1787 (2007). Alternatively, the agent is coupled to a hydrophobic moiety (e.g., cholesterol) to produce a lipophilic derivative and the lipophilic derivative is used with other lipid molecules to from liposomes.

During the second step, the dry lipid mixture may or may not contain the polypeptide-lipid conjugate. The process can optionally include various additional steps, including heating the aqueous solution past the phase transition temperature of the lipid molecules before adding it to the dry lipid mixture, where particular ranges of temperatures include from about 40° C. to about 70° C.; incubating the combination of the dry lipid mixture and the aqueous solution, where particular time ranges include from about 30 minutes to about 2 hours; mixing of the dry lipid mixture and the aqueous solution during incubation, such as by vortex mixing, shaking, stirring, or agitation; addition of nonelectrolytes to the aqueous solution to ensure physiological osmolality, such as a solution of 0.9% saline, 5% dextrose, and 10% sucrose; disruption of large multilamellar vesicles, such as by extrusion or sonication; and additional incubation of the pre-formed liposomes with polypeptide-lipid conjugate, where the dry lipid mixture did not contain the lipid molecules. One of skill in the art will be able to identify the particular temperature and incubation times during this hydration step to ensure incorporation of the derivatized lipid molecule into the liposomes or to obtain stable liposomes.

The compound(s) of the invention can be added at any point in the process of forming liposomes. In one example, the compound is added to the lipids and lipid components during the formation of the dry lipid mixture. In another example, the compound is added to liposomes that are pre-formed with a dry lipid mixture containing the lipids and lipid components. In yet another example, micelles are formed with the compound, liposomes are formed with a dry lipid mixture containing lipids and lipid components, and then the micelles and liposomes are incubated together. The aqueous solution can include additional components to stabilize the agent or the liposome, such as buffers, salts, chelating agents, saline, dextrose, sucrose, etc.

In one example of this procedure, a dry film composed of the lipid mixture is hydrated with an aqueous solution containing an agent. This mixture is first heated to 50° C. for 30 minutes and then cooled to room temperature. Next, the mixture is transferred onto a dry film containing the polypeptide-lipid conjugate. The mixture is then incubated at 37° C. for two hours to incorporate the polypeptide-lipid conjugate into the liposomes containing the agent. See, e.g., Zhang et al., *J. Control. Release* 112:229-239 (2006).

Lipid Particles Having a Vesicle Structure

In certain embodiments, the lipid particle comprises a cationic lipid (e.g., DODMA, DOTMA, and/or an amino-amine lipid, amino-amide lipid, or other lipid of the invention) and an RNAi agent, as well as a neutral or zwitterionic lipid, a PEG-lipid conjugate, and, optionally, cholesterol.

Lipid Particles Having One or More RNA-Binding Agents and One or More Transfection Lipids Lipid particles also include those having one or more RNA-binding agents and one or more transfection lipids. In one embodiment, the one or more RNA-binding agents form an internal aggregate, and the one or more transfection lipids form an external, aggregate surface. In particular embodiments, the external, aggregate surface is not a membrane, a lipid bilayer, and/or a multilamellar layer. In certain embodiments, the one or more RNA-binding agents (e.g., lipids) represent about 10-90% of the total lipids. In other embodiments, the one or more RNA-binding agents (e.g., lipids) represent about 50% of the total lipid. In other embodiments, the one or more RNA-binding agents (e.g., lipids) represent about 30% of the total lipid. In certain embodiments, the complex/aggregate of a nucleic acid payload with the one or more RNA-binding agents of the lipid particle comprises a cationic lipid (e.g., DODMA, DOTMA, and/or an amino-amine lipid or amino-amide of the invention) and an RNAi agent; and the one or more transfection lipids of the lipid particle comprise a neutral or zwitterionic lipid, a PEG-lipid conjugate, and, optionally, cholesterol. In other embodiments, the one or more transfection lipids of the particle comprise a cationic lipid (e.g., DODMA, DOTMA, an amino-amine lipid, and/or an amino-amide lipid), a neutral lipid, a PEG-lipid conjugate, and, optionally, cholesterol.

RNAi Agents

RNA interference (RNAi) is a mechanism that inhibits gene expression by causing the degradation of specific RNA molecules or hindering the transcription of specific genes. In nature, RNAi targets are often RNA molecules from viruses and transposons (a form of innate immune response), although it also plays a role in regulating development and genome maintenance. Key to the mechanism of RNAi are small interfering RNA strands (siRNA), which have sufficiently complementary nucleotide sequences to a targeted messenger RNA (mRNA) molecule. The siRNA directs proteins within the RNAi pathway to the targeted mRNA and degrades them, breaking them down into smaller portions that can no longer be translated into protein.

The RNAi pathway is initiated by the enzyme Dicer, which cleaves long, double-stranded RNA (dsRNA) molecules into siRNA molecules, typically about 21 to about 23 nucleotides in length and containing about 19 base pair duplexes. One of the two strands of each fragment, known as the guide strand, is then incorporated into the RNA-induced silencing complex (RISC) and pairs with complementary sequences. RISC mediates cleavage of single-stranded RNA having sequence complementary to the antisense strand of the siRNA duplex. Cleavage of the target RNA takes place in the middle of the region complementary to the antisense strand of the siRNA duplex. The outcome of this recognition event is post-transcriptional gene silencing. This occurs when the guide strand specifically pairs with a mRNA molecule and induces the degradation by Argonaute, the catalytic component of the RISC complex.

The compounds of the invention can be used to deliver one or more RNAi agents to a cell in vitro or in vivo (e.g., in a subject). The RNAi agents can include different types of double-stranded molecules that include either RNA:RNA or RNA:DNA strands. These agents can be introduced to cells in a variety of structures, including a duplex (e.g., with or without overhangs on the 3'-terminus), a hairpin loop, or an expression vector that express one or more polynucleotides capable of forming a double-stranded polynucleotide alone or in combination with another polynucleotide. Exemplary RNAi agents include siRNA, shRNA, DsiRNA, and miRNA agents, which are described herein. Generally, these agents are about 10 to about 40 nucleotides in length, and preferred lengths are described below for particular RNAi agents.

Functional gene silencing by an RNAi agent does not necessarily include complete inhibition of the targeted gene product. In some cases, marginal decreases in gene product expression caused by an RNAi agent may translate to significant functional or phenotypic changes in the host cell, tissue, organ, or animal Therefore, gene silencing is understood to be a functional equivalent and the degree of gene product degradation to achieve silencing may differ between gene targets or host cell type.

siRNA

Small interfering RNA (siRNA) are generally double-stranded RNA molecules of 16 to 30 nucleotides in length (e.g., 18 to 25 nucleotides, e.g., 21 nucleotides) with one or two nucleotide overhangs on the 3'-terminii or without any overhangs. A skilled practitioner may vary this sequence length (e.g., to increase or decrease the overall level of gene silencing). In certain embodiments, the overhangs are UU or dTdT at the 3'-terminus. Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications, or any modifications described herein.

siRNA refers to a nucleic acid molecule capable of inhibiting or down-regulating gene expression in a sequence-specific manner; see, for example, Zamore et al., Cell 101:25 33 (2000); Bass, Nature 411:428-429 (2001); Elbashir et al., Nature 411:494-498 (2001); and PCT Publication Nos. WO 00/44895, WO 01/36646, WO 99/32619, WO 00/01846, WO 01/29058, WO 99/07409, and WO 00/44914. Methods of preparing a siRNA molecule for use in gene silencing are described in U.S. Pat. No. 7,078,196, which is hereby incorporated by reference.

shRNA

Short hairpin RNA (shRNA) are single-stranded RNA molecules in which a hairpin loop structure is present, allowing complementary nucleotides within the same strand to form intermolecular bonds. shRNA can exhibit reduced sensitivity to nuclease degradation as compared to siRNA. In certain embodiments, an shRNA have a stem length from 19 to 29 nucleotides in length (e.g., 19 to 21 nucleotides or 25 to 29 nucleotides). In some embodiments, loop size is between 4 to 23 nucleotides in length. shRNA can generally contain one or more mismatches, e.g., G-U mismatches between the two strands of the shRNA stem, without decreasing potency.

DsiRNA

Dicer-substrate RNA (DsiRNA) are double-stranded RNA agents of 25 to 35 nucleotides. Agents of such length are believed to be processed by the Dicer enzyme of the RNA interference (RNAi) pathway, whereas agents shorter than 25 nucleotides generally mimic Dicer products and escape Dicer processing. In some embodiments, DsiRNA has a single-stranded nucleotide overhang at the 3'-terminal of the antisense or sense strand of 1 to 4 nucleotides (e.g., 1 or 2 nucleotides).

Certain modified structures of DsiRNA agents were previously described, as such as in U.S. Patent Publication No. 2007/0265220, which is incorporated herein by reference. Additional DsiRNA structures and specific compositions suitable for use in the formulations of the instant invention are described in U.S. patent application Ser. No. 12/586,283; U.S. Patent Publication Nos. 2005/0244858, 2005/0277610, 2007/0265220, 2011/0021604, 2010/0173974, 2010/

0184841, 2010/0249214, 2010/0331389, 2011/0003881, 2011/0059187, 2011/0111056; and PCT Publication Nos. WO 2010/080129, WO 2010/093788, WO 2010/115202, WO 2010/115206, WO 2010/141718, WO 2010/141724, WO 2010/141933, WO 2011/072292, WO 2011/075188, which are hereby incorporated by reference. Generally, DsiRNA constructs are synthesized using solid phase oligonucleotide synthesis methods as described for 19-23 mer siRNAs (see U.S. Pat. Nos. 5,804,683; 5,831,071; 5,998,203; 6,117,657; 6,353,098; 6,362,323; 6,437,117; 6,469,158; 6,111,086; 6,008,400; and 6,111,086).

miRNA

MicroRNA (miRNA) are single-stranded RNA molecules of 17 to 25 nucleotides (e.g., 21 to 23 nucleotides) in length. A skilled practitioner may vary this sequence length to increase or decrease the overall level of gene silencing. These agents silence a target gene by binding complementary sequences on target messenger RNA. As used herein, the term "miRNA precursor" is used to encompass, without limitation, primary RNA transcripts, pri-miRNAs and pre-miRNAs. A "miRNA payload" of the invention can include pri-miRNA, pre-miRNA, and/or miRNA (or mature miRNA). In certain embodiments, an siRNA (e.g., a DsiRNA) of the invention may present a guide strand that incorporates a miRNA sequence, or is sufficiently homologous to the miRNA sequence to function as said miRNA (rendering such siRNA a "miRNA mimetic").

Antisense Compounds

Exemplary antisense compounds comprise a consecutive nucleoside length range, wherein the upper end of the range is 50 nucleosides and wherein the lower end of the range is 8 nucleosides. In certain embodiments, the upper end of the range is 35 nucleosides and the lower end of the range is 14 nucleosides. In further embodiments, the upper end of the range is 24 nucleosides and the lower end of the range is 17 nucleosides. In still further embodiments, the antisense compound is 20 consecutive nucleosides. Those skilled in the art will readily recognize that the upper end of the range, as disclosed herein comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleosides and the lower end of the range comprises 8, 9, 10, 11, 12, 13, 14, 15, 16, 17, 18, 19 or 20 consecutive nucleosides.

Exemplary antisense compounds comprise a stretch of at least 8, optionally at least 12, optionally at least 15 consecutive nucleosides that is sufficiently complementary to a target sequence to interfere with transcription, translation, promote degradation (optionally nuclease-mediated degradation) and/or otherwise disrupt the function (e.g., interfere with the function of an otherwise functional target sequence, e.g., disruption of a promoter, enhancer or other functional nucleic acid target sequence via an antisense compound-mediated mechanism) of the target sequence.

Modifications can be made to antisense compounds and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-O-(2-methoxyethyl) (2'-MOE) high affinity sugar modifications, inverted abasic caps, deoxynucleobases, and bicyclic nucleobase analogs, such as locked nucleic acids (LNA) and ethylene-bridged nucleic acids (ENA).

Method of Making RNAi Agents

RNAi agents include at least one antisense nucleotide sequence that is directed to a target nucleic acid (e.g., a target gene). Antisense nucleotides are single strands of DNA or RNA that are complementary to a chosen target sequence. In the case of antisense RNA, they prevent translation of complementary RNA strands by binding to it. Antisense DNA can be used to target a specific, complementary (coding or non-coding) RNA. In a particular embodiment, antisense nucleotides contain from about 10 to about 40 nucleotides, more preferably about 15 to about 30 nucleotides. The antisense nucleotide can have up to 80%, 85%, 90%, 95%, 99%, or even 100% complementary to the desired target gene.

Methods of producing antisense and sense nucleotides, as well as corresponding duplexes or hairpin loops, are known in the art and can be readily adapted to produce an antisense oligonucleotide that targets any target nucleic acid sequence. Antisense nucleotide sequences can be selected to optimize target specificity, such as by analyzing the target sequence and determining secondary structure, Tm, binding energy, and relative stability; and/pr to reduce the formation of secondary structures, such as dimers, hairpins, or other secondary structures that would reduce or prohibit specific binding to the target mRNA in a host cell. In some embodiments, highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.* 25(17):3389-3402, 1997). Non-limiting methods for preparing RNAi agents are described in U.S. Pat. Nos. 5,804,683; 5,831,071; 5,998,203; 6,117,657; 6,353,098; 6,362,323; 6,437,117; 6,469,158; 6,111,086; 6,008,400; and 6,111,086, which are incorporated herein by reference.

The RNAi agents can have any useful form, such as single-stranded, double-stranded, linear, circular (e.g., a plasmid), nicked circular, coiled, supercoiled, concatemerized, or charged. Additionally, nucleotides may contain 5' and 3' sense and antisense strand terminal modifications and can have blunt or overhanging terminal nucleotides (e.g., UU or TT at the 3'-terminus), or combinations thereof.

Modified nucleic acids, including modified DNA or RNA molecules, may be used in the in place of naturally occurring nucleic acids in the polynucleotides (e.g., RNAi agents) described herein. Modified nucleic acids can improve the half-life, stability, specificity, delivery, solubility, and nuclease resistance of the polynucleotides described herein. For example, siRNA agents can be partially or completed composed of nucleotide analogs that confer the beneficial qualities described above. As described in Elmén et al. (*Nucleic Acids Res.* 33:439-447 (2005)), synthetic, RNA-like nucleotide analogs (e.g., locked nucleic acids (LNA)) can be used to construct siRNA molecules that exhibit silencing activity against a target gene product.

The phosphorothioate (PS) backbone modification, where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, Eur. *J. Biochem.* 270:1628-44 (2003)). In particular embodiments, the PS modification is usually restricted to one or two bases at the 3' and 5' ends. The boranophosphate linker can be used to enhance siRNA activity while having low toxicity (Hall et al., *Nucleic Acids Res.* 32:5991-6000 (2004)). Other exemplary modifications to the oligonucleotide backbone include methylphosphonates, phosphorodithioates, phosphotriesters, aminoalkylphosphotriesters, alkyl phosphonates (e.g., 3'-alkylene phosphonate), chiral phosphonates, phosphinates, phosphoramidates (e.g., 3'-amino phosphoramidate), aminoalkylphosphoramidates, thionophosphoramidates, thionoalkylphosphonates, thionoalkylphosphotriesters, and a protein nucleotide (PNA) backbone having repeating N-(2-aminoethyl)-glycine units linked by peptide bonds, where representative PNA compounds include, but are not limited to, those disclosed in U.S. Pat. Nos. 5,539,082, 5,714,331, and 5,719,262, and Nielsen et al., *Science* 254:1497-1500 (1991).

Other modifications to the backbone include those replacing the phosphorous atom with short chain alkyl or cycloalkyl internucleoside linkages, mixed heteroatom and alkyl or cycloalkyl internucleoside linkages, or one or more short chain heteroatomic or heterocyclic internucleoside linkages (e.g., morpholino linkages; siloxane backbones; sulfide, sulfoxide and sulfone backbones; formacetyl and thioformacetyl backbones; methylene formacetyl and thioformacetyl backbones; alkene containing backbones; sulphamate backbones; methyleneimino and methylenehydrazino backbones; sulfonate and sulfonamide backbones; amide backbones; and others having mixed N, O, S and CH$_2$ component parts).

Certain modified nucleobases are particularly useful for increasing the binding affinity of the oligomeric compounds of the invention, such as 5-substituted pyrimidines, 6-azapyrimidines and N-2, N-6 and O-6 substituted purines (e.g., 2-aminopropyladenine, 5-propynyluracil, 5-propynylcytosine, and 5-methylcytosine). Exemplary modified nucleobases include 5-methylcytosine (5-me-C or m5c); 5-hydroxymethyl cytosine, xanthine, and hypoxanthine; 2-aminoadenine, 6-methyl, and other alkyl derivatives of adenine and guanine; 2-propyl and other alkyl derivatives of adenine and guanine; 2-thiouracil; 2-thiothymine; 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxy, and other 8-substituted adenines and guanines; 5-halo, particularly 5-bromo, 5-trifluoromethyl and other 5-substituted uracils and cytosines; 7-methylguanine; 7-methyladenine; 8-azaguanine; 8-azaadenine; 7-deazaguanine; 7-deazaadenine; 3-deazaguanine; and 3-deazaadenine. These modified nucleobases may be combined, in particular embodiments, with other modifications, such as any sugar modification described herein.

Modified oligonucleotides may also contain one or more substituted sugar moieties, where modifications can be made at any reactive site of the ribose ring (e.g., the 2'-OH of the ribose ring), or one or more universal bases. Exemplary modifications include 2'-halo, such as F, Br, or Cl; 2'-O-alkyl, 2'-S-alkyl, or 2'-N-alkyl, such as 2'-OMe; 2'-O-(alkyl-O)$_n$-alkyl, such as 2'-O-methoxyethyl (2'-O-MOE), 2'-O[(CH$_2$)$_n$O]$_m$CH$_3$, 2'-O(CH$_2$)$_n$OCH$_3$, 2'-O(CH$_2$)$_2$ON(CH$_3$)$_2$ O(CH$_2$)$_n$NH$_2$, O(CH$_2$)$_n$CH$_3$, 2'-O(CH$_2$)$_n$ONH$_2$, and 2'-O (CH$_2$)$_n$ON[(CH$_2$)$_n$CH$_3$)]$_2$, where n and m are from 1 to about 10; 2'-O-alkenyl, 2'-S-alkenyl, or 2'-N-alkenyl; 2'-O-alkynyl, 2'-S-alkynyl, or 2'-N-alkynyl, wherein the alkyl, alkenyl and alkynyl may be substituted or unsubstituted C$_{1-10}$ alkyl or C$_{2-10}$ alkenyl and alkynyl, as well as a bridging modification between the 2' and 4' positions of ribose to form a locked nucleic acid (LNA). Exemplary universal bases include a heterocyclic moiety located at the 1' position of a nucleotide sugar moiety in a modified nucleotide, or the equivalent position in a nucleotide sugar moiety substitution, such as 1-β-D-ribofuranosyl-5-nitroindole and 1-β-D-ribofuranosyl-3-nitropyrrole.

In certain embodiments, nucleic acids possessing described forms of modification and/or patterns of modification can be employed. Additional detail regarding exemplary modifications and modification patterns of nucleic acids can be found, e.g., in at least the following references: U.S. 2010/0240734; WO 2010/080129; WO 2010/033225; U.S. 2011/0021604; WO 2011/075188; WO2011/072292; WO 2010/141724; WO 2010/141726; WO 2010/141933; WO 2010/115202; WO 2008/136902; WO/2011/109294; WO/2011/075188; PCT/US11/42810; PCT/US11/42820; U.S. Ser. Nos. 61/435,304; 61/478,093; 61/497,387; 61/529,422; U.S. Pat. No. 7,893,245; WO 2007/051303; and U.S. 2010/0184209. Each of the preceding documents is hereby incorporated by reference in its entirety.

RNAi Gene Targets

The present invention features the silencing of a target gene in a diseased tissue or organ by treatment with a compound or formulation, in combination with an RNAi agent. The therapeutic potential of the present invention is realized when the mRNA molecules of a specific and targeted gene known or thought to be involved in the establishment or maintenance of the disease state (e.g., a cancer) are degraded by the RNAi agent.

Examples of RNAi targets for use with the present invention include developmental proteins, such as adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors; oncogene-encoded proteins (e.g., ABL1 (UniProt Entry No. P00519, NCBI Gene ID: 25), AR (UniProt Entry No. P10275, NCBI Gene ID: 3647), β-Catenin (CTNNB1, UniProt Entry No. P35222, NCBI Gene ID: 1499), BCL1 (UniProt Entry No. P24385, NCBI Gene ID: 595), BCL2 (UniProt Entry No. P10415, NCBI Gene ID: 596), BCL6 (UniProt Entry No. P41182), CBFA2 (UniProt Entry No. Q01196, NCBI Gene ID: 861), CBL (UniProt Entry No. P22681, NCBI Gene ID: 687), CSF1R (UniProt Entry No. P07333, NCBI Gene ID: 1436), ERBA1 (UniProt Entry No. P10827, NCBI Gene ID: 7067), ERBA2 (UniProt Entry No. P10828, NCBI Gene ID: 7068), ERBB (UniProt Entry No. P00533, NCBI Gene ID: 1956), ERBB2 (UniProt Entry No. P04626, NCBI Gene ID: 2064), ERBB3 (UniProt Entry No. P21860, NCBI Gene ID: 190151), ERBB4 (UniProt Entry No. Q15303, NCBI Gene ID: 600543), ETS1 (UniProt Entry No. P14921, NCBI Gene ID: 2113), ETS2 (UniProt Entry No. P15036, NCBI Gene ID: 2114), ETV6 (UniProt Entry No. 41212, NCBI Gene ID: 2120), FGR (UniProt Entry No. P09769, NCBI Gene ID: 2268), FOS (UniProt Entry No. P0110, NCBI Gene ID: 2353), FYN (UniProt Entry No. P06241, NCBI Gene ID: 2534), HCR (UniProt Entry No. Q8TD31, NCBI Gene ID: 54535), HRAS (UniProt Entry No. P01112, NCBI Gene ID: 3265), JUN (UniProt Entry No. P05412, NCBI Gene ID: 3725), KRAS (UniProt Entry No. P01116, NCBI Gene ID: 3845), LCK (UniProt Entry No. P06239 NCBI Gene ID: 3932), LYN (UniProt Entry No. P07948, NCBI Gene ID: 4067), MDM2 (UniProt Entry No. Q00987, NCBI Gene ID: 4193), MLL1 (UniProt Entry No. Q03164, NCBI Gene ID:

4297), MLL2 (UniProt Entry No. O14686, NCBI Gene ID: 8085), MLL3 (UniProt Entry No. Q8NEZ4, NCBI Gene ID: 58508), MYB (UniProt Entry No. P10242, NCBI Gene ID: 4602), MYC (UniProt Entry No. P01106, NCBI Gene ID: 4609), MYCL1 (UniProt Entry No. P12524, NCBI Gene ID: 4610), MYCN (UniProt Entry No. P04198, NCBI Gene ID: 4613), NRAS (UniProt Entry No. P01111, NCBI Gene ID: 4893), PIM1 (UniProt Entry No. P11309, NCBI Gene ID: 5292), PML (UniProt Entry No. P29890, NCBI Gene ID: 5371), RET (UniProt Entry No. P07949, NCBI Gene ID: 5979), SRC (UniProt Entry No. P12931, NCBI Gene ID: 6714), TAL1 (UniProt Entry No. P17542, NCBI Gene ID: 6886), TAL2 (UniProt Entry No. Q16559, NCBI Gene ID: 6887), TCL3 (UniProt Entry No. P31314, NCBI Gene ID: 3195), TCL5 (UniProt Entry No. P17542, NCBI Gene ID: 6886), and YES (UniProt Entry No. P07947, NCBI Gene ID: 7525)); tumor suppressor proteins (e.g., BRCA1 (UniProt Entry No. P38398, NCBI Gene ID: 672), BRCA2 (UniProt Entry No. P51587, NCBI Gene ID: 675), MADH4 (UniProt Entry No. Q13485, NCBI Gene ID: 4089), MCC (UniProt Entry No. P23508, NCBI Gene ID: 4163), NF1 (UniProt Entry No. P21359, NCBI Gene ID: 4763), NF2 (UniProt Entry No. P35240, NCBI Gene ID: 4771), RB1 (UniProt Entry No. P06400, NCBI Gene ID: 5925), TP53 (UniProt Entry No. P04637, NCBI Gene ID: 7157), PLK1 (UniProt Entry No. P53350, NCBI Gene ID: 9606), KIF1-binding protein (UniProt Entry No. Q96EK5, NCBI Gene ID: 9606), and WT1 (UniProt Entry No. P19544, NCBI Gene ID: 4790)); lipoproteins (e.g., apolipoprotein B (ApoB100, UniProt Entry No. P04114, NCBI Gene ID: 338)); enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hernicellulases, integrases, inulinases, invertases, isomerases, kinases (e.g., PLK1 (UniProt Entry No. P53350, NCBI Gene ID: 9606)), lactases, ligases (e.g., ring finger- and WD repeat-containing protein 2 (RFWD2), also known as COP1), lipases, lipoxygenases, lysozymes, nopaline synthases, octopine synthases, pectinesterases, peroxidases, phosphatases, phospholipases, phosphorylases, phytases, plant growth regulator synthases, poly galacturonases, proteinases and peptidases, pullanases, recombinases, reverse transcriptases, ribulose-1,5-bisphosphate carboxylase oxygenases (RuBisCos), topoisomerases, transferases, such as hypoxanthine guanine phosphoribosyltransferase 1 (HPRT1), and xylanases).

The liver is one of the most important target tissues for nucleic acid therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by polynucleotide-based liver therapies. A number of diseases or conditions which affect or are affected by the liver are potentially treated through knockdown (inhibition) of gene expression in the liver. Exemplary liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury. Exemplary molecular targets for liver therapeutics (e.g., including therapeutics targeted to HCC in particular)—and optionally for therapeutics addressing other targets, diseases and/or disorders, including other cancers—include CSN5 (UniProt Entry No. Q92905, NCBI Gene ID: 10987), CDK6 (UniProt Entry No. Q00534, NCBI Gene ID: 1021), ITGB1 (UniProt Entry No. P05556, NCBI Gene ID: 3688), MYC (UniProt Entry No. P01106, NCBI Gene ID: 4609), TGFβ1 (UniProt Entry No. P01137, NCBI Gene ID: 7040), Cyclin D1 (UniProt Entry No. Q9H014, NCBI Gene ID: 595), hepcidin (UniProt Entry No. P81172, NCBI Gene ID: 57817), PCSK9 (UniProt Entry No. Q8NBP7, NCBI Gene ID: 255738), and transthyretin (TTR, UniProt Entry No. P02766, NCBI Gene ID: 7276), among others.

Formulations of the invention optionally can be targeted to normal tissues (e.g., normal liver tissue), as well as to various models (e.g., orthotopic liver models, subcutaneous liver models, etc.).

One exemplary target for the formulations of the invention is Apolipoprotein B (ApoB), which is found in various classes of lipoproteins: chylomicrons, very low density lipoproteins (VLDL), intermittent density lipoproteins (IDL), and low density lipoproteins (LDL). ApoB functions as a recognition signal for the cellular binding and internalization of LDL particles by the ApoB/E receptor. An accumulation or overabundance of apolipoprotein B-containing lipoproteins can lead to lipid-related disorders such as atherosclerosis. Formulated therapies that reduce ApoB can be useful for treating lipid-related disorders. One nucleic acid based therapy, in the form of antisense therapy, has been shown to reduce ApoB levels in mouse in vivo, and treatments subsequently reduced serum cholesterol and triglyceride levels (U.S. Publication No. 2003/0215943). These results demonstrated a moderate downregulation of ApoB and its use as a target in treating lipid-related disorders.

Another exemplary target for the formulations of the invention is Protein C, which may be targeted, e.g., for the treatment of hemophilia.

Delivery of a Therapeutic Agent

The formulations of the invention may be used to deliver a therapeutic agent (e.g., polyanionic agents, nucleic acids, or RNAi agents) to cells. The agent delivered by the formulation can be used for gene-silencing (e.g., in vitro or in vivo in a subject) or to treat or prophylactically treat a disease (e.g., cancer) in a subject.

Delivery of a therapeutic agent may be assessed by using any useful method. For example, delivery with a formulation containing the compound of the invention may be assessed by 1) knockdown of a target gene or 2) toxicity or tolerability, as compared to a control at an equivalent dose. These assessments can be determined with any useful combination of lipids in the formulation, such as any cationic lipid described herein (e.g., DOTAP, DODMA, DLinDMA, and/or DLin-KC2-DMA) in combination with a compound of the invention (e.g., any compound of Formula (I) or in Table 1). In particular embodiments, an improvement of delivery of a therapeutic agent is observed when using a compound of the invention, where the improvement is more than 25% (e.g., more than a 2-fold, 5-fold, 10-fold, 100-fold, or 1000-fold improvement in delivery), as compared to a control.

Delivery of RNAi Agents

RNAi silencing can be used in a wide variety of cells, where HeLa S3, COS7, 293, NIH/3T3, A549, HT-29, CHO-KI and MCF-7 cell lines are susceptible to some level of siRNA silencing. Furthermore, suppression in mammalian cells can occur at the RNA level with specificity for the targeted genes, where a strong correlation between RNA and protein suppression has been observed. Accordingly, the compounds of the invention, and formulations thereof, may be used to deliver an RNAi agent to one or more cells (e.g., in vitro or in vivo). Exemplary RNAi agents include siRNA, shRNA, dsRNA, miRNA, and DsiRNA agents, as described herein.

In Vitro Target Knockdown

Delivery of the RNAi agent can be assessed by any useful method. For example, formulations including a therapeutic agent can be transfected in vitro in cell culture models (e.g., HeLa cells), where end point measurements include, but are not limited to, one or more of the following: (i) mRNA quantification using qPCR; (ii) protein quantification using Western blot; (iii) labeled cell internalization of the agent and/or a amino-amine or amino-amide cationic lipid of the invention. Uptake or delivery may be assessed for both the extent and duration of the above-mentioned end points. Prior to delivery, the formulation may be diluted in cell culture media at room temperature for about 30 minute, and the final concentration can be varied from 0 to 50 nM of the therapeutic agent or the amino-amine or amino-amide cationic lipid in dose-response experiments. For time-course experiments, an optimum concentration from the dose-experiment may be studied for various incubation times, e.g., 30 minutes to 7 days.

The functionality of polyanionic payload and lipid formulations may also be tested by differentially labeling the lipid compound and the therapeutic agent with fluorescent tags and performing fluorescent colocalization studies. The ability of the compounds of the invention to deliver polyanionic payloads and/or an attached fluorescent label may be assessed both by measuring the total fluorescence inside the cell and by measuring fluorescence that is not stably associated with endosomal or lysosomal compartments (to function, therapeutic agents that trigger RNAi are required not only to reach inside the cell, but also to reach the cytoplasm of the cell). Performance of fluorescence localization and cellular trafficking studies has been described in the art (Lu, et al., Mol. Pharm. 6(3):763, 2009; McNaughton et al., Proc. Natl. Acad. Sci. U.S.A. 106(15):6111, 2009).

Delivery to Particular Target Cell Types and Target Tissues

The compounds of the invention can be used to deliver therapeutic agents to various organs and tissues to treat various diseases. Exemplary targeted tissues or organs include, but are not limited to, liver, pancreas, lung, prostate, kidney, bone marrow, spleen, thymus, lymph node, brain, spinal cord, heart, skeletal muscle, skin, oral mucosa, esophagus, stomach, ileum, small intestine, colon, bladder, cervix, ovary, testis, mammary gland, adrenal gland, adipose tissue (white and/or brown), blood (e.g., hematopoietic cells, such as human hematopoietic progenitor cells, human hematopoietic stem cells, CD34+ cells, CD4+ cells), lymphocytes and other blood lineage cells.

Cancer Therapy

The compounds of the invention can be used to deliver one or more therapeutic agents (e.g., RNAi agents) to subject having cancer or at risk of developing a cancer (e.g., an increased risk of at least 10%, 20%, 30%, 40%, 50%, 60%, 70%, 80%, 90%, or 100%). Exemplary cancers include liver cancer (e.g., hepatocellular carcinoma, hepatoblastoma, cholangiocarcinoma, angiosarcoma, or hemangiosarcoma) or neuroblastoma. Exemplary neoplastic diseases and associated complications include, but are not limited to, carcinomas (e.g., lung, breast, pancreatic, colon, hepatocellular, renal, female genital tract, squamous cell, carcinoma in situ), lymphoma (e.g., histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g., small cell lung cancer, non small cell lung cancer (NSCLC)), breast, colon, bladder, prostate, gastrointestinal tract, endometrium, fallopian tube, testes and ovary, gastrointestinal stromal tumors (GISTs), prostate tumors, mast cell tumors (including canine mast cell tumors), acute myeloid myelofibrosis, leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g., sarcomas of neuroectodermal origin or leiomyosarcoma), metastasis of tumors to other tissues, and chemotherapy-induced hypoxia.

Administration and Dosage

The present invention also relates to pharmaceutical compositions that contain a compound or a therapeutically effective amount of a composition, such as a formulation including a therapeutic agent (e.g., an RNAi agent). The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer, *Science* 249:1527-1533, 1990.

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a patient with a clinically determined predisposition or increased susceptibility to development of a tumor or cancer. Compositions of the invention can be administered to the patient (e.g., a human) in an amount sufficient to delay, reduce, or preferably prevent the onset of clinical disease or tumorigenesis. In therapeutic applications, compositions are administered to a patient (e.g., a human) already suffering from a cancer in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of cancer, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the patient, but generally range from about 0.5 mg to about 3000 mg of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g., a mammal, such as a human) in an effective amount, which is an amount that produces a desirable result in a treated subject (e.g., the slowing or remission of a cancer or neurodegenerative disorder). Such therapeutically effective amounts can be determined empirically by those of skill in the art.

The patient may also receive an agent in the range of about 0.1 to 3,000 mg per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) mg dose per week. A patient may also receive an agent of the composition in the range of 0.1 to 3,000 mg per dose once every two or three weeks.

The amount (dose) of formulation and payload (e.g., DsiRNA) that is to be administered can be determined empirically. In certain embodiments, effective knockdown of gene expression is observed using 0.0001-10 mg/kg animal weight of nucleic acid payload and 0.001-200 mg/kg animal weight delivery formulation. An exemplary amount in mice is 0.1-5 mg/kg nucleic acid payload and 0.7-100 mg/kg delivery formulation. Optionally, about 1-50 mg/kg delivery formulation is administered. The amount of payload (e.g., DsiRNA) is easily increased because it is typically not toxic in larger doses.

In certain embodiments, doses can be administered daily over a period of days, weeks, or longer (e.g., between one and 28 days or more), or only once, or at other intervals, depending upon, e.g., acute versus chronic indications, etc.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds and formulations of the present invention may be used in combination with either conventional methods of treatment or therapy or may be used separately from conventional methods of treatment or therapy. When the compounds and formulations of this invention are administered in combination therapies with other agents, they may be administered sequentially or concurrently to an individual. Alternatively, pharmaceutical compositions according to the present invention include a combination of a compound or formulation of the present invention in association with a pharmaceutically acceptable excipient, as described herein, and another therapeutic or prophylactic agent known in the art.

The formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Measurement of pKa Values of Lipids in Assembled Nanoparticles

Different physiochemical properties of the lipids greatly determine the behavior of the lipids when present in different environments. One such important property is the ionization constant (Ka) of the lipid. The intrinsic pKa of the lipid may not be a correct representation of their behavior when present in an assembled nanoparticle. When present in an aqueous environment, the lipid experiences an environment with high dielectric constant, whereas in an assembled nanoparticle/vesicle, it is surrounded by lipids which provide low dielectric constant. In addition, the surrounding lipids, cholesterol, and PEGylated lipids all influence the apparent pKa of the formulation. The nature of interaction between the cationic lipids and nucleic acid being electrostatic, the apparent pKa of the formulation determines encapsulation of nucleic acid in the nanoparticle and also its subsequent intracellular release.

The TNS fluorescence method may be used to determine the apparent pKa of the lipid in the formulation. TNS (2-(p-toluidino)-6-naphthalene sulfonic acid) is a negatively charged fluorescent dye whose fluorescence is quenched in the presence of water. TNS partitions into a positively charged membrane and this results in an increase in fluorescence due to removal of water. The increase in the fluorescence can thus be used to estimate the ionization of a cationic lipid when present in different pH environment. Methods of determining pKa using TNS are known in the art, e.g., as described in the Examples.

EXAMPLES

Example 1: Synthesis of Amino-Amine Lipid L-1 from a Ketone and a Primary Amine

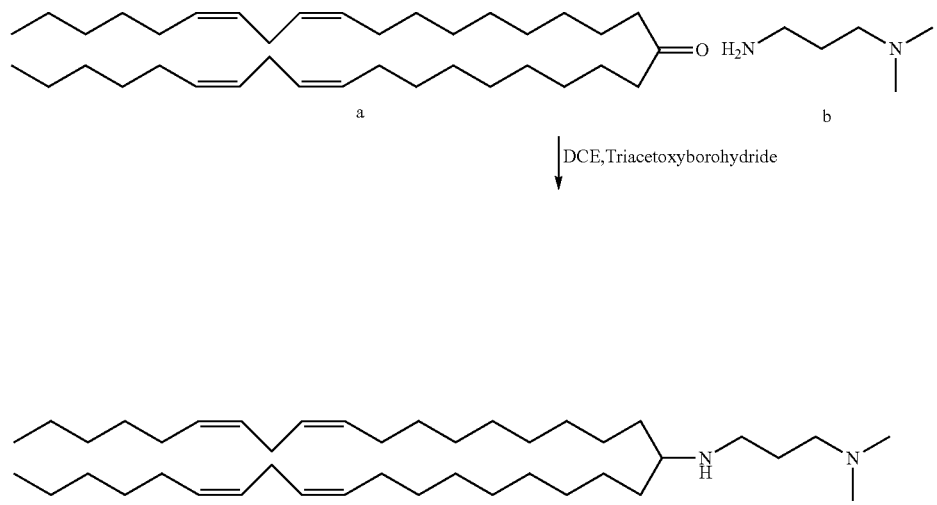

The ketone a (1 eq.) and amine b (1.1 eq.) were dissolved in dichloroethane in a dry flask all under a $N_2$ atmosphere and stirred at room temperature (RT) for 30 minutes. Triacetoxyborohydride (1.5 eq.) was added, and the mixture was stirred overnight at RT. The reaction was quenched with 1 N NaOH. The quenched reaction was diluted with DCM and extracted, once with water, once with brine, and the organic phase was dried over $Na_2SO_4$. The dried solution was filtered and concentrated on a rotoevaporator. The residue was purified by silica column (step gradient starting with 1% MeOH/DCM to 5% MeOH/DCM, yields varied from 60% to 90%) to produce compound L-1. $H^1$ NMR ($CDCl_3$): $\delta$5.41-5.30 (m, 8H), 3.12 (t, 2H), 2.91 (m, 1H), 2.77 (t, 6H), 2.48 (bs, 6H), 2.20 (m, 2H), 2.05 (q, 8H), 1.80-1.69 (m, 4H), 1.38-1.25 (m, 40H), 0.89 (t, 3H); MS: electrospray: [M+1] theory: 613, found: 613.

Figure 2A:
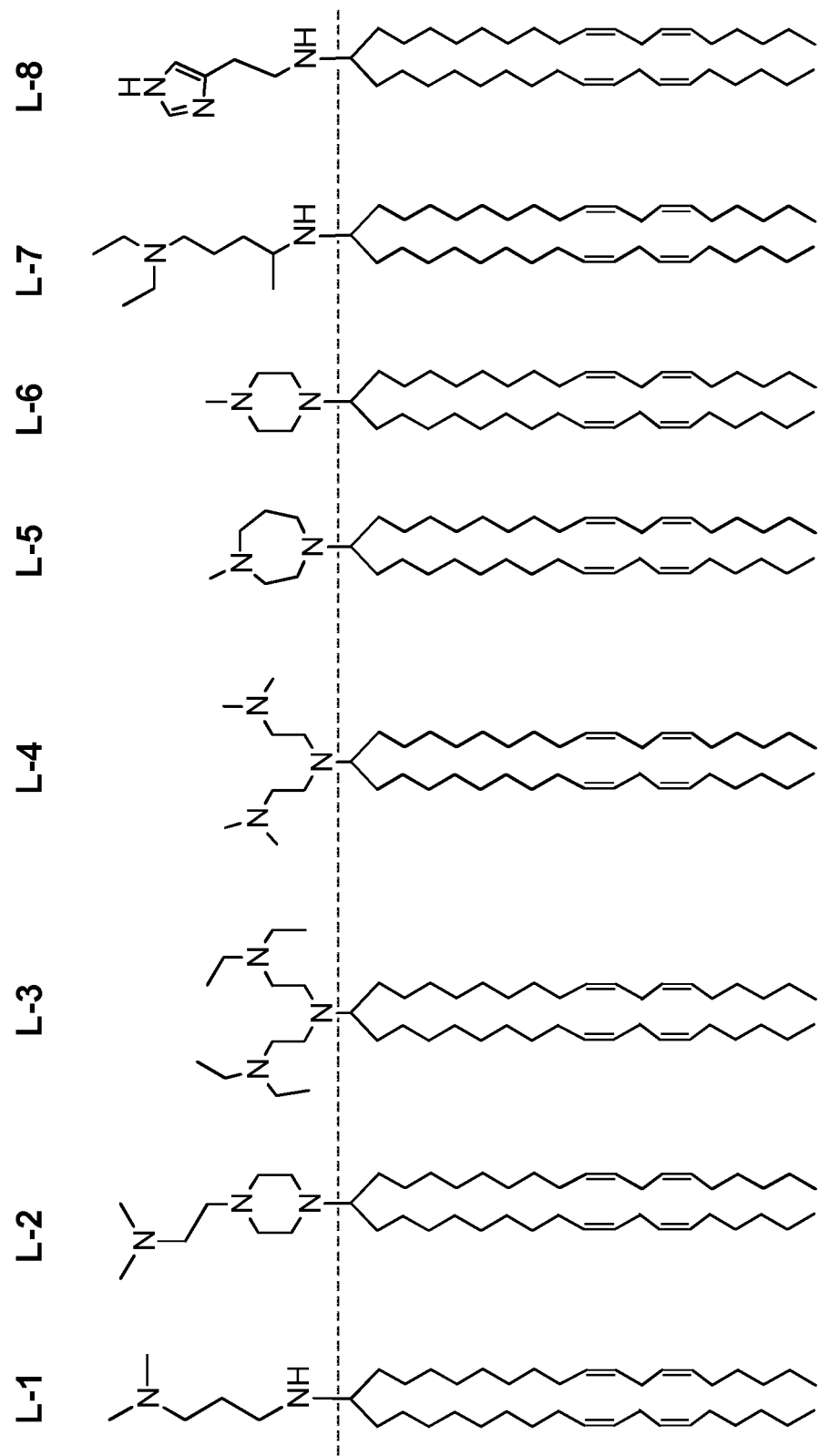
FIGS. 2A-2B show exemplary compounds L-1 to L-14.
Figure 2B:
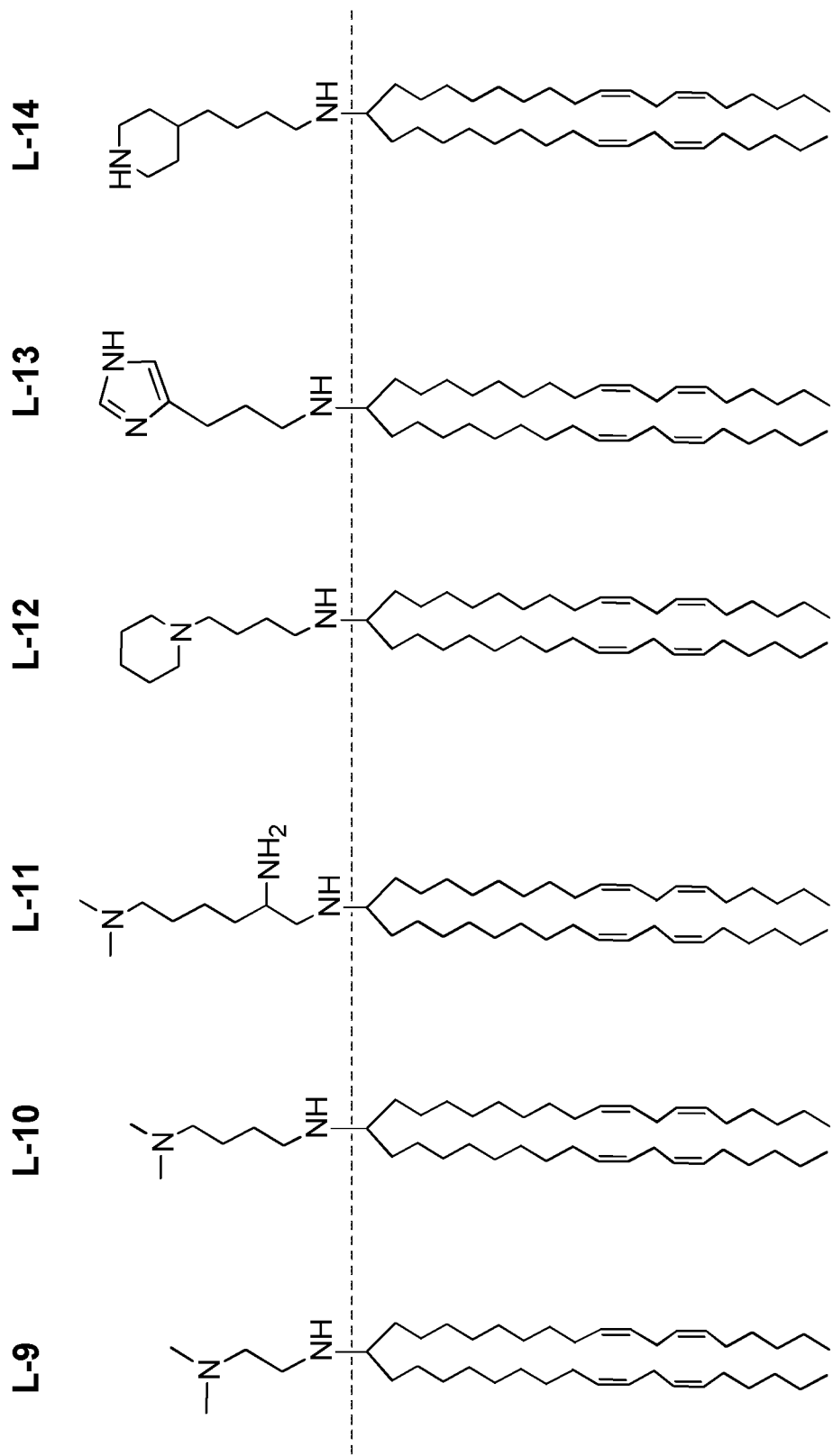

By modifying the synthetic steps of this example, additional amino-amine lipids were prepared, such as those provided in FIGS. 2A, 2B, and 3

Example 2: Synthesis of Amino-Amine Lipid L-2 from a Ketone and a Secondary Amine

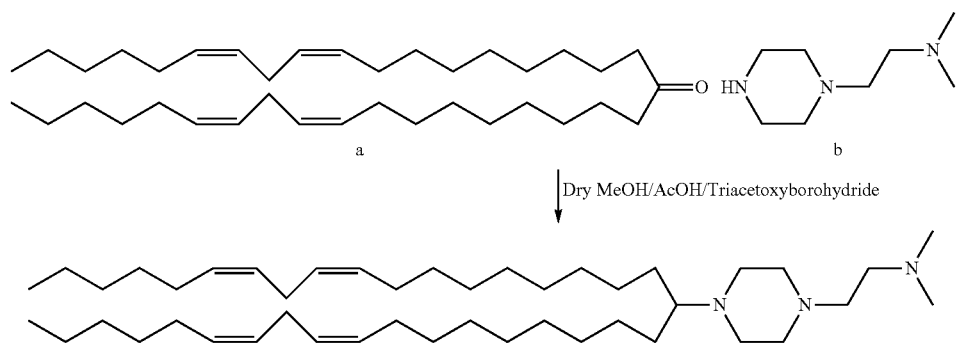

The ketone a (1 eq.) was dissolved in dry MeOH in a dry flask all under an $N_2$ atmosphere. The amine b (1.1 eq.) was added, followed by triacetoxyborohydride (1.5 eq.) and AcOH (1 eq.), and the reaction was stirred overnight at RT. The reaction was diluted with DCM and extracted, once with water, once with brine, and the organic phase was dried over $Na_2SO_4$. The dried solution was filtered and concentrated on a rotoevaporator. The residue was purified by silica column (step gradient starting with 1% MeOH/DCM to 5% MeOH/DCM, yields vary from 60% to 90%) to produce compound L-2. $H^1$ NMR: ($CD_3OD$) δ5.39-5.30 (m, 8H), 2.78 (t, 4H), 2.59-2.52 (m, 10H), 2.33 (bs, 8H), 2.07 (q, 8H), 1.25 (m, 2H), 1.40-1.26 (m, 40H), 0.914 (t, 6H); MS: electrospray pos. [M+1] theory 668, found 668.

Figure 4:
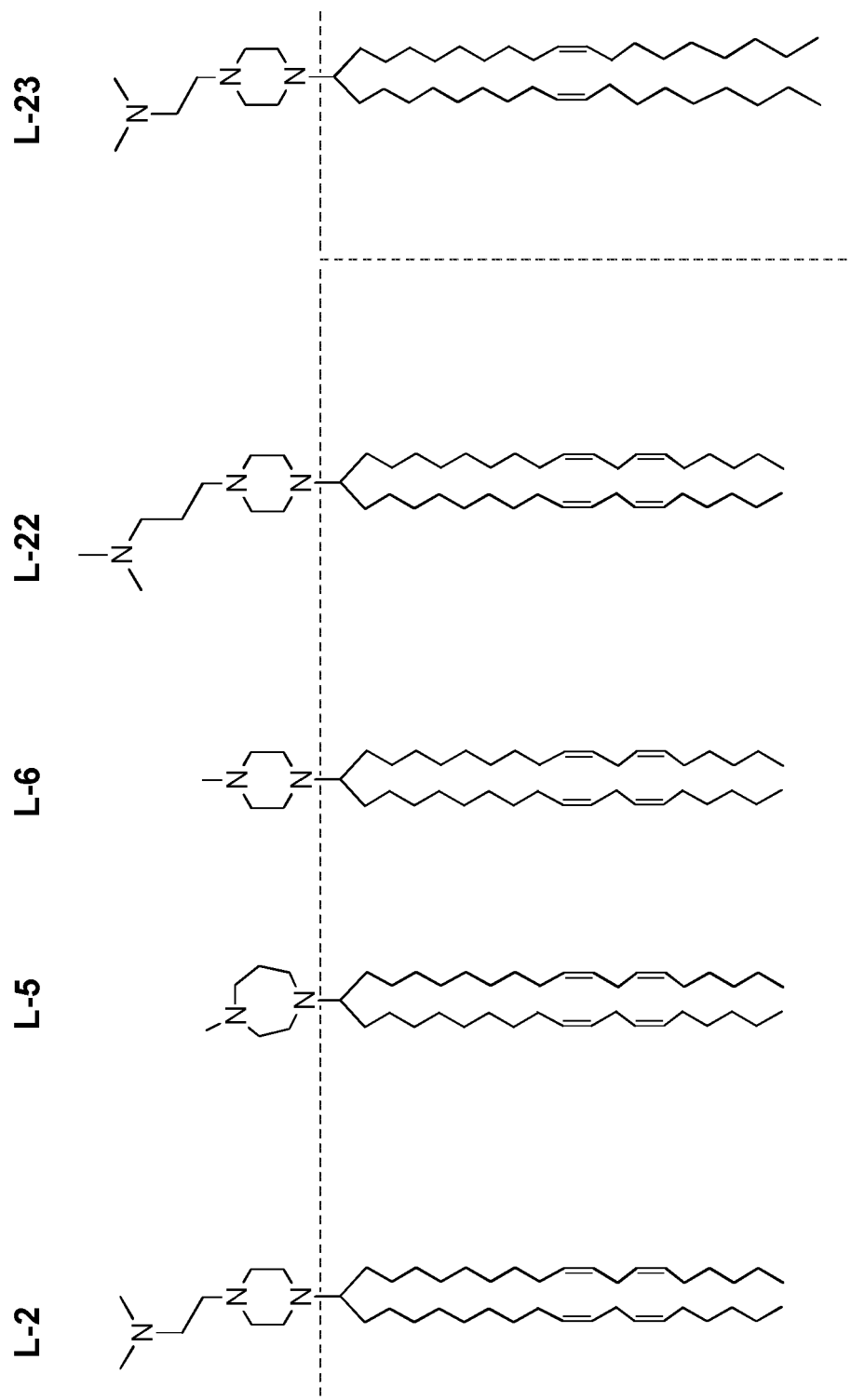
FIG. 4 shows exemplary analogs of L-2, including compounds L-5, L-6, L-22, and L-23.
Figure 5:
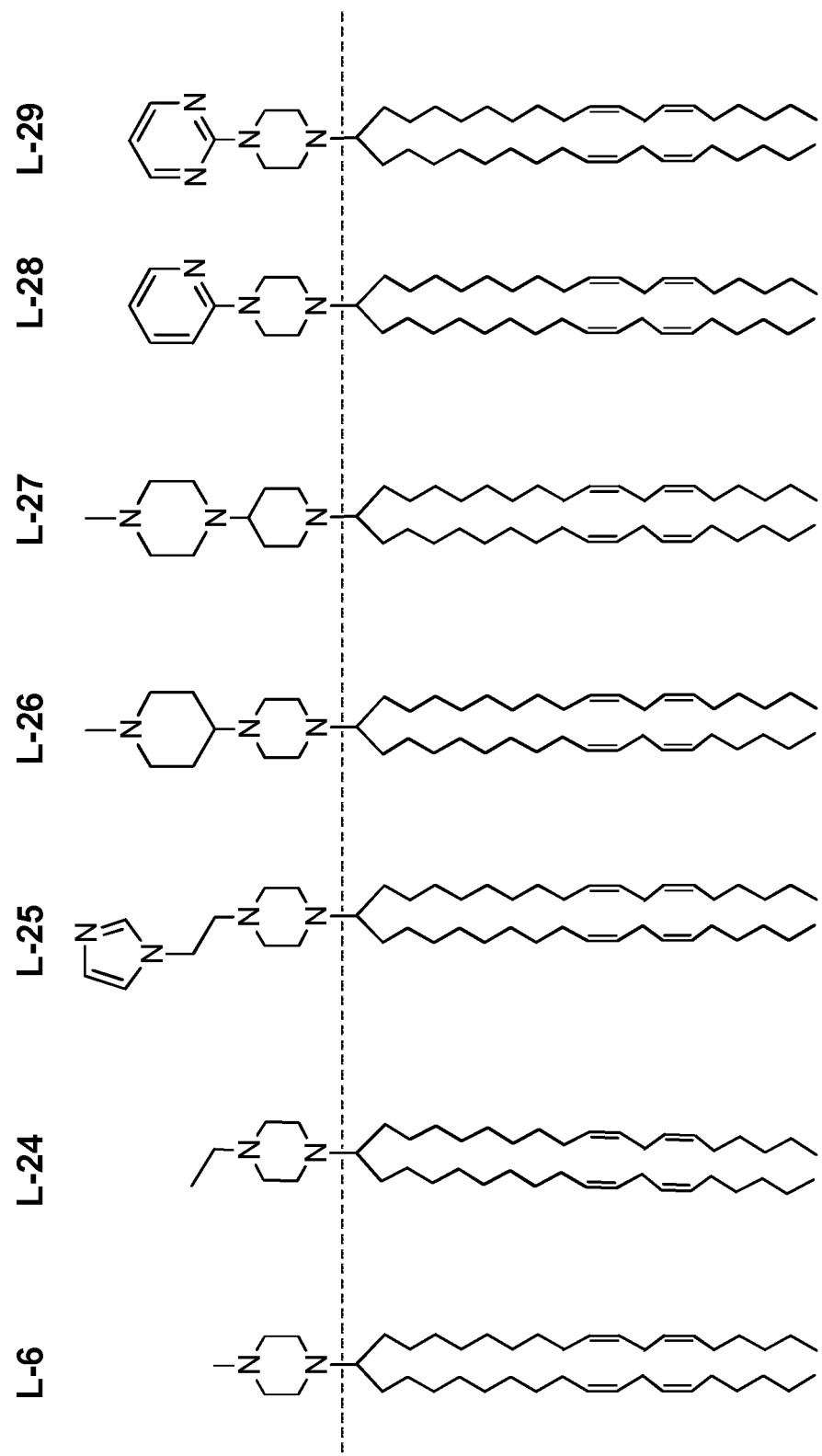
FIG. 5 shows exemplary analogs of L-6, including compounds L-24 to L-29.

By modifying the synthetic steps of this example, additional amino-amine lipids were prepared, such as the L-2 and L-6 analogs provided in FIGS. 4 and 5.

Example 3: Synthesis of the Lipid L-46 from a Ketone and Morpholine

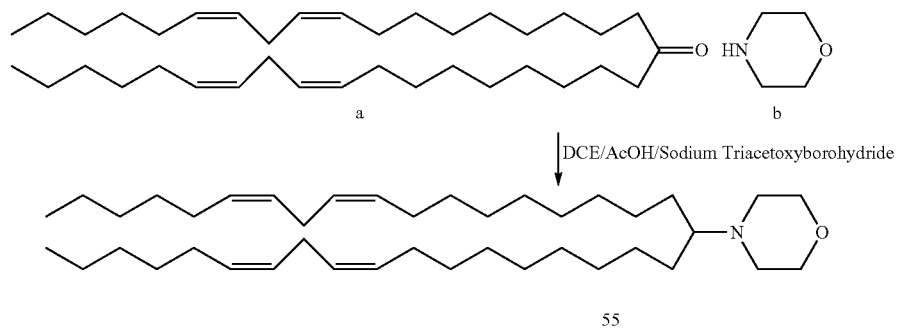

To a mixture of ketone a (2.66 g; 5.05 mmol), morpholine b (1.34 ml; 15 mmol) and AcOH (1.77 ml; 30 mmol) in DCE (12 ml) was added $NaBH(AcO)_3$ (1.6 g; 7.5 mmol). The reaction mixture was stirred at RT for 72 h. TLC test (silica gel; elution with hexane:EtAc-$Et_3N$ 95:5) indicated approximately 45% conversion. The reaction mixture was diluted with 5% aqueous $K_2CO_3$ and extracted with DCM. The solvent was dried over $K_2CO_3$ and evaporated on a rotoevaporator. The residue was separated by LC on silica gel (elution with hexane:EtAc 90:10). The desired product L-46 was obtained in 39% yield (1.18 g) and was pure by NMR.

Example 4: Synthesis of the Lipid L-47 from a Ketone and Piperidine

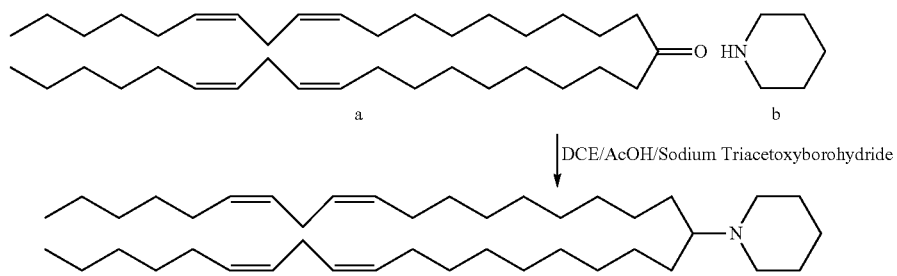

To a mixture of dilinoleyl ketone a (3.99 g; 7.58 mmol), piperidine b (2.25 ml; 22 mmol) and AcOH (1.33 ml; 23 mmol) in DCE (24 ml) was added NaBH(AcO)$_3$ (2.4 g; 11.3 mmol). The reaction mixture was stirred at RT for 96 h. TLC test (silica gel; elution with hexane:EtAc-Et$_3$N 95:5) indicated around 35% conversion. The reaction mixture was diluted with 5% aqueous K$_2$CO$_3$ and extracted with DCM. The solvent was dried over K$_2$CO$_3$ and evaporated on a rotoevaporator. The residue was separated by LC on silica gel (elution was with hexane:EtAc 90:10. The desired product L-47 was obtained in 29% yield (1.30 g) and was pure by NMR.

Figure 9:
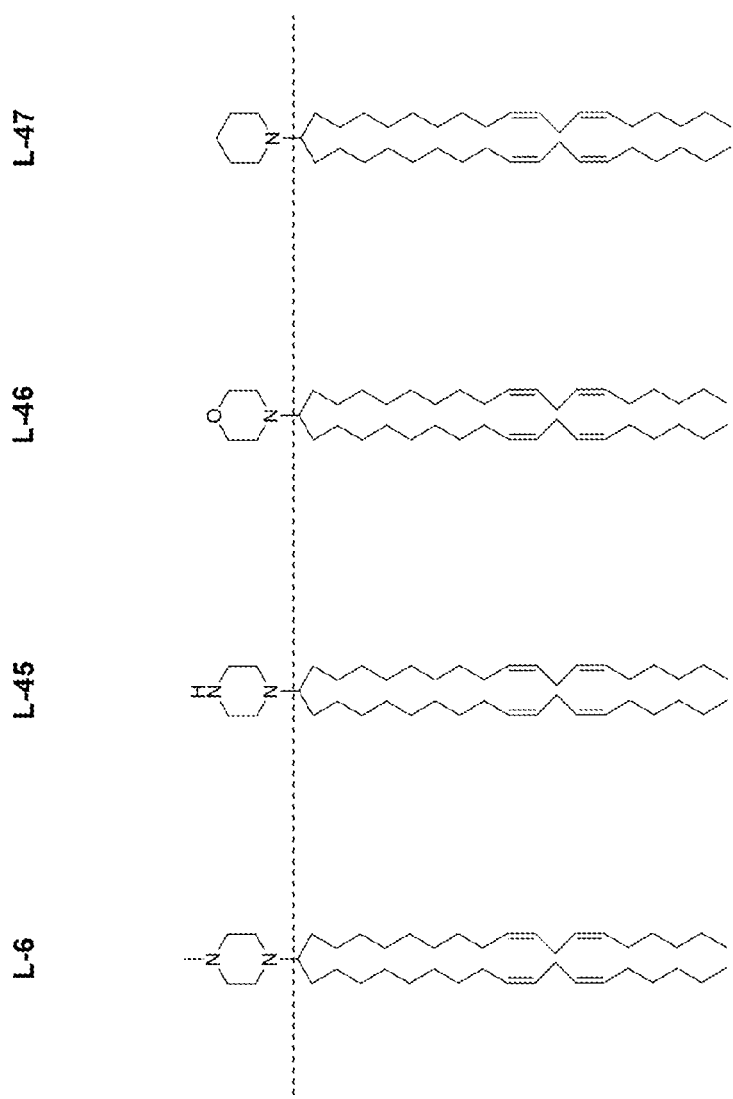
FIG. 9 shows further exemplary cationic lipid structures of the invention L-6, L-45, L-46, and L-47.

By using the methods provided in this Example, as well as Example 3, cationic lipids having various head groups, such as those provided in FIG. 9, can be prepared.

Example 5: Synthesis of Amide Cationic Lipids from a Primary Amine and a Carboxylic Acid The following dilinoleyl amide derivatives were prepared using the following general procedure. To a solution of dilinoleyl amine (338 mg; 0.64 mmol), HOBt (65 mg; 0.5 mmol), aminoacid (1 mmol), and DIPEA (1 eq.) in DCM (15 g/mL) were combined followed by the addition of EDC (1.2 mmol). The reaction mixture was stirred at room temperature overnight. TLC indicated that the reaction was complete. The reaction mixture was diluted with 0.5% K$_2$CO$_3$ in water and extracted with DCM. Following concentration on a rotoevaporator, the crude product was purified by silica gel chromatography (gradient from hexane:Et$_3$N 95:5 to hexane:CHCl$_3$:Et$_3$N 46:44:5). Obtained yields were between 80-85%.

Dioleyl derivatives were also prepared based on the schemes provided below:

Synthesis of Lipid L-30 from a Primary Amine and a Carboxylic Acid

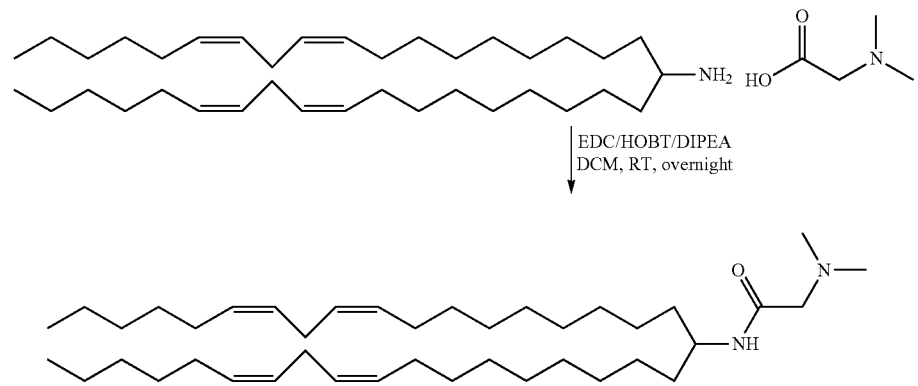

Synthesis of Lipid L-31 from a Primary Amine and a Carboxylic Acid

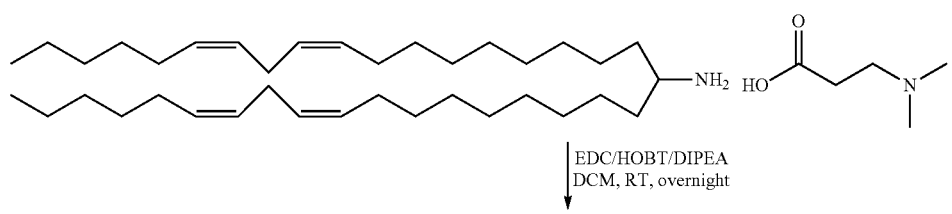

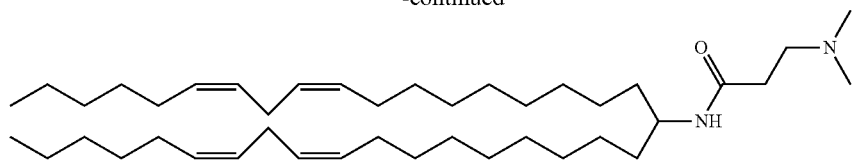

Synthesis of Lipid L-32 from a Primary Amine and a Carboxylic Acid

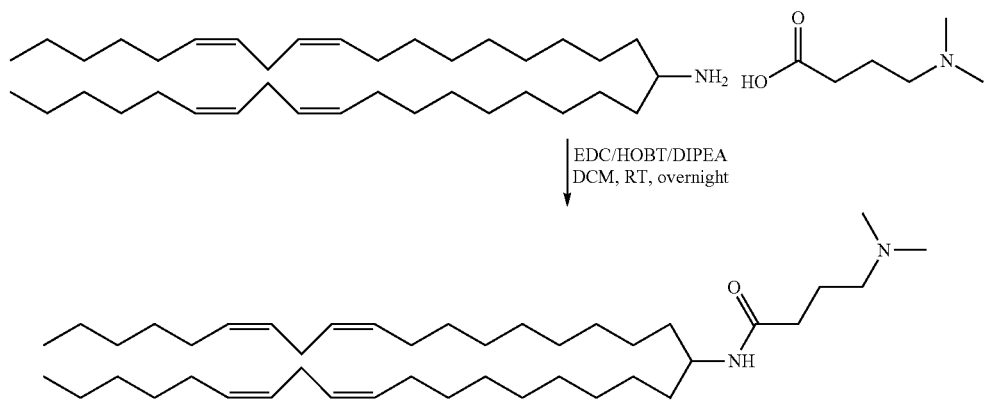

Synthesis of Lipid L-42 from a Primary Amine and a Carboxylic Acid

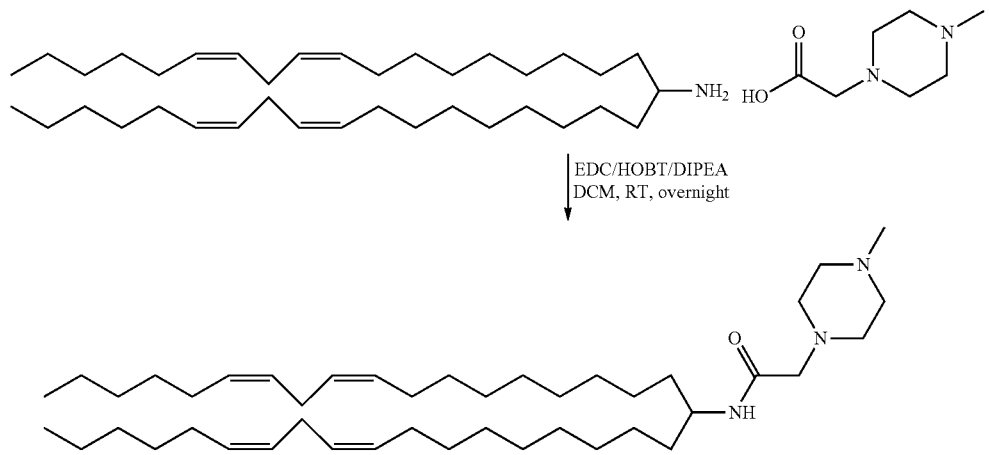

Figure 6:
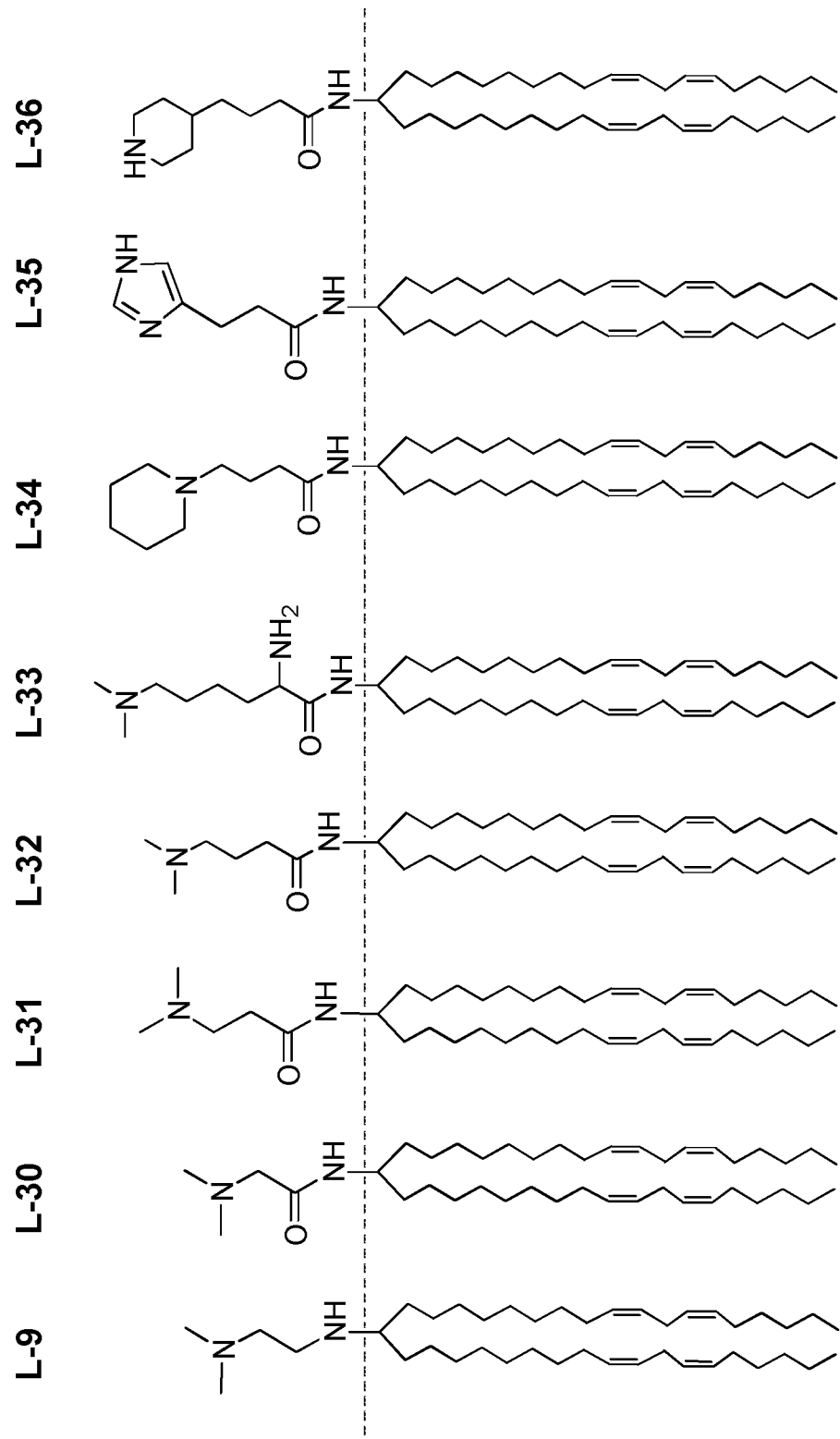
FIG. 6 shows exemplary amide analogs of L-9, including compounds L-30 to L-36.
Figure 7:
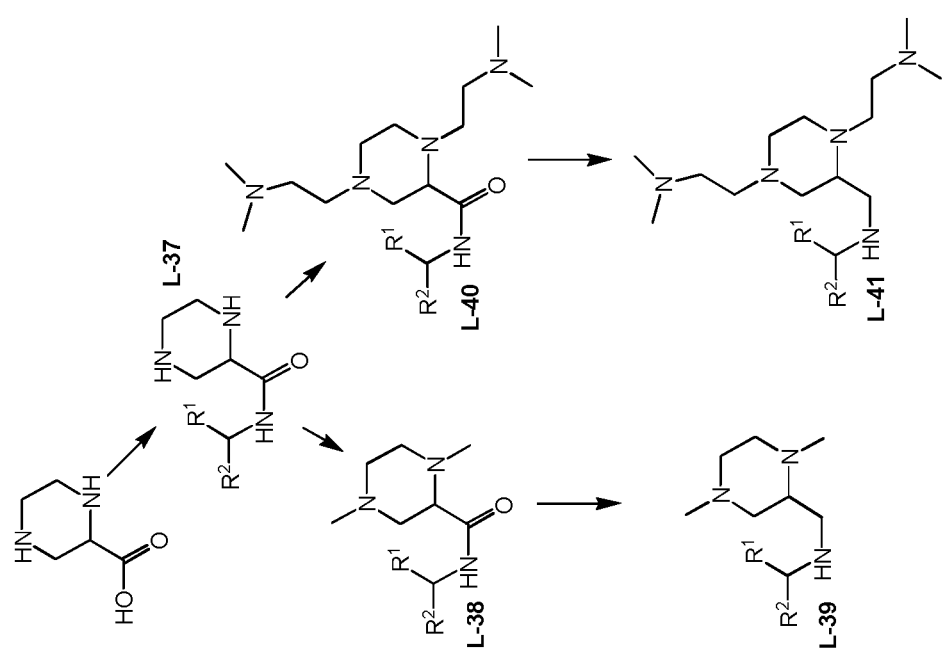
FIG. 7 shows compounds L-37 to L-41 having a piperazinyl group, where each $R^1$ and $R^2$ is, independently, any tail group described herein, such as optionally substituted $C_{11-24}$ alkyl, alkenyl, alkynyl, heteroalkyl, heteroalkenyl, or heteroalkynyl.
Figure 8:
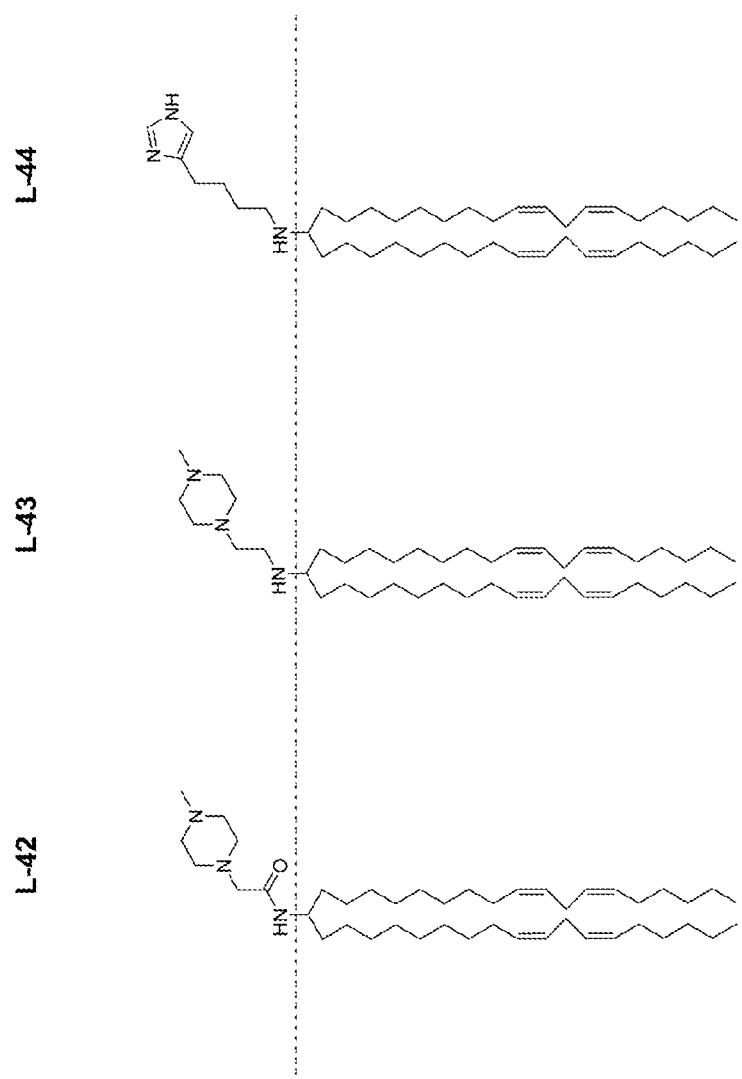
FIG. 8 shows additional exemplary amino amine cationic lipid structures L-42, L-43, and L-44.

By modifying the synthetic steps of this example, additional amide-amine lipids were prepared, such as those provided in FIG. 6-8.

Example 6: Preparation of Amine Lipid Formulations

To test the efficacy of lipids L-1 and L-2, formulations were prepared with a cationic lipid (DODMA), a neutral lipid (DSPC), a PEG-lipid conjugate (PEG-DMPE and PEG-DMG), and cholesterol with an RNAi agent (DsiRNA for HPRT1), having the following structure:

```
                                              (SEQ ID NO: 1)
5'-GCCAGACUUUGUUGGAUUUGAAAtt (SEQ ID NO: 2)
3'-UUCGGUCUGAAACAACCUAAACUUUAA,
``` where uppercase letters signify to RNA nucleotide, underlined uppercase letters signify a 2'-O-methyl-RNA nucleotide, and lowercase letters signify a DNA nucleotide.

Preparation of DsiRNA Strands: Oligonucleotide Synthesis and Purification

Individual RNA strands were synthesized and HPLC purified according to standard methods (Integrated DNA Technologies, Coralville, Iowa). For example, RNA oligonucleotides were synthesized using solid phase phosphoramidite chemistry, deprotected, and desalted on NAP-5 columns (Amersham Pharmacia Biotech, Piscataway, N.J.) using standard techniques (Damha and Olgivie, *Methods Mol. Biol.* 20:81, 1993; Wincott et al., *Nucleic Acids Res.* 23: 2677, 1995). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min. step-linear gradient. The gradient was from 90:10 Buffers A:B to 52:48 Buffers A:B, where Buffer A is 100 mM Tris pH 8.5 and Buffer B is 100 mM Tris pH 8.5, 1 M NaCl. Samples were monitored at 260 nm, and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 µm inner diameter and contained ssDNA 100R Gel (Beckman-Coulter). Typically, about 0.6 nmole of oligonucleotide was injected into a capillary, run in an electric field of 444 V/cm and detected by UV absorbance at 260 nm. Denaturing Tris-Borate-7 M-urea running buffer was purchased from Beckman-Coulter. Oligoribonucleotides were obtained that are at least 90% pure as assessed by CE for use in experiments described below. Compound identity was verified by matrix-assisted laser desorption ionization time-of-flight (MALDI-TOF) mass spectroscopy on a Voyager DETM Biospectometry Workstation (Applied Biosystems, Foster City, Calif.) following the manufacturer's recommended protocol. Relative molecular masses of all oligomers were obtained, often within 0.2% of expected molecular mass.

Preparation of DsiRNA Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5 minutes in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Preparation of Vesicle-Based Lipid Formulation

Lipid particles were prepared with the mol % provided in Table 5. The total lipid to DsiRNA ratio was about 1:7.

TABLE 5

| Formulations | Composition | | | |
|---|---|---|---|---|
| L-1v | L-1 (57.2%) | PEG-DMPE (3%) | DSPC (7.1%) | Cholesterol (32.7%) |
| L-2v | L-2 (57.2%) | PEG-DMPE (3%) | DSPC (7.1%) | Cholesterol (32.7%) |
| L-5v | L-5 (57.2%) | PEG-DMPE (3%) | DSPC (7.1%) | Cholesterol (32.7%) |
| L-6v | L-6 (57.2%) | PEG-DMPE (3%) | DSPC (7.1%) | Cholesterol (32.7%) |
| L-30v | L-30 (57.2%) | PEG-DMPE (3%) | DSPC (7.1%) | Cholesterol (32.7%) |

Preparation of RNA-Binding Agent and Transfection Lipid Formulation

Lipid particles were prepared with the mol % provided in Table 6. The total lipid to DsiRNA ratio was about 1:20.

TABLE 6

| Formulations | RNA-binding agents | | Transfection lipids | | | |
|---|---|---|---|---|---|---|
| L-1 | DODMA (25.9%) | PEG-DMPE (2.9%) | L-1 (21.6%) | PEG-DMG (2.8%) | DSPC (13.8%) | Cholesterol (33.0%) |
| L-2 | DODMA (25.9%) | PEG-DMPE (2.9%) | L-2 (21.6%) | PEG-DMG (2.8%) | DSPC (13.8%) | Cholesterol (33.0%) |
| DLinDMA | DODMA (25.9%) | PEG-DMPE (2.9%) | DLinDMA (21.6%) | PEG-DMG (2.8%) | DSPC (13.8%) | Cholesterol (33.0%) |
| DLin-KC2-DMA | DLinDMA (25.9%) | PEG-DMPE (2.9%) | DLin-KC2-DMA (21.6%) | PEG-DMG (2.8%) | DSPC (13.8%) | Cholesterol (33.0%) |

In Tables 5 and 6, PEG-DMPE is 1,2-dimyristoyl-sn-glycero-3-phosphoethanolamine-N-[methoxy(polyethylene glycol)-2000] and PEG-DMG is (R)-3-[(ω-methoxy-PEG2000-carbamoyl)]-1,2-di-O-tetradecyl-sn-glyceride.

Example 7: In Vitro Performance of Amine Lipid Formulations

To assess the efficacy of various lipid formulations, in vitro assays were conducted with DsiRNA molecules that target HPRT1. The lipid formulations were prepared with DsiRNA for HPRT1, as described above in Example 6.

Cell Culture and RNA Transfection

HeLa cells were obtained from ATCC and maintained in Dulbecco's modified Eagle medium (HyClone) supplemented with 10% fetal bovine serum (HyClone) at 37° C. under 5% $CO_2$. dsRNA-cationic lipid formulations of the invention were transfected into HeLa cells via incubation with the formulations of the invention at a final concentration of 1 nM, 5 nM, or 25 nM. Lipofectamine™ RNAiMAX (Invitrogen) dsRNAs were used as positive controls at 0.1 nM or 1 nM. Briefly, 2.5 µL of a 0.2 µM or 0.02 µM stock solution of each dsRNAs was mixed with 47.5 µL of Opti-MEM I (Invitrogen). For Lipofectamine™ control, 2.5 µL of a 0.2 µM or 0.02 µM stock solution of each dsRNAs was mixed with 46.5 µL of Opti-MEM I (Invitrogen) and 1 µL of Lipofectamine™ RNAiMAX. The resulting 50 µL mix was added into individual wells of 12-well plates and incubated for 20 min at RT to allow dsRNA:Lipofectamine™ RNAiMAX complexes to form.

Meanwhile, HeLa cells were trypsinized and resuspended in medium at a final concentration of about 367 cells/µL. Finally, 450 µL of the cell suspension were added to each well (final volume 500 µL) and plates were placed into the incubator for 24 hours. For dose response studies, the concentrations of dsRNAs were varied from initially 10 pM to 100 nM. For the time course study, incubation times of about 4 hours to about 72 hours were studied.

Assessment of Inhibition

Target gene knockdown was determined by qRT-PCR, with values normalized to HPRT expression control treatments, including Lipofectamine™ RNAiMAX alone (vehicle control) or untreated.

RNA Isolation and Analysis

Cells were washed once with 2 mL of PBS, and total RNA was extracted using RNeasy Mini Kit™ (Qiagen) and eluted in a final volume of 30 μL. 1 μg of total RNA was reverse-transcribed using Transcriptor 1$^{st}$ Strand cDNAKit™ (Roche) and random hexamers following manufacturer's instructions. One-thirtieth (0.66 μL) of the resulting cDNA was mixed with 5 μL of IQ Multiplex Powermix (Bio-Rad) together with 3.33 μL of $H_2O$ and 1 μL of a 3 μM mix containing primers and probes specific for human genes HPRT-1 (accession number NM_000194) target sequences.

Quantitative RT-PCR

A CFX96 Real-time System with a C1000 Thermal cycler (Bio-Rad) was used for the amplification reactions. PCR conditions were: 95° C. for 3 minutes; and then cycling at 95° C., 10 seconds; and at 55° C., 1 minute for 40 cycles. Each sample was tested in triplicate. Relative HPRT mRNA levels were normalized to target mRNA levels and compared with mRNA levels obtained in control samples treated with the transfection reagent alone, or untreated. Data were analyzed using Bio-Rad CFX Manager version 1.0 software. Expression data are presented as a comparison of the expression under the treatment of amino-amine cationic lipid formulation of dsRNA versus the dsRNA formulation without the amino-amine cationic lipid.

Results

Figure 10:
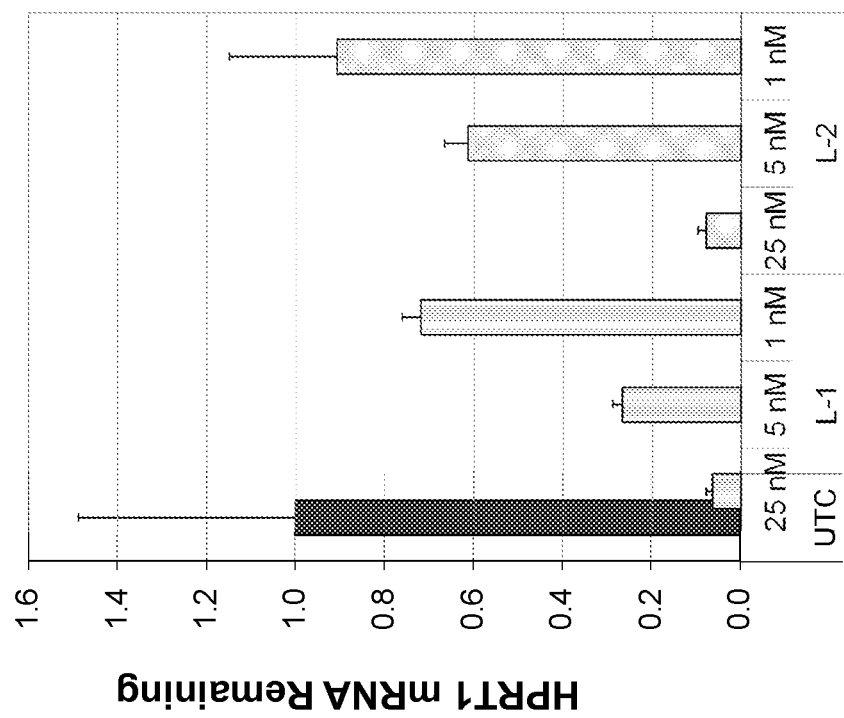
FIG. 10 is a graph showing in vitro knockdown of lipid particles containing compounds L-1 or L-2, as compared to an untreated control.

FIG. 10 provides results of in vitro knockdown using lipid particles containing the amino-amine lipids L-1 or L-2. Overall, both L-1 and L-2 effectively inhibited target mRNA levels when administered to HeLa cells. In particular, L-1 provided about 70% remaining mRNA levels at the lowest concentration of 1 nM. Accordingly, the amino-amine lipids provided effective delivery of the RNAi agents when administered to HeLa cells via transfection. Thus, any of the compounds of the invention, e.g., any lipid or formulations thereof, would be useful for delivery of a polyanionic payload, e.g., an RNAi agent or antisense payload.

Example 8: In Vivo Performance of Amine Lipid Formulations

To further assess the performance of the lipids, in vivo experiments were performed with formulations having DsiRNA for HPRT1.

Formulations were prepared with the following approximate percentages: 20 mol % of one of either L-1, L-2, L-5, L-6, L-7, L-8, L-22, or L-30; 26 mol % of DODMA; 3 mol % of PEG2000-DMPE; 3 mol % of PEG2000-DMG; 13 mol % of DSPC; and 33 mol % of cholesterol. The formulation further included a DsiRNA:total lipid ratio of about 1:20 (w/w).

Figure 11:
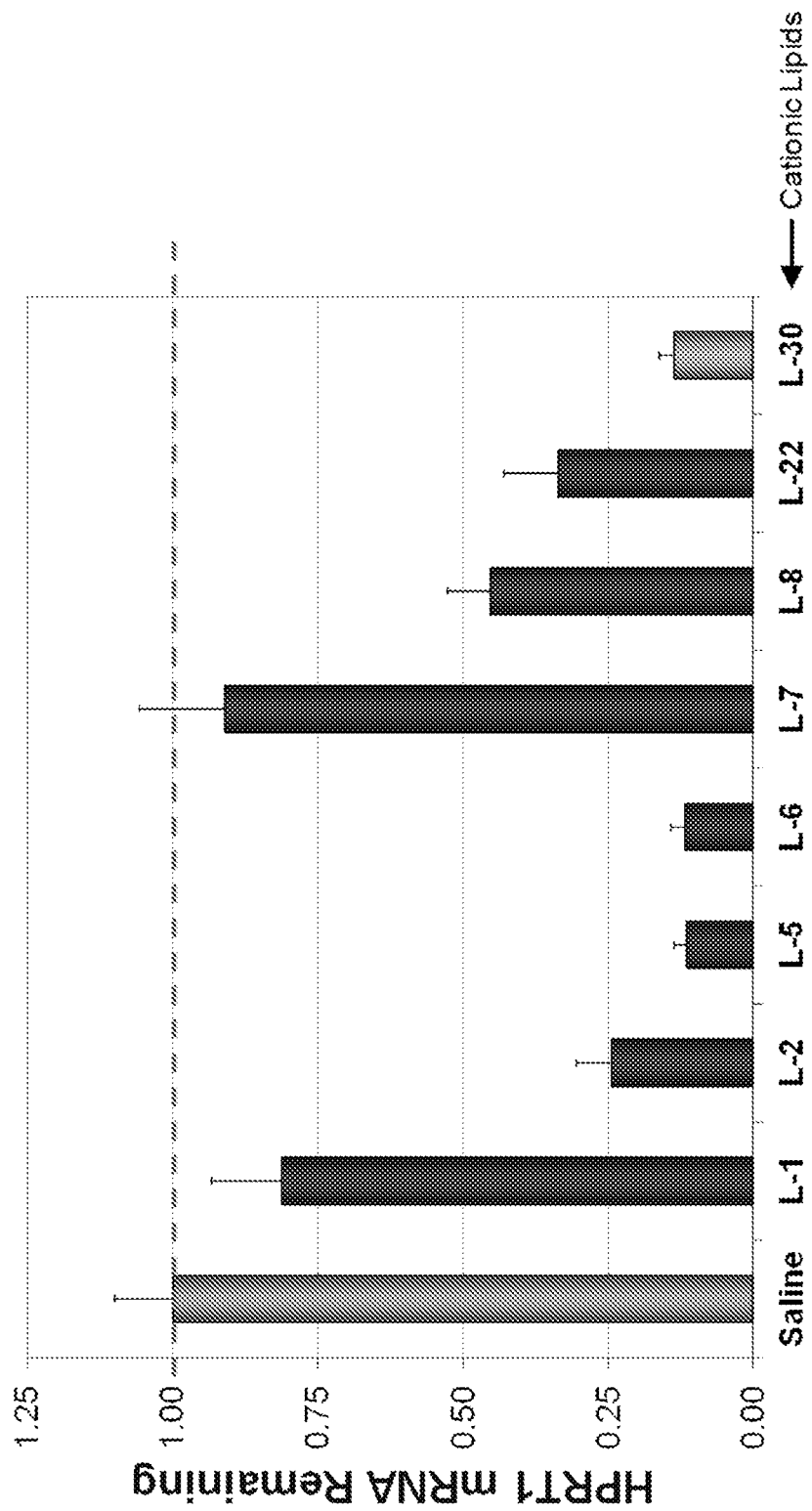
FIG. 11 is a graph showing in vivo knockdown of HPRT1 mRNA in mouse liver using a single dose of lipid particles including L-1, L-2, L-5, L-6, L-7, L-8, L-22, or L-30 and 5 mg/kg of DsiRNA followed by tissue harvesting after 48 hours.
Figure 12:
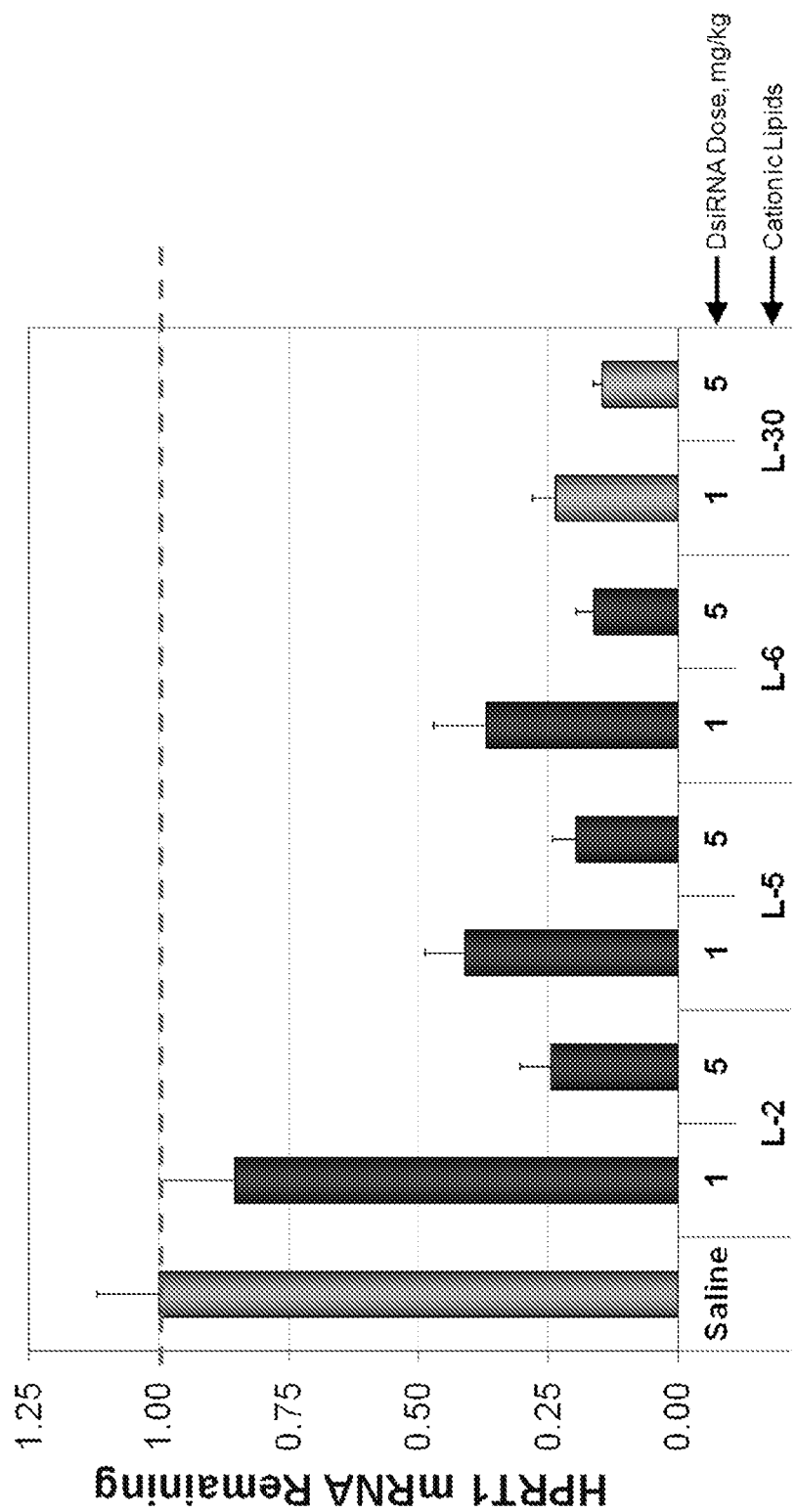
FIG. 12 is a graph showing in vivo knockdown of HPRT1 mRNA in mouse liver using a single dose of lipid particles including L-2, L-5, L-6, or L-30 and either 1 mg/kg or 5 mg/kg of DsiRNA followed by tissue harvesting after 48 hours.

Approximately 4-week old CD1 female mice were administered a single dose (either 1 mg/kg or 5 mg/kg) of the lipid particle formulation with a dosing volume of 10 μL/g of body weight by intravenous administration via a tail vein. After 48 hours (post-dosing), tissues were collected in RNALater (Qiagen). In the end point analysis, the total RNA was isolated from the mouse liver for RT-qPCR. The RNA sample was heated at 70° C., for 5 minutes with Oligo(dT) primers before RT. In the PCR reaction, mHPRT expression was normalized with RPL23 (a housekeeping gene, used as a control herein). FIGS. 11 and 12 show data with error bars with mean±SD for n=5 animals/group.

In a first set of experiments, the dosage of the lipid formulation was 5 mg/kg in a single dose (FIG. 11). At this dosage, compounds L-1 and L-7 provided remaining mRNA levels of about 80% to about 90%. Addition of an oxo group in the head group, such as in L-30, provided a drastic increase in gene silencing, as evidenced by remaining mRNA levels of about 15%. In addition, compounds having a heterocyclyl in the head group (e.g., L-2, L-5, L-6, L-8, and L-22) provided compounds having remaining mRNA levels of about 15% to about 45%. The % mRNA knockdown for various formulations is shown in Table 7. Table 7 additionally shows the pKa value for each of the lipids, as measured by the TNS fluorescence method.

To determine pKa values of the cationic lipids of the invention, formulations (concentration of 1 mM) were incubated in phosphate buffer at different pH values, to which TNS dissolved in DMSO was added (resulting final concentration of 6 μM TNS). Fluorescence of the resulting solution was measured on a SpectraMax® M3 fluorescence plate reader with excitation wavelength of 325 nm and emission wavelength of 435 nm. The measured fluorescence of TNS was fitted with a three-parameter sigmoidal function shown in equation 1.

$$\text{Function}(f) = \frac{a}{\left(1 + \exp\left(\frac{pH - pKa}{b}\right)\right)} \quad \text{(equation 1)}$$

The pH at which half of the maximum fluorescence was reached was reported as the apparent pKa of the formulation, where a and b are dimensionless parameters reflecting the maximum observed fluorescence and slope of the sigmoidal function, respectively.

TABLE 7

| Lipid Formulation | TNS pKa Value | % mRNA Knockdown |
|---|---|---|
| L-1 | 7.6 | 18.7 |
| L-2 | 6.7 | 75.6 |
| L-5 | 6.4 | 88.5 |
| L-6 | 5.6 | 88.2 |
| L-7 | 7.1 | 8.9 |
| L-8 | 6.7 | 54.6 |
| L-22 | 7.0 | 66.3 |
| L-24 | 5.7 | 74.1 |
| L-25 | 6.5 | 76.8 |
| L-26 | 7.1 | 63.6 |
| L-30 | 5.8 | 86.4 |
| L-31 | 6.9 | 83.6 |
| L-32 | 7.0 | 41.0 |
| L-35 | 6.5 | 26.1 |
| L-42 | 6.7 | 66.6 |

In a second set of experiments, compounds L-2, L-5, L-6, and L-30 were assessed at dosage of 1 mg/kg or 5 mg/kg in a single dose (FIG. 12). In particular, L-5, L-6, and L-30 provided effective gene silencing at the lower dose of 1 mg/kg. Overall, these data provide various lipid compounds and dosages that are effective inhibitors of target RNA levels in an in vivo model.

In order to assess the tolerability of a lipid formulation containing an amino-amine or amino-amide cationic lipid of the invention and a dsRNA, female CD-1 mice were injected with L-6 and L-30 formulations [administered in 2 doses (qod) at 10 mg/kg DsiRNA dose, about 200 mg/kg total lipid dose each] and serum samples were collected 48 hours after the second dose. Serum samples were tested for a panel of clinical chemistry assessments, including liver function tests (LFTs) via measurement of enzymes alanine transaminase (ALT) and aspartate transaminase (AST). Phosphate buffered saline (PBS) was used as vehicle control group. ALT and AST elevation was <3x of PBS group for formulations L-6 and L-30. There were also no changes in body weight or liver observed for L-6 and L-30 formulations. Thus, L-6 and L-30 formulations were well-tolerated. Thus, any of the lipids described herein, and formulations thereof, would be useful for the delivery of one or more agent, e.g., polyanionic or antisense payloads.

Example 9: Use of a Lipid Formulation with dsRNA to Reduce Expression of a Target Gene in a Subcutaneous Animal Tumor Model In order to assess the efficiency of delivery and subsequent functionality of a lipid formulation containing an amino-amine or amino-amide cationic lipid and a dsRNA, subcutaneous (s.c.) tumor models (Judge et al., *J. Clin. Invest.* 119:661, 2009) are used with certain modifications. Hep3B tumors are established in male nu/nu mice by s.c. injection of $3\times10^6$ cells in 50 µL PBS into the left-hind flank. Mice are randomized into treatment groups 10-17 days after seeding as tumors became palpable. The lipid formulation of a dsRNA or vehicle control is administered by standard intravenous (i.v.) injection via the lateral tail vein, calculated based on a mg dsRNAs/kg body weight basis according to individual animal weights. Tumors are measured in 2 dimensions (width×length) to assess tumor growth using digital calipers. Tumor volume is calculated using the equation x*y*y/2, where x=largest diameter and y=smallest diameter, and is expressed as group mean±SD. Tumor tissues are also removed from the animals of different treatment groups and gene knockdown is confirmed. Tumor volume, survival and RNA expression data are presented as a comparison between the treatments of the lipid formulation of dsRNA versus a dsRNA formulation without an amino-amine or amino-amide cationic lipid.

Example 10: Use of a Lipid Formulation with dsRNA to Reduce Expression of a Target Gene in Hep3B Orthotopic Liver Tumor Model In order to assess the efficiency of targeting and subsequent functionality of an amino-amine or amino-amide cationic lipid formulation of dsRNA, intrahepatic tumor models (Judge et al., *J. Clin. Invest.* 119:661, 2009) were utilized with certain modifications. Liver tumors were established in mice by direct intrahepatic injection of Hep3B tumor cells. Male nu/nu mice were used as hosts for the Hep3B tumors. Maintaining the mice under anesthesia using 2,2,2-tribromoethanol (Sigma), a single 1-cm incision across the midline was made below the sternum, and the left lateral hepatic lobe was exteriorized. Approximately $2\times10^6$ Hep3B cells suspended in 40 µL of 50% PBS/50% Matrigel™ (BD) were injected slowly into the lobe at a shallow angle using a Hamilton syringe and a 30-gauge needle. A swab was then applied to the puncture wound to stop any bleeding prior to suturing. Mice were allowed to recover from anesthesia in a sterile cage and monitored closely for 2-4 hours before being returned to conventional housing. About three weeks after tumor implantation, mice were randomized into treatment groups. Mice (n=7 per group) received: (1) the amino-amine or amino-amide lipid formulation of dsRNA; (2) dsRNA formulation without the amino-amine or amino-amide cationic lipid; or (3) vehicle control, as administered by standard intravenous (i.v.) injection via the lateral tail vein. The dose was calculated based on mg of dsRNAs/kg of body weight basis according to individual animal weights.

Figure 13:
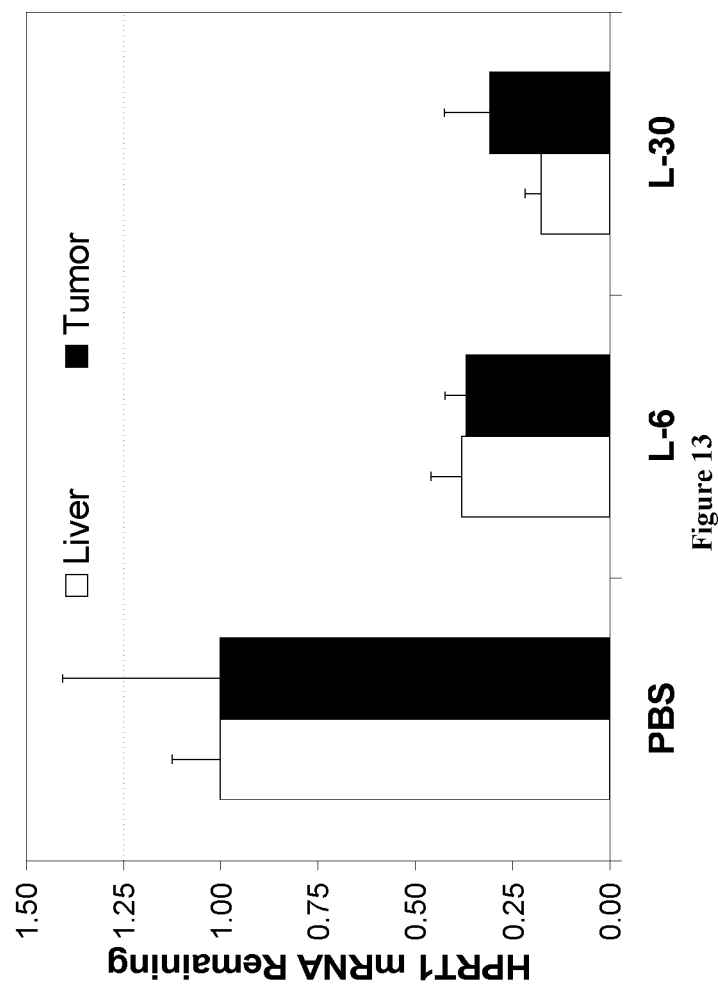
FIG. 13 is a graph showing in vivo knockdown of HPRT1 mRNA in mouse liver and orthotopic Hep3B tumor using two doses of lipid particles formulated with L-6 or L-30 and 5 mg/kg of DsiRNA followed by tissue harvesting after 48 hours.

For experiments that generated the results shown in FIG. 13, animals were dosed at 5 mg/kg DsiRNA with L-6- or L-30-formulated lipid particles. Table 8 presents specific compositions of lipid formulations comprising the L-6 and L-30 lipids used in the instant studies.

TABLE 8

| Formulations | RNA-binding agents | | Transfection lipids | | | |
|---|---|---|---|---|---|---|
| L-6 | DODMA (25.9%) | PEG-DMPE (2.9%) | L-6 (21.6%) | PEG-DSPE (2.8%) | DSPC (13.8%) | Cholesterol (33.0%) |
| L-30 | DODMA (25.9%) | PEG-DMPE (2.9%) | L-30 (21.6%) | PEG-DSPE (2.8%) | DSPC (13.8%) | Cholesterol (33.0%) |

Body weights were monitored throughout the duration of the study as an indicator of developing tumor burden and treatment tolerability. For efficacy studies, defined humane end points were determined as a surrogate for survival. Assessments were made based on a combination of clinical signs, weight loss, and abdominal distension to define the day of euthanization due to tumor burden. Tumor tissues were removed from the animals of different treatment groups and gene knockdown was confirmed.

As shown in FIG. 13, both L-6 and L-30 formulations tested were remarkably effective at delivery of a formulated anti-HPRT1 DsiRNA payload to both liver and orthotopic Hep3B tumor tissues. Specifically, greater than 50% knockdown (and in certain cases, 60-80% knockdown) of HPRT1 target mRNA was observed in both liver and orthotopic Hep3B tumor tissues, as compared to a PBS control. Accordingly, any of the lipids, or formulations thereof, would be useful in reducing the expression of a target gene (e.g., a target gene associated with cancer).

Example 11: Use of a Lipid Formulation with dsRNA to Reduce Expression of a Target Gene in HepG2 Orthotopic Liver Tumor Model In order to assess the efficiency of targeting and subsequent functionality of an amino-amine or amino-amide cationic lipid formulation of dsRNA, a second intrahepatic tumor model was utilized. Liver tumors were established in mice by direct intrahepatic injection of HepG2 tumor cells. Female nu/nu mice were used as hosts for the HepG2 tumors. Maintaining the mice under anesthesia using Avertin (Sigma), a single 1-cm incision across the midline was made below the sternum, and the left lateral hepatic lobe is exteriorized. Approximately $3\times10^6$ HepG2 cells suspended in 60 µL of 50% PBS/50% Matrigel™ (BD) are injected slowly into the lobe at a shallow angle using a Hamilton syringe and a 30-gauge needle. A swab was then applied to the puncture wound to stop any bleeding prior to suturing. Mice were allowed to recover from anesthesia in a sterile cage and monitored closely for 2-4 hours before being returned to conventional housing. About three weeks after tumor implantation, mice were randomized into treatment groups. Mice (n=6-7 per group) received: (1) the amino-amine or amino-amide lipid formulation of dsRNA; (2) dsRNA formulation without the amino-amine or amino-amide cationic lipid; or (3) vehicle control, as administered by standard intravenous (i.v.) injection via the lateral tail vein. The dose was calculated based on mg of dsRNAs/kg of body weight basis according to individual animal weights. Experiments that generated the results shown in FIG. 14 were dosed at 5 mg/kg DsiRNA in L-6- or L-30-formulated lipid particles. Table 8 presents specific compositions of lipid formulations comprising the L-6 and L-30 lipids employed in the instant studies. Body weights were monitored throughout the duration of the study as an indicator of developing tumor burden and treatment tolerability. For efficacy studies, defined humane end points were determined as a surrogate for survival. Assessments were made based on a combination of clinical signs, weight loss, and abdominal distension to define the day of euthanization due to tumor burden. Tumor tissues were removed from the animals of different treatment groups and gene knockdown was confirmed.

Figure 14:
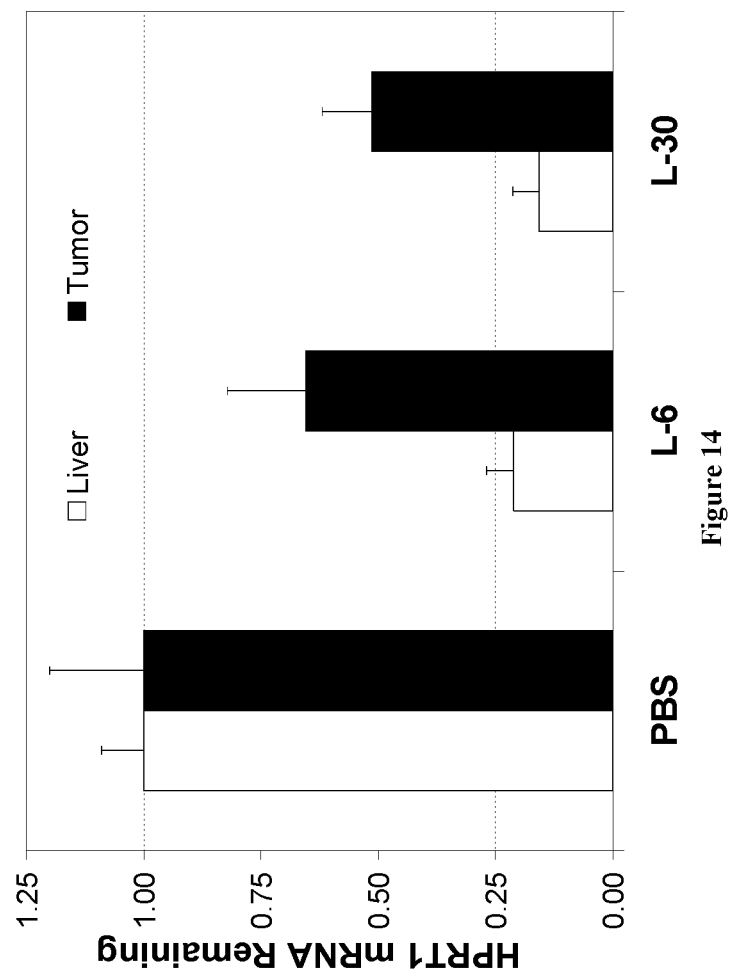
FIG. 14 is a graph showing in vivo knockdown of HPRT1 mRNA in mouse liver and orthotopic HepG2 tumor using two doses of lipid particles formulated with L-6 or L-30 and 5 mg/kg of DsiRNA followed by tissue harvesting after 48 hours.

As shown in FIG. 14, both L-6 and L-30 formulations tested were remarkably effective at delivery of a formulated anti-HPRT1 DsiRNA payload to liver tissues. Meanwhile, 20-50% levels of HPRT1 target mRNA knockdown were observed for both formulations in orthotopic HepG2 tumor tissues. The above results identified the L-6 and L-30 formulations examined herein as effective dsRNA delivery vehicles, for delivery to normal liver and at least certain tumor tissues (e.g., orthotopic Hep3B tumor and, to lesser extent, orthotopic HepG2 tumor). Accordingly, any of the lipids, or formulations thereof, would be useful in reducing the expression of a target gene (e.g., a target gene associated with cancer).

Functionality of the lipid formulation of dsRNA for tumor cell uptake can also be tested by labeling the lipid and/or dsRNA with fluorescent tags and performing fluorescent biodistribution studies using a live-animal imaging system (Xenogen or BioRad) (Eguchi et al., Nat. Biotechnol. 27:567, 2009). Using this methodology, and by comparing with dsRNA formulation alone, the ability of the amino-amine or amino-amide cationic lipid to facilitate tumor cell internalization for dsRNA is confirmed. By contrast, dsRNA formulation alone, used as a control in this study, is unable to be taken up and delivered to the same extent to tumor surface. Efficacy end points, RNA expression, and biodistribution data are presented as a comparison between the treatments of the lipid formulation of dsRNA versus the dsRNA formulation without the amino-amine or amino-amide cationic lipid.

Figure 15:
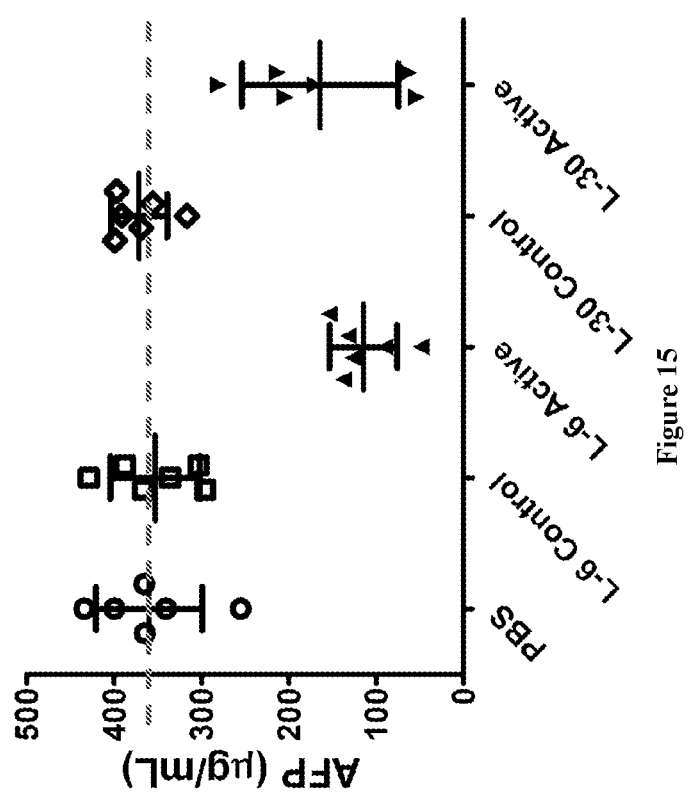
FIG. 15 is a graph showing the effect of lipid particle formulations L-6 and L-30 with an active DsiRNA ("L-6 Active" and "L-30 Active") on serum α-fetoprotein (AFP) levels in an in vivo Hep3B model. Controls are provided for formulations without DsiRNA ("L-6 Control" and "L-30 Control") and buffer ("PBS").
Figure 16:
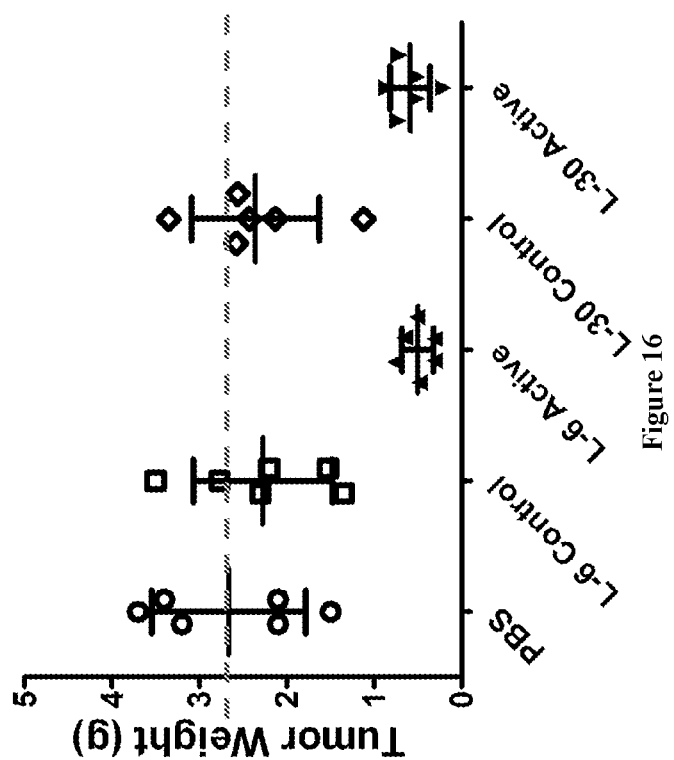
FIG. 16 is a graph showing the effect of lipid particle formulations L-6 and L-30 with an active DsiRNA ("L-6 Active" and "L-30 Active") on tumor weight in an in vivo Hep3B mode. Controls are provided for formulations without DsiRNA ("L-6 Control" and "L-30 Control") and buffer ("PBS").

Example 12: Hepatocellular Carcinoma Anti-Tumor Efficacy with Lipid Formulations Liver tumors were established in mice by direct intrahepatic injection of Hep3B tumor cells as described in Example 10. About two weeks after tumor implantation, mice were randomized into treatment groups. Mice (n=6 per group) received: either (1) the amino-amine or amino-amide lipid formulation of a control dsRNA; (2) the amino-amine or amino-amide lipid formulation of an active dsRNA; or (3) vehicle control, as administered by standard intravenous (i.v.) injection via the lateral tail vein. The dose was calculated based on mg of dsRNAs/kg of body weight basis according to individual animal weights. In the experiments that generated the results shown in FIGS. 15 and 16, animals were dosed at 5 mg/kg DsiRNA with L-6- or L-30-formulated lipid particles. Table 8 above presents specific compositions of lipid formulations comprising the L-6 and L-30 lipids used in the instant studies.

Body weights were monitored throughout the duration of the study as an indicator of developing tumor burden and treatment tolerability. For efficacy studies, defined humane end points were determined as a surrogate for survival. Assessments were made based on a combination of clinical signs, weight loss, and abdominal distension to define the day of euthanization due to tumor burden. Tumor tissues were removed from the animals of different treatment groups and tumor weights were measured to determine efficacy of different treatment groups. Serum α-fetoprotein (AFP) levels were also measured as a biomarker for tumor burden. Both L-6 and L-30 formulations with an active payload were remarkably effective in reducing serum AFP (FIG. 15) and tumor weight (FIG. 16), as compared to L-6 and L-30 formulations with a control payload and to a PBS control.

Example 13: Use of Different L-30 Lipid Formulations with dsRNA to Reduce Expression of Various Target Genes in Multiple Orthotopic Liver Cancer Models In order to assess whether the knockdown of HPRT1 in tumor relative to liver can be tuned with different formulations of L-30, the PEG-lipid content was adjusted. Table 9 provides specific compositions of lipid formulations comprising the L-30 lipid used in the instant studies. Experiments that generated the results shown in FIG. 18 were dosed at 1, 3, and 10 mg/kg of DsiRNA in L-30 [1] formulated lipid particle and 10 mg/kg of DsiRNA in L-30 [2] formulated lipid particle. Any useful solvent or solvent system can be used to introduce the RNA-binding agents and the DsiRNA into the formulation, including solvents and solvent systems (e.g., aqueous and/or non-aqueous solvent(s)) that are the same or different as that for the transfection lipids.

Figure 18:
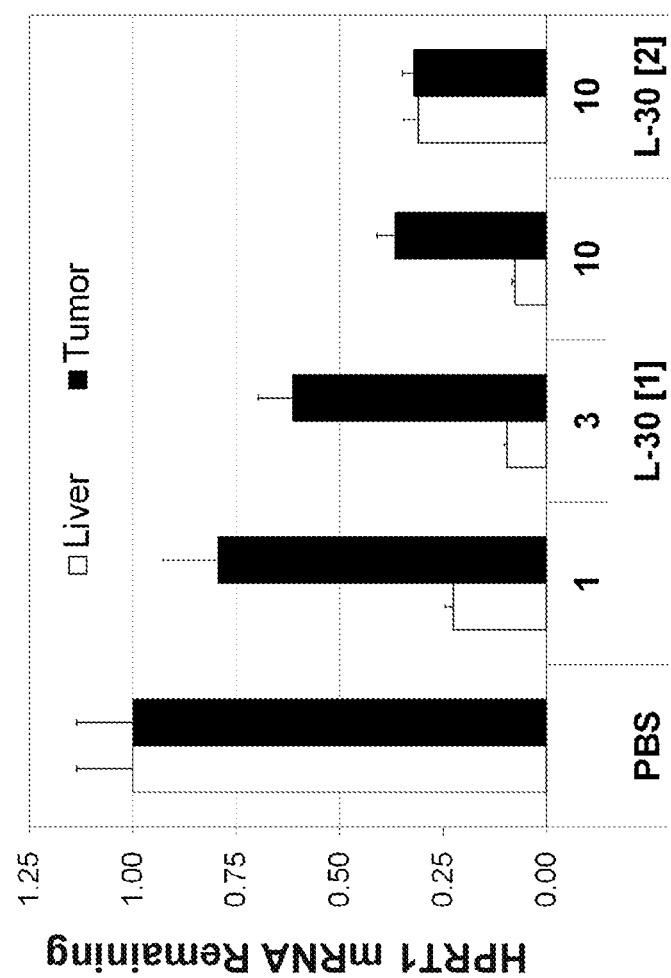
FIG. 18 is a graph showing in vivo knockdown of HPRT1 mRNA in mouse liver and orthotopic Hep3B tumor (0.5g±0.1) using a single IV dose of lipid particles including L-30 and either 1, 3, or 10 mg/kg of DsiRNA followed by tissue harvesting after 48 hours. N=7/group liver and tumor (mean with SEM). Two formulations were tested: L-30 [1] and L-30 [2], as described herein.

As shown in FIG. 18, both L-30 [1] and L-30 [2] formulations were effective at delivery of a formulated anti-HPRT1 DsiRNA payload to liver tissues and in orthotopic Hep3B tumor tissues. Meanwhile, liver knockdown is significantly reduced without adversely affecting tumor knockdown in the L-30 [2] compared to L-30 [1] formulations with 10 mg/kg of DsiRNA. These results indicate that increasing the PEG-lipid content in the lipid formulations can affect the delivery of the lipid particles and subsequently the knockdown of a target gene to certain tissues.

Figure 19:
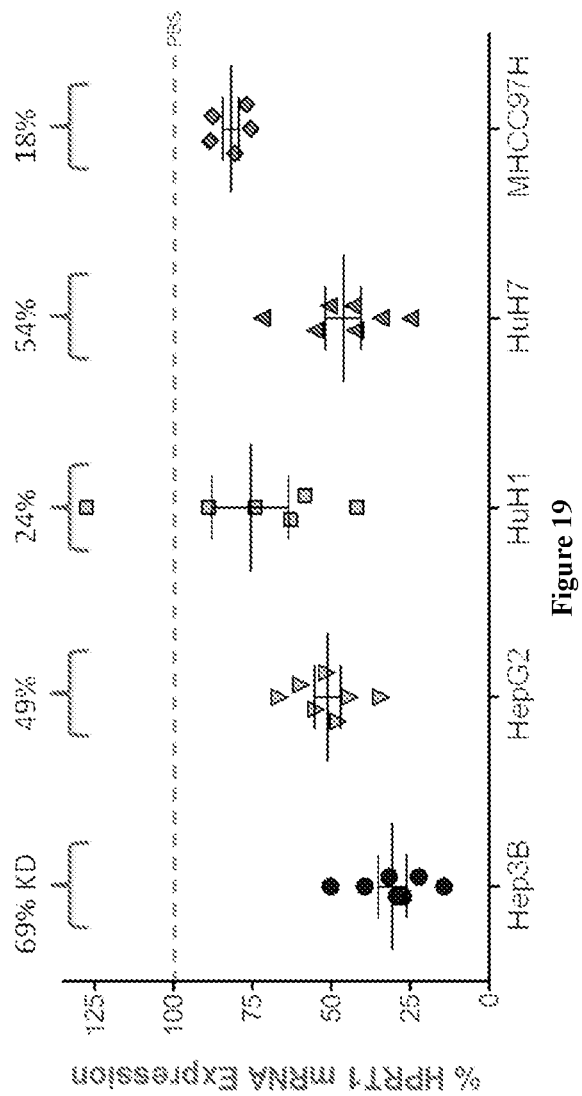
FIG. 19 is a graph showing in vivo knockdown of HPRT1 mRNA in multiple orthotopic liver cancer models using a single dose of lipid particles with the L-30 [1] formulation and DsiRNA. Hep3B and HepG2 models were implanted as cell suspensions; and HuH1, HuH7, and MHCC$_{97}$H were implanted as trocar fragments. N=5-7/group, IV at 5 mg/kg, Q2Dx1. Target knockdown in all groups were significant relative to PBS ($p<0.05$).
Figure 20:
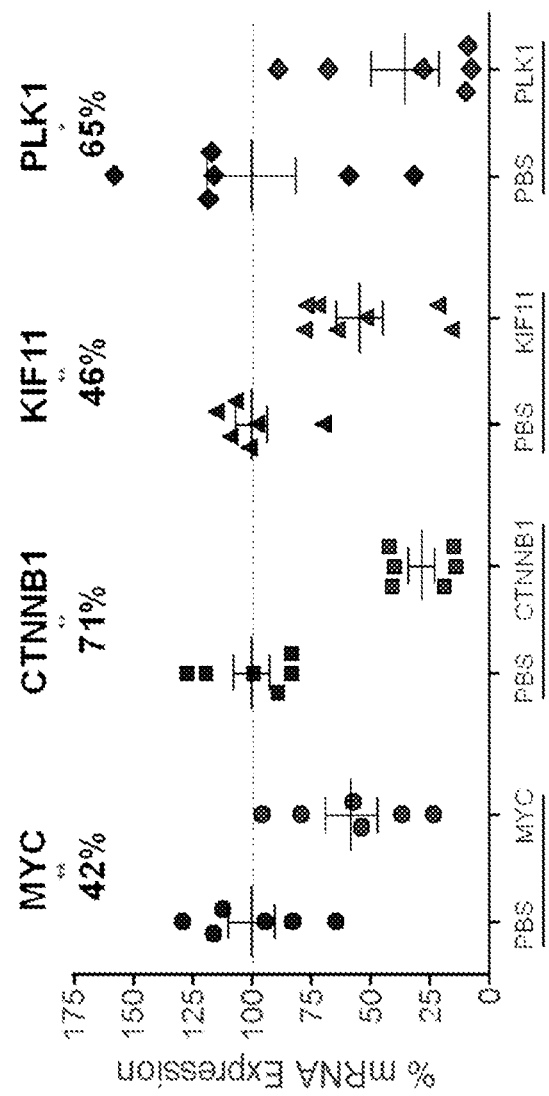
FIG. 20 is a graph showing in vivo knockdown of various mRNA in an orthotopic Hep3B HCC tumor model using a single dose of lipid particles with the L-30 [1] formulation and various independent DsiRNAs. N=6-7/group, IV at 5 mg/kg, TIWx2; all with sorafenib were given by oral administration at 10 mg/kg, QDx14. **=$p<0.01$, *=$p<0.05$.

The effectiveness of the L-30 [1] formulation as a dsRNA delivery vehicle was tested in various orthotopic liver cancer models and with different dsRNAs. FIG. 19 show results generated from experiments using different liver cancer models showing that L-30 [1] was effective at delivery of a formulated anti-HPRT1 DsiRNA payload to all tested cancer models compared to control. FIG. 20 show results generated from experiments using L-30 [1] formulations containing multiple, independent DsiRNAs and knockdown of corresponding genes in an orthotopic Hep3B HCC tumor model. Accordingly, any of the lipids described herein can be used to replaced L-30 in the specific compositions of lipid formulations in Table 9 and any dsRNA can be used to reduce the expression of a target gene (e.g., a target gene associated with cancer or a disease described herein).

TABLE 9

|  | Lipids | L-30 [1][2] | L-30 [2][2] |
|---|---|---|---|
| RNA-binding agents | DODMA | 25.9 | 25.9 |
|  | PEG$_{2000}$-DMPE | 2.9 | 2.9 |
| Transfection lipids | L-30 | 21.6 | 21.6 |
|  | DSPC | 13.8 | 13.8 |
|  | Cholesterol | 33.0 | 28.8 |
|  | PEG$_{2000}$-DSPE | 2.8 | 7.0 |
| Mixing |  | Batch | Batch |
| Ethanol %[1] |  | 4% | 4% |
| LNP Buffer |  | Saline | Saline |

[1]Prior to purification;
[2]Lipid mole percentage

Figure 17:
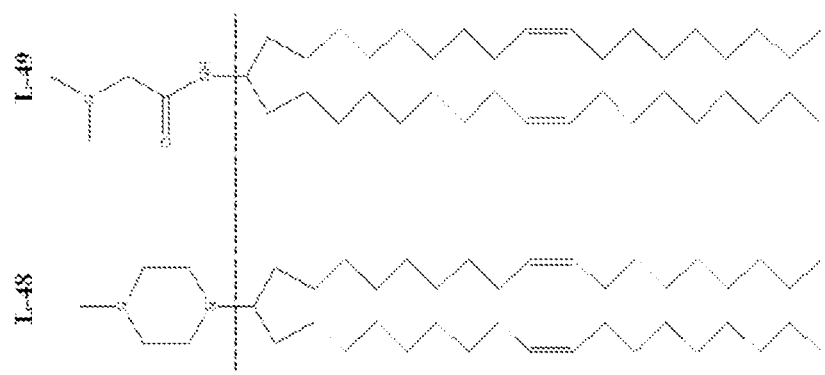
FIG. 17 shows exemplary compounds L-48 and L-49 having dioleyl tail groups.

Example 14: Use of Different L-30 Lipid Formulations with dsRNA to Reduce Expression of a Target Gene in Hep3B HCC Tumor Tissues In order to assess the efficiency of targeting and subsequent functionality of the L-30 formulation of dsRNA, L-30 formulations varying in lipid mole percentages were tested. Table 10 provides specific compositions of lipid formulations comprising L-30 as a transfection lipid. In particular, L-30 [E] and L-30 [G] formulations contain L-48 as an RNA-binding agent instead of DODMA. L-48 comprises a H-5 head group and dioleyl tail groups (FIG. 17). Any useful solvent or solvent system can be used to introduce the RNA-binding agents and the DsiRNA into the formulation, including solvents and solvent systems (e.g., aqueous and/or non-aqueous solvent(s)) that are the same or different as that for the transfection lipids.

Figure 21:
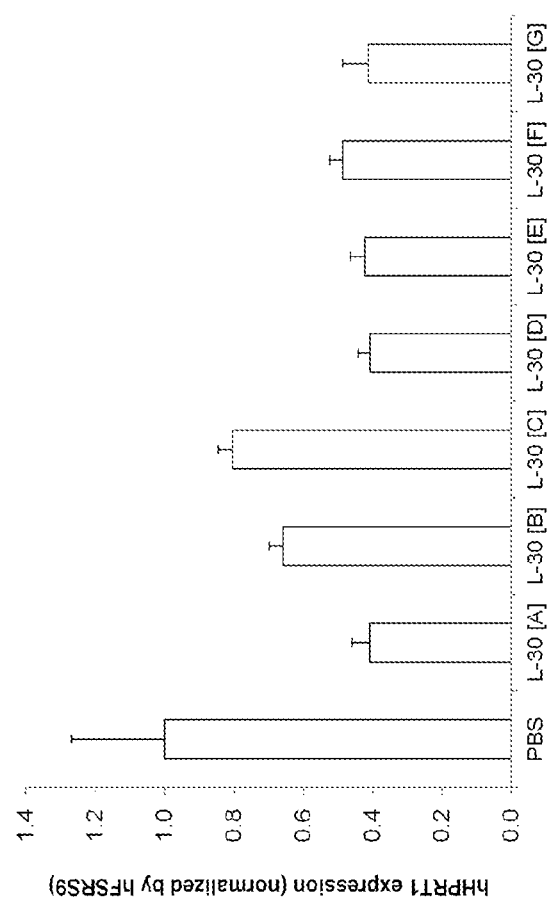
FIG. 21 is a graph showing in vivo knockdown of HPRT1 mRNA in Hep3B HCC tumor tissues with a single dose of lipid particles containing 5 mg/kg of DsiRNA in seven different formulations of L-30 ([A] through [G]) followed by tissue harvesting after 72 hours. Values in the bar with error represent mean+SEM (N=7/group).

The results of hHPRT1 knockdown in Hep3B HCC tumor tissues are shown in FIG. 21. All L-30 formulations (i.e., [A] through [G]) resulted in a decrease in hHPRT1 expression in tumor tissues compared to PBS control. In particular, L-30 [A] provided the greatest decrease in hHPRT1 expression followed by L-30 [D], L-30 [G], and L-30 [E].

TABLE 10

|  | Lipids | L-30 [A][2] | L-30 [B][2] | L-30 [C][2] | L-30 [D][2] | L-30 [E][2] | L-30 [F][2] | L-30 [G][2] |
|---|---|---|---|---|---|---|---|---|
| RNA-binding agents | DODMA | 25.9 | 25.9 | 25.7 | 25.9 | — | 25.9 | — |
|  | L-48 | — | — | — | — | 25.9 | — | 25.9 |
|  | PEG$_{2000}$-DMPE | 2.9 | 2.9 | 2.3 | 2.9 | 2.9 | 2.9 | 2.9 |
| Transfection lipids | L-30 | 21.6 | 21.0 | 21.2 | 21.6 | 21.6 | 21.6 | 21.6 |
|  | DSPC | 13.8 | 13.8 | 14.0 | 13.8 | 13.8 | 13.8 | 13.8 |
|  | Cholesterol | 33.0 | 34.0 | 34.3 | 33.0 | 33.0 | 33.0 | 33.0 |
|  | PEG$_{2000}$-DSPE | 2.8 | 2.4 | 2.4 | 2.8 | 2.8 | 2.8 | 2.8 |
| Mixing |  | Batch | Batch | Batch | Batch | Batch | In-line | Batch |
| Ethanol %[1] |  | 4% | 4% | 4% | 4% | 4% | 4%[3] | 4% |
| LNP Buffer |  | PBS | PBS | PBS | Saline | PBS | PBS | Saline |

[1]Prior to purification;
[2]Lipid mole percentage;
[3]Same formulation with 8% ethanol was also successfully prepared

Example 15: Use of Different L-6 and L-30 Lipid Formulations with dsRNA to Reduce Expression a Target Gene in Lung and Prostate Tumor Tissues In order to assess the efficiency of targeting and subsequent functionality of different L-6 and L-30 formulations, HPRT1 mRNA knockdown was tested in various tumor tissues. Table 9, 10, and 11 provide specific compositions of lipid formulations comprising the L-6 and L-30 lipids used in the instant studies. Any useful solvent or solvent system can be used to introduce the RNA-binding agents and the nucleic acid payload (e.g., DsiRNA) into the formulation, including solvents and solvent systems (e.g., aqueous and/or non-aqueous solvent(s)) that are the same or different as that for the transfection lipids.

Figure 22:
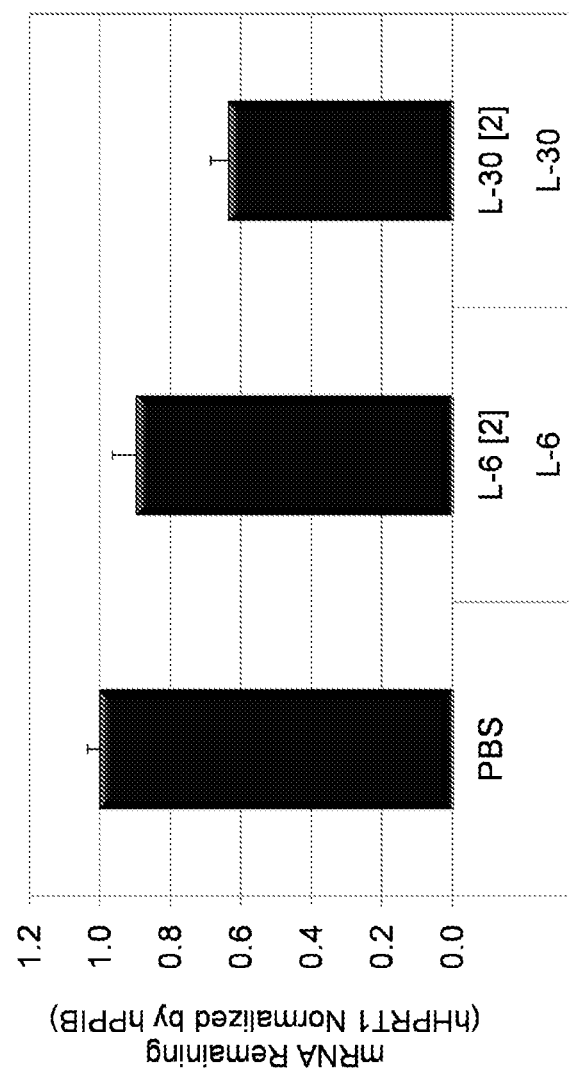
FIG. 22 is a graph showing in vivo knockdown of HPRT1 mRNA in H1975 NSCLC SC xenograft lung tumor tissues with a dose of lipid particles containing 10 mg/kg of DsiRNA at days 1 and 3 in two formulations, L-6 [2] and L-30 [2], followed by tissue harvesting at day 5. Values in the bar with error represent mean+SEM (N=7/group).

Experiments that generated FIG. 22 were dosed at 10 mg/kg DsiRNA in L-6 [2] and L-30 [2] formulated lipid particles and administered on days 1 and 3 of the experiment. The tumors were harvested on day 5. Knockdown of hHPRT1 mRNA was measured in H1975 NSCLC lung tumor tissues. A greater level of HPRT1 target mRNA knockdown was observed for the L-30 [2] formulation compared to the L-6 [2] formulation.

Figure 23:
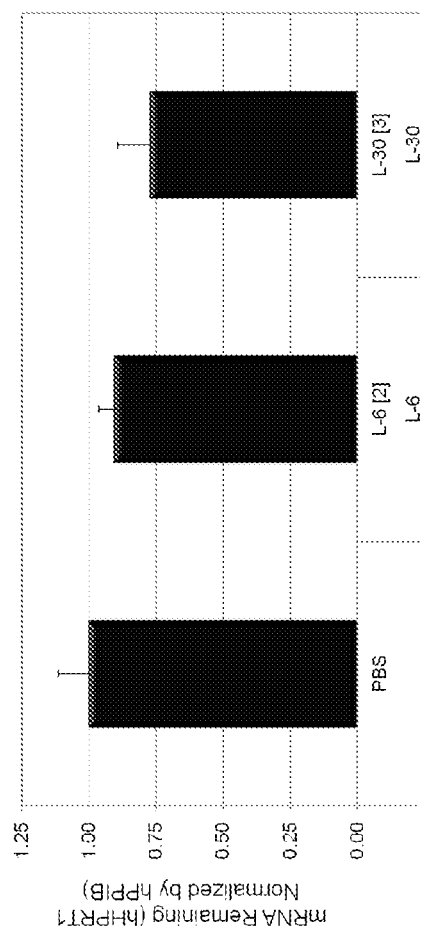
FIG. 23 is a graph showing in vivo knockdown of HPRT1 mRNA in 22Rv1 prostate cancer SC xenograft with a dose of lipid particles containing 10 mg/kg of DsiRNA at days 1 and 3 in two formulations, L-6 [2] and L-30 [2], followed by tissue harvesting at day 5. Values in the bar with error represent mean+SEM (N=7/group).
Figure 24:
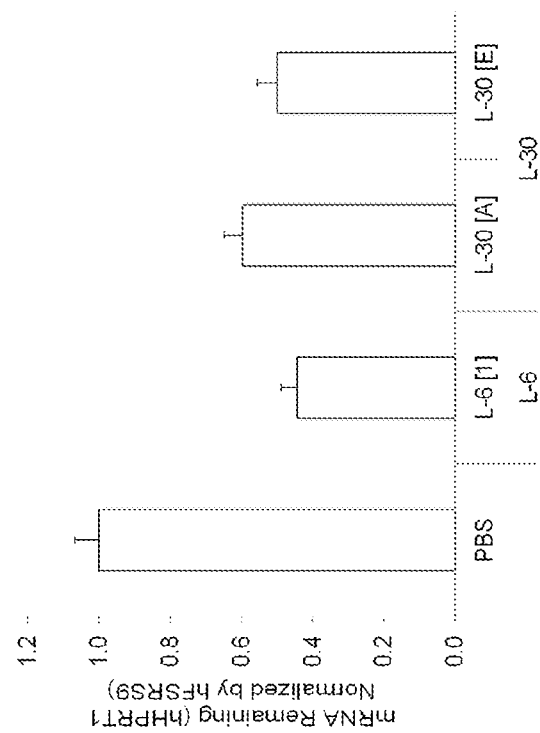
FIG. 24 is a graph showing in vivo knockdown of HPRT1 mRNA in 22Rv1 prostate cancer implanted in liver with a dose of lipid particles containing 10 mg/kg of DsiRNA at days 1 and 3 in three formulations, L-6 [1], L-30 [A], and L-30 [E], followed by tissue harvesting at day 5. Values in the bar with error represent mean+SEM (N=7/group).

Experiments that generated FIG. 23 were dosed at 10 mg/kg DsiRNA in L-6 [2] and L30 [3] formulated lipid particles and administered on days 1 and 3 of the experiment. The tumors were harvested on day 5. Knockdown of hHPRT1 mRNA was measured in 22Rv1 prostate cancer SC xenograft tumor tissues. A greater level of HPRT1 target mRNA knockdown was observed for the L-30 [3] formulation compared to the L-6 [2] formulation. The results of hHPRT1 knockdown in 22Rv1 prostate cancer implanted in the liver are shown in FIG. 24. Experiments were set up similar to experiments performed in FIG. 23. In the particular experiments of FIG. 24, a greater level of HPRT1 target mRNA knockdown was observed for the L-6 [1] formulation compared to both the L-30 [A] and L-30 [E] formulations. Accordingly, any of the lipids described herein can be used to replaced L-6 or L-30 in the specific compositions of lipid formulations in Table 9 and any dsRNA can be used to reduce the expression of a target gene associated with cancer (e.g., any cancer described herein).

TABLE 11

|  | Lipids | L-6 [1][2] | L-6 [2][2] | L-30 [3][2] |
|---|---|---|---|---|
| RNA-binding agents | DODMA | 25.9 | 25.9 | 25.9 |
|  | PEG$_{2000}$-DMPE | 2.9 | 2.9 | 2.9 |
| Transfection lipids | L-6/L-30 | 21.6 | 21.6 | 21.6 |
|  | DSPC | 13.8 | 13.8 | 13.8 |
|  | Cholesterol | 33.0 | 28.8 | 28.8 |
|  | PEG$_{2000}$-DSPE | 2.8 | 7.0 | 7.0 |
| Mixing |  | Batch | Batch | Batch |
| Ethanol %[1] |  | 4% | 4% | 4% |
| LNP Buffer |  | PBS | PBS | PBS |

[1]Prior to purification;
[2]Lipid mole percentage

Example 16: Lipid Formulation Containing L-30 with dsRNA

Table 12 provides specific components of a lipid formulation comprising L-30 as the transfection lipid. Any useful solvent or solvent system can be used to introduce the RNA-binding agents and the DsiRNA into the formulation, including solvents and solvent systems (e.g., aqueous and/or non-aqueous solvent(s)) that are the same or different as that for the transfection lipids. Furthermore, any of the lipids described herein can be used to replace L-30 as the transfection lipid in Table 12 (e.g., any described herein, such as in Table 1) and any dsRNA can be used to reduce the expression of a target gene (e.g., a target gene associated with cancer or a disease described herein).

TABLE 12

|  | Component | MW (g/mol) | Amount (mg) | Amount (mmol) | mol % |
|---|---|---|---|---|---|
| RNA-binding agents | DsiRNA | 17000 | 1.00 | 0.00006 | — |
|  | DODMA | 620.09 | 4.43 | 0.0071 | 25.9 |
|  | PEG-DMPE | 2693.3 | 2.12 | 0.0008 | 2.9 |
|  | Total |  | 6.55 | 0.0079 | 28.7 |
| Transfection lipids | L-30 | 613.05 | 3.65 | 0.0060 | 21.6 |
|  | PEG-DSPE | 2805.5 | 2.14 | 0.0008 | 2.8 |
|  | DSPC | 790.16 | 3.01 | 0.0038 | 13.8 |
|  | Cholesterol | 386.65 | 3.53 | 0.0091 | 33.1 |
|  | Total |  | 12.33 | 0.020 | 71.3 |
| Transfection lipid: DsiRNA |  |  | 12 | 334 | — |
| Total lipid |  |  | 18.88 | 0.028 | 100.0 |
| Total lipid: DsiRNA |  |  | 19 | 469 | — |

TABLE 12-continued

| Component | MW (g/mol) | Amount (mg) | Amount (mmol) | mol % |
|---|---|---|---|---|
| Total cationic lipid[1] |  | 8.08 | 0.0131 | 47.5 |
| Cationic lipid: DsiRNA |  | 8 | 223 | — |

[1]Combination of DODMA and L-30

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A compound having the formula:

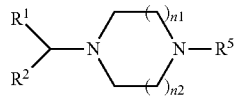

wherein each $R^1$ and $R^2$ is, independently, $C_{11-24}$ alkyl, $C_{11-24}$ alkenyl, or $C_{11-24}$ alkynyl;

each n1 and n2 is, independently, an integer from 1 to 2; and $R^5$ is selected from the group consisting of H, $C_{1-6}$ alkyl, and heterocyclyl.

2. The compound of claim 1, wherein each $R^1$ and $R^2$ is $C_{11-24}$ alkenyl.

3. The formulation of claim 2, further comprising a lipid particle comprising a transfection lipid.

4. The formulation of claim 3, wherein the one or more transfection lipid, comprises from 5 mol % to 20 mol % of the neutral lipid, from 0.5 mol % to 10 mol % of the PEG-lipid conjugate, and from 20 mol % to 40 mol % of the sterol derivative.

5. The compound of claim 1, wherein $R^5$ is $C_{1-6}$ alkyl.

6. The compound of claim 5, wherein each $R^1$ and $R^2$ is $C_{11-24}$ alkenyl.

7. The formulation compound of claim 6, wherein the $C_{1-6}$ alkyl is a methyl.

8. A formulation comprising a compound of claim 1, the formulation further comprising a cationic lipid, a neutral lipid, a sterol derivative and a dsRNA.

9. The formulation of claim 8, wherein the cationic lipid is selected from the group consisting of N,N-dimethyl-(2,3-dioleyloxy) propylamine (DODMA), 1,2-di-O-octadecenyl-3-trimethylammonium propane (DOTMA), 1,2-dipalmitoyl-sn-glycero-O-ethyl-3-phosphocholine (DPePC), 1,2-dioleoyl-3-dimethylammonium propane (DODAP), and 1,2-dioleoyl-3-trimethylammonium-propane (DOTAP); and the neutral lipid is selected from the group consisting of 1,2-distearoyl-sn-glycero-3-phosphocholine (DSPC), 1-palmitoyl-2-oleoyl-sn-glycero-3-phosphocholine (POPC), 1,2-dioleoyl-glycero-sn-3-phosphoethanolamine (DOPE), and sphingomyelin (SM).

10. The formulation of claim 9, wherein the sterol derivative is cholesterol.

11. The formulation of claim 8, wherein the cationic lipid is DODMA and the neutral lipid is DSPC.

12. The formulation of claim 8, wherein the formulation further comprises a PEG-lipid conjugate.

13. The formulation of claim 12, wherein the PEG-lipid conjugate is selected from the group consisting of 1,2-dimyristoyl-sn-glycerol-3-(methoxy-polyethylene glycol) (PEG-DMG), 1,2-dimyristoyl-sn-glycero-3-phosphoethanolamine-N-(carbonyl-methoxy-polyethylene glycol) (PEG-DMPE), 1,2-distearoyl-sn-glycero-3-phosphoethanolamine-N-(carbonyl-methoxy-polyethylene glycol) (PEG-DSPE), 1,2-dipalmitoyl-sn-glycero-3-phosphoethanolamine-N-(carbonyl-methoxy-polyethylene glycol) (PEG-DPPE), 1,2-dipalmitoyl-sn-glycerol-3-(methoxy-polyethylene glycol) (PEG-DPG), 1,2-dioleoyl-sn-glycero-3-phosphoethanolamine-N-(carbonyl-methoxy-polyethylene glycol) (PEG-DOPE), and 1,2-dioleoyl-sn-glycerol-3-(methoxy-polyethylene glycol) (PEG-DOG).

14. The formulation of claim 12, wherein the PEG-lipid conjugate is PEG-DMPE or PEG-DSPE.

15. The formulation of claim 8, wherein the sterol derivative is selected from the group consisting of cholesterol; cholestanone; cholestenone; coprostanol; 3β-[-(N—(N',N'-dimethylaminoethane)-carbamoyl]cholesterol (DC-cholesterol); bis-guanidium-tren-cholesterol (BGTC); (2S,3S)-2-(((3 S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonylamino)ethyl 2,3,4,4-tetrahydroxybutanoate (DPC-1); (2S,3S)-((3 S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4,4-tetrahydroxybutanoate (DPC-2); bis((3 S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate (DPC-3); and 6-(((3 S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate (DPC-4).

16. The formulation of claim 8, wherein the dsRNA comprises from 10 mol % to 40 mol % of one or more cationic lipids and from about 0.5 mol % to 10 mol % of one or more PEG-lipids.

17. The formulation of claim 8, wherein the dsRNA has a length selected from the group consisting of 10 to 40 nucleotides, 16 to 30 nucleotides, 19 to 29 nucleotides, 25 to 35 nucleotides and 8-50 nucleotides.

18. The formulation of claim 8, wherein the formulation, comprises from 1:10 (w/w) to about 1:100 (w/w) ratio of the dsRNA to the total lipid present in the formulation.

19. The formulation claim 8, further comprising a liposome, a lipoplex, or a micelle.

20. The formulation of claim 19, wherein the liposome is a lipid nanoparticle.

21. A formulation comprising from 20 mol % to 25 mol % of the compound of claim 1, from 20 mol % to 30 mol % of a cationic lipid, from 2 mol % to 8 mol % of a PEG-lipid conjugate, from 10 mol % to 20 mol % of a neutral lipid, and from 25 mol % to 35 mol % of a sterol derivative.

22. A formulation comprising 22 mol % of the compound of claim 1, 26 mol % of a cationic lipid, 5 mol % to 9 mol % of a PEG-lipid conjugate, 14 mol % of a neutral lipid, and 29 mol % to 33 mol % of a sterol derivative.

23. A formulation comprising a compound of claim 1, wherein the formulation further comprises one or more components selected from a group consisting of a cationic lipid, a neutral lipid, a sterol derivative, a PEG-lipid conjugate, lipid particles comprising one or more RNA-binding agents, transfection lipids, a dsRNA, a liposome, a lipoplex, and a micelle.

24. A pharmaceutical composition comprising the compound of claim 1, and a pharmaceutically acceptable excipient.

25. A method of treating or preventing a disease in a subject, the method comprising administering to the subject the compound of claim 1, in an amount sufficient to treat the disease, wherein the disease is selected from the group consisting of hepatocellular carcinoma, lung cancer, prostate cancer, or neuroblastoma.

26. A method of modulating the expression of a target nucleic acid in a subject, the method comprising administering to the subject the compound of claim 1, in an amount sufficient to reduce the expression of the target gene in the subject, wherein the target gene is, selected from the group consisting of ABL1, AR, β-Catenin, BCL1, BCL2, BCL6, CBFA2, CBL, CSF1R, ERBA1, ERBA2, ERBB1, ERBB2, ERBB3, ERBB4, ETS1, ETS2, ETV6, FGR, FOS, FYN, HCR, HRAS, JUN, KRAS, LCK, LYN, MET, MDM2, MLL1, MLL2, MLL3, MYB, MYC, MYCL1, MYCN, NRAS, PIM1, PML, RET, SRC, TAL1, TAL2, TCL3, TCL5, YES, BRCA1, BRCA2, MADH4, MCC, NF1, NF2, RB1, TP53, WT1, ApoB100, CSN5, CDK6, ITGB1, TGFβ1, Cyclin D1, PLK1, and KIF1-binding protein; and wherein expression of the target gene is reduced in the subject.

27. A method of modulating the expression of a target nucleic acid in a subject, the method comprising administering the compound of claim 1 in an amount sufficient to reduce the expression of the target gene in the subject, wherein the target gene is, selected from the group consisting of ABL1, AR, β-Catenin, BCL1, BCL2, BCL6, CBFA2, CBL, CSF1R, ERBA1, ERBA2, ERBB1, ERBB2, ERBB3, ERBB4, ETS1, ETS2, ETV6, FGR, FOS, FYN, HCR, HRAS, JUN, KRAS, LCK, LYN, MET, MDM2, MLL1, MLL2, MLL3, MYB, MYC, MYCL1, MYCN, NRAS, PIM1, PML, RET, SRC, TAL1, TAL2, TCL3, TCL5, YES, BRCA1, BRCA2, MADH4, MCC, NF1, NF2, RB1, TP53, WT1, ApoB100, CSN5, CDK6, ITGB1, TGFβ1, Cyclin D1, PLK1, and KIF1-binding protein; and wherein expression of the target gene is reduced in the subject.

\* \* \* \* \*

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
gccagacuuu guuggauuug aaatt                                         25

<210> SEQ ID NO 2
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n is 2'-O-methyl-C
<220> FEATURE:
<221> NAME/KEY: misc_feature
<222> LOCATION: (13)..(13)
<223> OTHER INFORMATION: n is 2'-O-methyl-A
<220> FEATURE:
<221> NAME/KEY: misc_feature
<222> LOCATION: (15)..(15)
<223> OTHER INFORMATION: n is 2'-O-methyl-C
<220> FEATURE:
<221> NAME/KEY: misc_feature
<222> LOCATION: (17)..(17)
<223> OTHER INFORMATION: n is 2'-O-methyl-A
<220> FEATURE:
<221> NAME/KEY: misc_feature
<222> LOCATION: (19)..(19)
<223> OTHER INFORMATION: n is 2'-O-methyl-G
<220> FEATURE:
<221> NAME/KEY: misc_feature
<222> LOCATION: (21)..(21)
<223> OTHER INFORMATION: n is 2'-O-methyl-C
<220> FEATURE:
```

```
<221> NAME/KEY: misc_feature
<222> LOCATION: (23)..(23)
<223> OTHER INFORMATION: n is 2'-O-methyl-G
<220> FEATURE:
<221> NAME/KEY: misc_feature
<222> LOCATION: (25)..(25)
<223> OTHER INFORMATION: n is 2'-O-methyl-C
<220> FEATURE:
<221> NAME/KEY: misc_feature
<222> LOCATION: (26)..(27)
<223> OTHER INFORMATION: n is 2'-O-methyl-U

<400> SEQUENCE: 2
aauuucaaau ncnanananu nungnnn                                          27
```